(12) United States Patent
Shibue et al.

(10) Patent No.: US 6,568,265 B2
(45) Date of Patent: May 27, 2003

(54) HUMIDITY SENSOR AND METHOD FOR MAKING

(75) Inventors: Akira Shibue, Chuo-ku (JP); Kenryo Namba, Chuo-ku (JP)

(73) Assignee: TDK Corporation, Tokyo (JP)

( * ) Notice: Subject to any disclaimer, the term of this patent is extended or adjusted under 35 U.S.C. 154(b) by 214 days.

(21) Appl. No.: 09/820,644

(22) Filed: Mar. 30, 2001

(65) Prior Publication Data

US 2001/0037681 A1 Nov. 8, 2001

(30) Foreign Application Priority Data

Mar. 31, 2000 (JP) ......................... 2000-098643

(51) Int. Cl.⁷ .......................... G01N 19/10; B32B 9/04; B05D 5/12
(52) U.S. Cl. ................. 73/335.05; 73/335.02; 73/29.01; 73/29.02; 427/103; 427/407.1; 427/508; 428/332; 428/336; 428/446; 428/447; 428/448; 428/523
(58) Field of Search ............... 73/29.01, 29.02, 73/335.05, 335.02; 338/34, 35; 428/446, 447, 448, 332, 336, 523; 427/103, 407.1

(56) References Cited

U.S. PATENT DOCUMENTS 5,072,262 A * 12/1991 Uekita et al. ............... 257/410
5,546,802 A 8/1996 Yoshimura et al.

FOREIGN PATENT DOCUMENTS

| JP | 61-054176 | 11/1986 |
| JP | 62-007976 | 2/1987 |
| JP | 02-024465 | 5/1990 |
| JP | 07-018832 | 3/1995 |
| JP | 07-318525 | 12/1995 |
| JP | 2808255 | 7/1998 |

* cited by examiner

Primary Examiner—Robert Dawson
Assistant Examiner—Michael J Feely
(74) Attorney, Agent, or Firm—Oblon, Spivak, McClelland, Maier & Neustadt, P.C.

(57) ABSTRACT

A humidity sensor includes a pair of interdigital electrodes disposed on an insulating substrate and defining a gap therebetween, an undercoat layer of silane compound lying on the gap-defining electrodes and substrate, and a humidity sensitive thin film lying thereon. The humidity sensitive thin film is formed of a crosslinked product of a conductive polymer having ethylenically unsaturated groups, and physically bound to the undercoat layer through an interpenetrating polymer network. The sensor is fully resistant to water so that it ensures stable operation over a long time even in a dew condensing atmosphere. The sensor is free of hysteresis and able to measure humidity over a very wide range.

13 Claims, 38 Drawing Sheets

■ SENSOR OF EXAMPLE 1
● COMPARATIVE SENSOR
□ SENSOR OF EXAMPLE 1 AFTER EXPOSURE TO $Cl_2$ GAS
○ COMPARATIVE SENSOR AFTER EXPOSURE TO $Cl_2$ GAS

—■—SENSOR OF EXAMPLE 1
—●—COMPARATIVE SENSOR
—□—SENSOR OF EXAMPLE 1 AFTER EXPOSURE TO $NO_2$ GAS
—○—COMPARATIVE SENSOR AFTER EXPOSURE TO $NO_2$ GAS

—■— SENSOR OF EXAMPLE 1
—●— COMPARATIVE SENSOR
—□— SENSOR OF EXAMPLE 1 AFTER EXPOSURE TO $SO_2$ GAS
--○-- COMPARATIVE SENSOR AFTER EXPOSURE TO $SO_2$ GAS

HUMIDITY SENSOR AND METHOD FOR MAKING

TECHNICAL FIELD

This invention relates to a humidity sensor for detecting and determining moisture in the surrounding atmosphere and a method for preparing the same.

BACKGROUND ART

Conventional humidity sensors are designed to detect humidity through changes of electrical properties, typically electric resistance. Known sensors use electrolytes such as lithium chloride, metal oxides, and organic polymers as the humidity sensitive material. However, the humidity sensors using electrolytes such as lithium chloride can measure only a narrow range of humidity and are less resistant to water in that their performance can be altered by dew condensation and wetting. The humidity sensors using metal oxides are resistant to water, but low sensitive. Because of the lack of long-term stability when used alone, they require a heat cleaning circuit which would add to the operating cost. The sensor structure is complex.

Among the humidity sensitive materials, organic polymers, especially polymeric electrolytes having quaternary ammonium salt groups have been widely used in commercial and industrial applications and so appreciated. For example, Japanese Patent Publication (JP-B) No. 61-54176 discloses a humidity sensitive material comprising aggregates of latex particles formed of a copolymer between a hydrophobic monomer and an ionic or non-ionic hydrophilic monomer and having a hydrophilic surface layer. There are exemplified some cationic compounds having primary to quaternary ammonium salts.

JP-B 62-7976 discloses a humidity sensitive material in the form of a polymer which is obtained by polymerizing a compound containing 2-hydroxy-3-methacryloxypropyl-trimethylammonium chloride to a degree of polymerization of 1,000 to 10,000.

JP-B 2-24465 discloses a humidity sensitive thin film of a polymer having the structural formula:

wherein $R^1$ to $R^4$ are alkyl, $X^-$ is a halide ion, A and B each are $-(CH_2)_m-$ wherein $m \geq 2$. The polymer may be blended with another polymer such as polyvinyl pyrrolidone for the purposes of improving substrate adhesion and water resistance. The blend is also effective in forming a humidity sensitive thin film.

Humidity sensors using the polymeric electrolytes exemplified above as the humidity sensitive material, however, are still low in water resistance in that the polymeric electrolytes can be partially leached in a high humidity region, especially in a dew condensing atmosphere. They also suffer from a hysteresis phenomenon that they produce different outputs at the same humidity depending on whether the humidity is increasing or decreasing. In a low humidity region having a relative humidity (RH) of less than 10%, they have so high resistance values that practical humidity measurement is impossible.

U.S. Pat. No. 5,546,802 (corresponding Japanese Patent No. 2,808,255 by TDK Corp.) discloses a humidity sensor comprising a polymer electrolyte having ethylenically unsaturated reactive groups introduced at ends and quaternary ammonium salt groups. This sensor is fully resistant to water, steadily operates in a condensing atmosphere and produces consistent outputs over a wide humidity region.

However, in order that the humidity sensor using a polymer electrolyte as defined above produce consistent outputs in a condensing atmosphere, the thickness of the humidity sensitive film must be restricted below a certain limit. Such a thin film is so sensitive to various gases that the output characteristics largely vary therewith. Therefore, the sensor has the drawback of lacking long-term stability under hot humid conditions. If the thickness of the humidity sensitive film is increased beyond the limit, stripping and failure are likely to occur.

SUMMARY OF THE INVENTION

A primary object of the present invention is to provide a humidity sensor device having a humidity sensitive thin film which is resistant to water, maintains effective, stable performance over a long time even in a dew condensing atmosphere, and produces accurate outputs in a stable manner over a wide humidity region.

In one aspect, the invention provides a humidity sensor comprising an insulating substrate, a pair of opposed electrodes disposed on the substrate and defining a gap therebetween, a silicon-containing undercoat layer lying on at least the gap, and a humidity sensitive thin film lying thereon. The humidity sensitive thin film comprises a crosslinked product of a conductive polymer having ethylenically unsaturated groups and is physically bound to the undercoat layer through an interpenetrating polymer network.

In another aspect, the invention provides a humidity sensor comprising an insulating substrate, a pair of opposed electrodes disposed on the substrate and defining a gap therebetween, a silicon-containing undercoat layer lying on at least the gap, and a humidity sensitive thin film lying thereon. The humidity sensitive thin film comprises a crosslinked product of a polymer of the following formula (I) and is bound to said undercoat layer through covalent bonds having not undergone dehalogenation reaction.

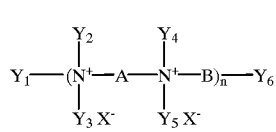

(I)

Herein A and B each are a divalent group; $Y_1$, $Y_2$, $Y_3$, $Y_4$, $Y_5$ and $Y_6$ each are a monovalent group, at least one of $Y_1$ to $Y_6$ is a group terminated with an ethylenically unsaturated reactive group; at least two of $Y_1$, $Y_2$, $Y_3$, $Y_4$, $Y_5$, A and portions thereof adjoining the nitrogen (N) atom or at least two of $Y_4$, $Y_5$, $Y_6$, B and portions thereof adjoining the nitrogen (N) atom, taken together, may form a ring with the nitrogen atom; $X^-$ is a halide ion; and letter n is a number of 2 to 5,000.

Preferably, the humidity sensitive thin film of the second embodiment is physically bound to said undercoat layer through an interpenetrating polymer network.

Typically, the humidity sensitive thin film has a thickness of 0.1 to 20 μm.

In a preferred embodiment, the polymer has the following formula (II) or (III).

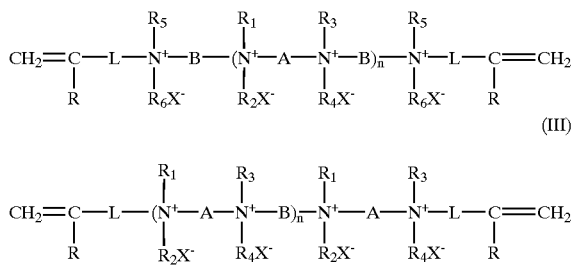

(II)

$$CH_2=C-L-N^+-B-(N^+-A-N^+-B)_n-N^+-L-C=CH_2$$
with $R_5, R_1, R_3, R_5$ above and $R, R_6X^-, R_2X^-, R_4X^-, R_6X^-, R$ below (III)

$$CH_2=C-L-(N^+-A-N^+-B)_n-N^+-A-N^+-L-C=CH_2$$
with $R_1, R_3, R_1, R_3$ above and $R, R_2X^-, R_4X^-, R_2X^-, R_4X^-, R$ below Herein A and B each are a divalent group; each of $R_1$, $R_2$, $R_3$, and $R_4$ is an alkyl or alkenyl group; a pair of $R_1$ and $R_2$, $R_1$ and A or a portion of A, $R_2$ and A or a portion of A, $R_3$ and $R_4$, $R_3$ and A or a portion of A, $R_4$ and A or a portion of A, $R_1$ and $R_3$, $R_1$ and $R_4$, $R_2$ and $R_3$, or $R_2$ and $R_4$, taken together, may form a ring with the nitrogen (N) atom; L is a divalent group; R is hydrogen or an alkyl group; $X^-$ is a halide ion; n is a number of 2 to 5,000; and $R_5$ and $R_6$ each are an alkyl or alkenyl group.

Preferably, the divalent group represented by A is an alkylene, alkenylene or arylene group or a mixture thereof; the divalent group represented by B is an alkylene, alkenylene or arylene group in which at least one of an oxy group (—O—) and a carbonyl group (—CO—) may intervene or a mixture thereof.

The polymer is typically obtained by reacting a diamine compound with a dihalogen compound to form an intermediate polymer and introducing an ethylenically unsaturated reactive group into the intermediate polymer at each end.

In a further aspect, the invention provides a method for preparing a humidity sensor comprising the steps of:

applying a silane compound containing at least a hydrolyzable group and an organic group having an unsaturated bond onto a substrate to form an undercoat layer, applying a solution containing a conductive polymer having ethylenically unsaturated groups onto the undercoat layer, and exposing the conductive polymer to radiation for crosslinking the polymer and bonding the polymer with the silane compound to thereby form a humidity sensitive thin film.

Preferably, the bond between the conductive polymer and the silane compound is due to covalent bonds by crosslinking between the ethylenically unsaturated groups and the unsaturated bonds. Most often, the radiation is ultraviolet radiation. Preferably the conductive polymer used herein has the formula (I) defined above.

(I)

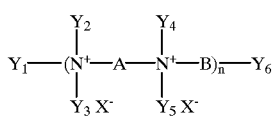

$$Y_1-(N^+-A-N^+-B)_n-Y_6$$
with $Y_2, Y_4$ above and $Y_3X^-, Y_5X^-$ below

Herein A and B each are a divalent group; $Y_1$, $Y_2$, $Y_3$, $Y_4$, $Y_5$ and $Y_6$ each are a monovalent group, at least one of $Y_1$ to $Y_6$ is a group terminated with an ethylenically unsaturated reactive group; at least two of $Y_1$, $Y_2$, $Y_3$, $Y_4$, $Y_5$, A and portions thereof adjoining the nitrogen (N) atom or at least two of $Y_4$, $Y_5$, $Y_6$, B and portions thereof adjoining the nitrogen (N) atom, taken together, may form a ring with the nitrogen atom; $X^-$ is a halide ion; and letter n is a number of 2 to 5,000.

In a preferred embodiment, the silane compound has the following formula (IV):

$$X^0{}_n(CH_3)_{3-n}Si\text{-}R^0 \tag{IV}$$

wherein $X^0$ is a hydrolyzable group, $R^0$ is an organic group, and n is an integer of 1, 2 or 3.

Advantages

In the humidity sensor of the invention, an undercoat layer having unsaturated bonds connected via silicon covers a pair of opposed electrodes on an insulating substrate, and a humidity sensitive layer of a conductive polymer of any of formulas (I) to (III) lies thereon.

The undercoat layer comprising a compound having an unsaturated bond connected via silicon, preferably of formula (IV) is provided for the purpose of establishing a firm or intimate bond between the overlying humidity sensitive layer of conductive polymer and the underlying substrate and electrodes. The compound is typically selected from silane coupling agents or silane compounds having vinyl, methacrylic or acrylic groups.

The humidity sensitive layer contains a crosslinked product of a polymer represented by formula (I), preferably formula (II) or (III). This layer is formed by applying a solution of the polymer and causing the polymer to be crosslinked, preferably by exposure to UV radiation. During the crosslinking step, the polymer forms covalent bonds or physical bonds with the undercoat layer having unsaturated bonds connected via silicon. As a consequence, there is formed a robust humidity sensitive film.

Upon exposure to UV radiation, the ethylenically unsaturated groups on the conductive polymer and the unsaturated double bonds on the compound are polymerized and mutually crosslinked within the respective layers and at the interface therebetween. At this point, in the conductive polymer layer, the humidity sensitive material becomes insolubilized in water by polymerization. At the interface with the undercoat layer having unsaturated bonds connected via silicon, covalent bonds are formed via silicon to bind the humidity sensitive layer of conductive polymer to the electrodes and insulating substrate through the undercoat layer. Alternatively, the humidity sensitive layer is closely bonded to the electrode and insulating substrate through the undercoat layer due to covalent bonds by crosslinking between ethylenically unsaturated groups and unsaturated bonds and physical bonds by an interpenetrating polymer network (IPN) resulting from crosslinking between unsaturated bonds. By virtue of this phenomenon, the humidity sensitive layer is firmly bound to the electrode and insulating substrate through the undercoat layer so that the humidity sensitive film has improved water resistance and wear resistance. The humidity sensor is fully resistant to water. The humidity sensing function is not lost at all, albeit crosslinking.

The interpenetrating polymer network (IPN) means that distinct polymer molecules of a three-dimensional network component are physically intertwined without forming chemical bond sites so that they penetrate into different phases in a network manner. As seen from formulas (I) to (III), the polymer of the conductive polymer layer is structurally characterized by containing a quaternary ammonium salt group (including a cyclized one) in its backbone and having an ethylenically unsaturated reactive group at one or both, preferably both of the terminal ends of the polymer.

In the humidity sensitive thin film containing the specific polymer, the quaternary ammonium salt group moiety of the polymer molecule contributes to electric conductivity and the counter ion thereto is dissociated with moisture in the surrounding atmosphere to develop ionic conduction. Humidity is detected by utilizing the phenomenon that the degree of dissociation varies as the moisture content in the atmosphere increases or decreases.

Since the polymer contains a quaternary ammonium salt group in its backbone, the humidity sensor produces accurate outputs without hysteresis.

It is noted that JP-A 7-318525 discloses a humidity sensor comprising a polymer electrolyte bound to a substrate surface through covalent bonds containing —Si— bonds. As opposed to the present invention, the layer between the substrate and the humidity sensitive film is a silane compound having halide groups, and the covalent bonds between the compound layer and the humidity sensitive material results from dehalogenation reaction. It is described nowhere that the crosslinking of a humidity sensitive material and the crosslinking between a humidity sensitive material and a silane compound are induced by exposure to radiation. In these regards, the humidity sensor of JP-A 7-318525 is apparently different from the humidity sensor of the present invention.

JP-B 7-018832 discloses a humidity sensor comprising a humidity sensitive film based on an alkoxysilane having quaternary ammonium groups. An organopolysiloxane has quaternary ammonium groups, which are chemically bonded by heating. It is described nowhere that the crosslinking of a humidity sensitive material and the crosslinking between a humidity sensitive material and a silane compound are induced by exposure to radiation. In these regards, the humidity sensor of JP-B 7-018832 is apparently different from the humidity sensor of the present invention.

BRIEF DESCRIPTION OF THE DRAWINGS

The above and other features and advantages of the present invention will be better understood by reading the following description taken in conjunction with the accompanying drawings.

DESCRIPTION OF THE PREFERRED EMBODIMENT

Figure 1:
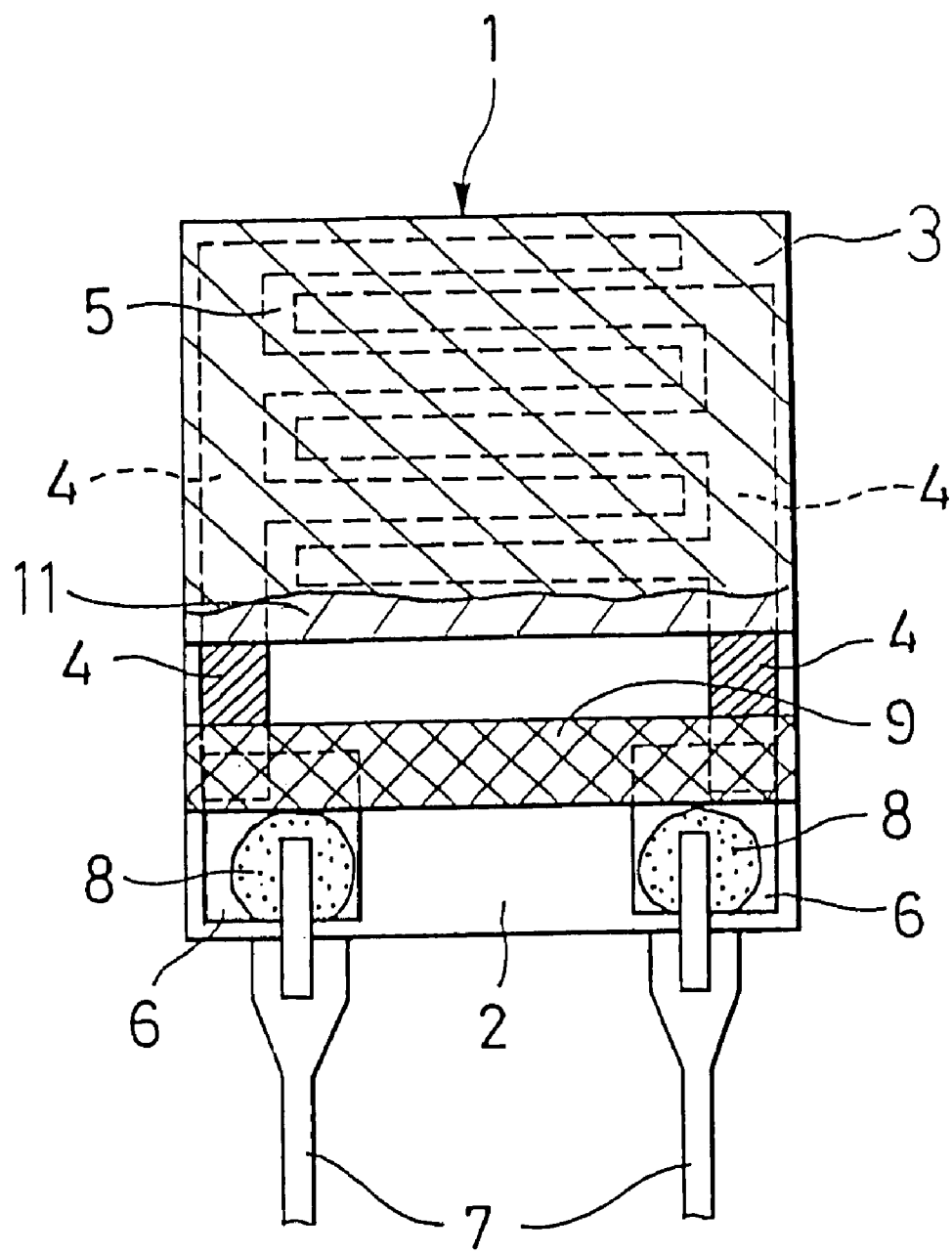
FIG. 1 is a plan view of a humidity sensor according to one embodiment of the invention.

The humidity sensor of the invention includes an insulating substrate, a pair of opposed electrodes disposed on the substrate and defining a gap therebetween, an undercoat layer of a compound having an unsaturated bond connected through silicon (i.e., silane compound) lying on the gap-defining electrodes and substrate, and a humidity sensitive thin film lying thereon.

The silicon-containing compound of which the undercoat layer is constructed, that is, silane compound preferably has the following formula (IV).

Herein $X^0$ is a hydrolyzable group, $R^0$ is an organic group, and n is an integer of 1, 2 or 3.

The hydrolyzable group $X^0$ is an active group capable of bonding with the insulating substrate and the electrodes thereon directly or after hydrolysis. Exemplary hydrolyzable groups are acetoxy, alkoxy, oxime and amide groups and highly active chloro and amino groups, with the alkoxy groups such as methoxy and ethoxy being preferred for storage stability and ease of handling.

The organic groups $R^0$ include those of the non-reactive type such as alkyl groups and those of the reactive type such as epoxy, amino, acrylic and methacrylic groups. Both types of groups are effective for forming physical and chemical bonds with the humidity sensitive film, although those organic groups capable of crosslinking with ethylenically unsaturated groups in formula (I) to form covalent bonds, especially those organic groups having unsaturated double bonds are more effective.

Illustrative organic groups include acryloyloxy, methacryloyloxy, acryloylimino, methacryloylimino, vinyl, allyl, diallylmethyl, allyloxy, diacryloylimino, and dimethacryloylimino groups.

All the compounds of formula (IV) having combinations of the above-mentioned substituents are effective although preferred are vinyltrimethoxysilane, vinyltriethoxysilane, vinyltris(β-methoxyethoxy)silane, γ-methacryloxypropyltrimethoxysilane, γ-methacryloxypropylmethyldimethoxysilane, γ-methacryloxypropylmethyldiethoxysilane, and γ-methacryloxypropyltriethoxysilane, among others.

In a preferred embodiment, the undercoat layer contains a silane compound of formula (IV) and is thinly formed on the insulating substrate and the electrodes, ideally as a monomolecular layer. The method of forming the undercoat layer is not critical as long as the above-mentioned requirements are met. Among others, the following method is recommended since it is simple and reliable.

First, a coating solution containing the compound of formula (IV) is prepared. The coating solution may be an aqueous, alcohol or acetic acid solution containing 0.1 to 10% by weight of the compound. If the compound is liquid at room temperature, this original liquid may be used as such.

The coating solution is applied onto the insulating substrate and the electrodes which have been previously cleaned with alcohols, acetone, water or the like, by suitable techniques such as dipping, brush coating and dispensing. The coating is allowed or caused to intimately join to the insulating substrate and the electrodes through hydrogen bonds, physical adsorption and chemical bonds. As described in B. Arkles, Chem. Tech., 765, December 1977, the silane compound in the coating solution undergoes hydrolysis to produce silanol groups ( . . . Si—OH), which partially condense to form oligomers, and in this state, further undergoes dehydration reaction with hydroxyl groups on the surfaces of the insulating substrate and electrodes, to form stable chemical bonds.

To promote the formation of such bonds, the coating obtained by applying the coating solution and drying is heat treated at a temperature of about 40 to 180° C. for about 5 to 30 minutes. Thereafter, the extra compound which has not participated in bonding with the insulating substrate and electrodes is removed. A suitable removal means, which depends on a particular silane compound used, is usually by washing with methanol, ethanol or water. Ultrasonic cleaning or heating may also be used.

The humidity sensitive thin film contains a crosslinked product of a polymer having the formula (I). Formula (I) is described in detail.

In formula (I), A, B, $X^-$ and n are as defined above and will be described later in conjunction with formulae (II) and (III).

Each of $Y_1$ to $Y_6$ is a monovalent group. At least one of $Y_1$ to $Y_6$ is a group terminated with an ethylenically unsaturated reactive group. Exemplary groups are acryloyloxy, methacryloyloxy, acryloylimino, methacryloylimino, vinyl, allyl, diallylmethyl, allyloxy, diacryloylimino, and dimethacryloylimino groups.

The other monovalent groups represented by $Y_1$ to $Y_6$ include alkyl groups, alkenyl groups and halogen atoms. Examples of the alkyl and alkenyl groups are the same as $R_1$ and analogs in formulae (II) and (III), which will be described later. Examples of the halogen atom include chlorine, bromine and iodine. Any two or more of $Y_1$ to $Y_5$, A, and portions thereof adjoining the nitrogen (N) atom, taken together, may form a ring with the nitrogen atom. Alternatively, any two or more of $Y_4$ to $Y_6$, B, and portions thereof adjoining the nitrogen (N) atom, taken together, may form a ring with the nitrogen atom. The ring thus formed is the same as the ring formed by $R_1$ and analogs in formulae (II) and (III), which will be described later.

The polymer of formula (I) should have at least one, preferably about two ethylenically unsaturated reactive groups. No upper limit is imposed on the number of such reactive groups although it is preferred that the polymer contains double bonds in an amount of $1 \times 10^{-3}$ to 2 meq/g, especially $2 \times 10^{-3}$ to 1 meq/g calculated as a double bond equivalent per polymer weight.

The monovalent groups represented by $Y_2$ to $Y_5$ may contain a linkage between recurring units in the molecular structure of formula (I) while the recurring units in formula (I) may be identical or different.

Preferably the polymer of formula (I) contains quaternary ammonium salt groups in an amount of 1.2 to 9.5 meq/g, especially 1.5 to 9.5 meq/g calculated as a cation equivalent per polymer weight.

Preferred among the polymers of formula (I) are polymers of formulae (II) and (III). In formulae (II) and (III) as well as in formula (I), each of A and B is a divalent group.

The divalent group represented by A is preferably an alkylene, alkenylene or arylene group or a mixture thereof. These groups may have substituents, for example, hydroxyl groups, alkyl groups such as methyl, and carbamoyl groups. The alkylene groups preferably have 1 to 20 carbon atoms in total and if substituted, they preferably have 1 to 5 hydroxyl groups. The alkenylene groups preferably have 2 to 10 carbon atoms in total. The arylene groups preferably have 6 to 20 carbon atoms in total. When the divalent group represented by A is a mixture of these groups, the mixture preferably has 3 to 20 carbon atoms in total.

Illustrative, preferred examples of A include

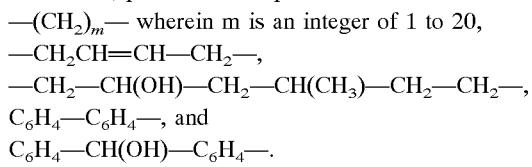

The divalent group represented by B is preferably an alkylene group, an alkylene group having an intervening oxy (—O—) and/or carbonyl (—CO—) group, an alkenylene group, an arylene group, or a mixture thereof. These groups may have substituents, for example, hydroxyl groups and alkenyl groups such as vinyl. The alkylene groups preferably have 1 to 20 carbon atoms in total and if substituted, they preferably have 1 to 5 hydroxyl groups. If —O— or —CO— intervenes in the alkylene group, the number of the intervening groups is preferably 1 to 5. The alkenylene groups preferably have 2 to 10 carbon atoms in total. The arylene groups preferably have 6 to 20 carbon atoms in total. When the divalent group represented by B is a mixture of these groups, the mixture preferably has 3 to 20 carbon atoms in total.

Illustrative, preferred examples of B include
—(CH$_2$)$_m$— wherein m is an integer of 1 to 20,
—(CH$_2$)$_2$—CH(OH)—CH$_2$—,
—CH$_2$—CH(OH)—CH$_2$—,
—CH$_2$—CH=CH—CH$_2$—,
—CH$_2$—CH(CH=CH$_2$)—,
—(CH$_2$—CH$_2$—O)$_2$—(CH$_2$)$_2$—,
—CH$_2$—(CO)—CH$_2$—, and
—CH$_2$—C$_6$H$_4$—CH$_2$—.

Each of R$_1$, R$_2$, R$_3$, and R$_4$ is an alkyl or alkenyl group. The alkyl groups represented by R$_1$ to R$_4$ preferably have 1 to 10 carbon atoms. They may be substituted ones although unsubstituted groups are preferred. Exemplary preferred alkyl groups are methyl, ethyl, propyl and butyl groups. The alkenyl groups represented by R$_1$ to R$_4$ preferably have 1 to 10 carbon atoms. They may be substituted ones although unsubstituted groups are preferred. Exemplary preferred alkenyl groups are vinyl, allyl, propenyl and butenyl groups.

A pair of R$_1$ and R$_2$, a pair of R$_1$ and A or a portion of A, a pair of R$_2$ and A or a portion of A, a pair of R$_3$ and R$_4$, a pair of R$_3$ and A or a portion of A, a pair of R$_4$ and A or a portion of A, a pair of R$_1$ and R$_3$, a pair of R$_1$ and R$_4$, a pair of R$_2$ and R$_3$, or a pair of R$_2$ and R$_4$, taken together, may form a ring with the nitrogen (N) atom. The ring is preferably a five or six-membered, especially six-membered nitrogenous heterocyclic ring. The ring may also be a bridged ring. Preferred examples of the nitrogenous heterocyclic ring include pyridine, 1,4-diazabicyclo[2.2.2]octane, piperidine, piperazine, and pyrazine rings which may have carbamoyl or other substituents if desired.

Each of R$_5$ and R$_6$ in formula (II) is an alkyl or alkenyl group. Preferred is an alkyl group, especially having 1 to 10 carbon atoms. It may have a substituent although unsubstituted alkyl groups are preferred. For example, methyl and ethyl groups are most preferred for R$_5$ and R$_6$. Examples of the alkenyl group represented by R$_5$ and R$_6$ are the same as described for R$_1$ to R$_4$.

In formulae (II) and (III), L is a divalent group. Preferred examples of L in formula (II) include —COO(CH$_2$)$_2$—, —CONH(CH$_2$)$_3$—, and —(CH$_2$)$_m$— wherein m is an integer of 1 to 20. Preferred examples of L in formula (III) include —OCH$_2$CH$_2$ —, —(CH$_2$)$_m$— wherein m is an integer of 1 to 20, —COO(CH$_2$)$_2$—, —COOCH$_2$CH(OH)CH$_2$—, and —CH$_2$—C$_6$H$_4$— (para- or meta-).

Alternatively, two or three of R$_5$, R$_6$ and L, taken together, may form a pyridine or another ring with the nitrogen (N) atom.

In formulae (II) and (III), R is a hydrogen atom or alkyl group, with the hydrogen atom and methyl being preferred.

In formulae (II) and (III), X$^-$ is a halide ion, for example, chloride, bromide and iodide ions. The chloride and bromide ions are preferred. A plurality of halide ions may be combined so as to provide the desired properties. The ions represented by X$^-$ are often identical although they may be different.

Letter n is a number of 2 to 5,000.

The polymers of formulae (I) to (III) generally have a number average molecular weight Mn of about 500 to about 1,000,000, preferably about 1,000 to about 100,000. A Mn of less than about 10,000 is preferred for ease of handling.

The preferred polymers of formulae (II) and (III) are prepared as follows.

The polymer of formula (II) is synthesized according to the following reaction scheme.

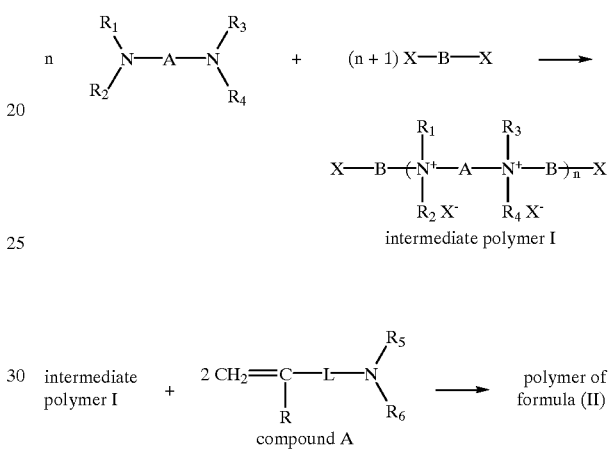

First, a diamine compound is reacted with a dihalogen compound to form an intermediate polymer I having a quaternary ammonium salt group and terminated with a halogen atom. In this regard, the reactants are reacted under conditions that the molar ratio of dihalogen compound to diamine compound is from 1.1 to 2.0. To assure that the intermediate polymer I is terminated with a halogen atom, the dihalogen compounds may be added in two divided portions wherein it is first added in an amount of 1 to 1.3 mol per mole of the diamine compound and the remainder is subsequently added. Reaction is effected in a non-aqueous solvent such as methanol, isopropanol, methoxyethanol and 2-ethoxyethanol at a reflux temperature or a temperature of about 100° C. for about 5 to 100 hours.

Next, intermediate polymer I is reacted with a compound A having an ethylenically unsaturated reactive group to introduce an ethylenically unsaturated reactive group at each end of intermediate polymer I, obtaining a polymer of formula (II). This reaction may be carried out subsequent to the first reaction. That is, the compound A having an ethylenically unsaturated reactive group is added to the reaction solution in an approximately equimolar amount to the dihalogen compound. Reaction is effected at a temperature of about 15 to 100° C. in the presence of a polymerization inhibitor (e.g., m-dinitrobenzene) for about 10 to 150 hours. If this reaction is effected under conditions that at least some of the ethylenically unsaturated reactive groups being introduced will undergo polymerization, then the resulting polymer is more resistant to water when used as a humidity sensitive thin film. To this end, reaction is preferably effected at 70° C. or higher, especially 70 to 100° C. Thereafter, the reaction solution was added dropwise to a suitable solvent such as acetone and ethyl acetate whereupon the reaction product will precipitate. The precipitate is collected by filtration and purified, recovering the end product.

The polymer of formula (III) is synthesized according to the following reaction scheme.

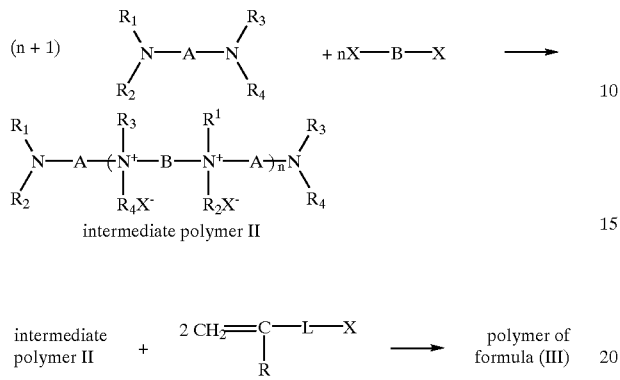

First, a diamine compound is reacted with a dihalogen compound to form an intermediate polymer II having a quaternary ammonium salt group and terminated with an amino group. In this regard, the reactants are reacted under conditions that the molar ratio of diamine compound to dihalogen compound is from 1.0 to 2.0, especially from 1.1 to 2.0. The remaining conditions are the same as in the reaction to form intermediate polymer I. The conditions to assure that the intermediate polymer II is terminated with an amino group are analogous to those for intermediate polymer I.

Next, intermediate polymer II is reacted with a compound B having an ethylenically unsaturated reactive group to introduce an ethylenically unsaturated reactive group at each end of intermediate polymer II, obtaining a polymer of formula (III). This reaction may be carried out in the same manner as in the polymer of formula (II). This is also true for the reaction conditions under which at least some of the ethylenically unsaturated reactive groups being introduced will undergo polymerization.

As mentioned above, the polymers of formulae (II) and (III) are prepared through reaction between a diamine and a dihalide. Any desired ones of diamines and dihalides may be used as long as they can react in accordance with the above-illustrated schemes. It is understood that these intermediate polymers and final polymers are generally obtained as a mixture of oligomers having a degree of polymerization (n) of about 2 to 20 and polymers having a degree of polymerization (n) in excess of 20.

Preferred examples of the diamine compound used herein are given below.

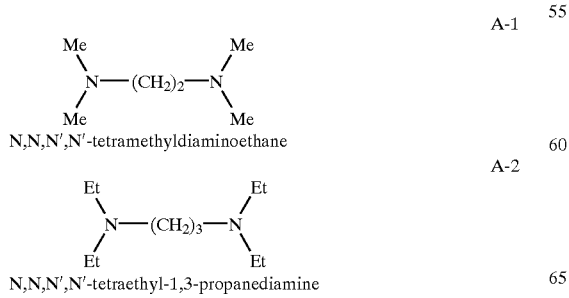

-continued

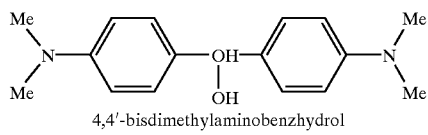
4,4'-bisdimethylaminobenzhydrol    A-14

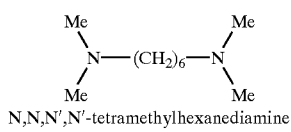
N,N,N',N'-tetramethylhexanediamine    A-15

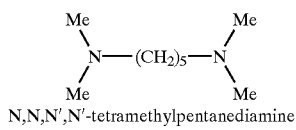
N,N,N',N'-tetramethylpentanediamine    A-16

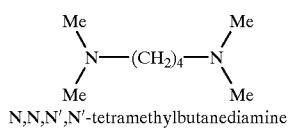
N,N,N',N'-tetramethylbutanediamine    A-17

Preferred examples of the dihalogen compound used herein are given below.

    B-1

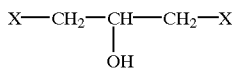    B-2

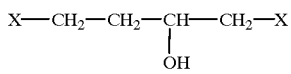    B-3

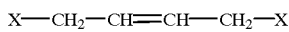    B-4

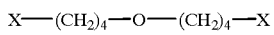    B-5

    B-6

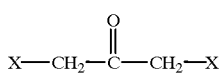    B-7

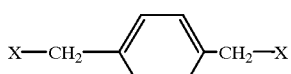    B-8

    B-9

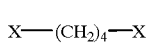    B-10

    B-11

    B-12

    B-13

    B-14

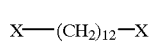    B-15

-continued

    B-16

In these examples, X is as defined previously, with chlorine and bromine atoms being preferred.

Examples of the intermediate polymers I and II to the polymers of formulae (II) and (III) are shown below as polymers resulting from combinations of the diamine and dihalogen compounds illustrated just above. Note that numerical values in the parentheses represent a molar ratio.

(1) Polymer resulting from a combination of A-16/B-10 (50/50)
(2) Polymer resulting from a combination of A-8/B-12/B-10 (50/48/2)
(3) Polymer resulting from a combination of A-8/B-13/B-10 (50/48/2)
(4) Polymer resulting from a combination of A-8/B-15/B-10 (50/48/2)
(5) Polymer resulting from a combination of A-16/B-2 (50/50)
(6) Polymer resulting from a combination of A-7/B-10 (50/50)
(7) Polymer resulting from a combination of A-2/B-10 (50/50)
(8) Polymer resulting from a combination of A-9/B-10 (50/50)
(9) Polymer resulting from a combination of A-16/B-9 (50/50)
(10) Polymer resulting from a combination of A-3/A-8/B-10 (2/48/50)
(11) Polymer resulting from a combination of A-14/A-16/B-17 (49/1/50)
(12) Polymer resulting from a combination of A-11/B-16 (50/50)
(13) Polymer resulting from a combination of A-6/B-4/B-15 (50/47/3)
(14) Polymer resulting from a combination of A-11/B-6 (50/50)
(15) Polymer resulting from a combination of A-13/B-3 (50/50)
(16) Polymer resulting from a combination of A-10/B-15 (50/50)
(17) Polymer resulting from a combination of A-15/B-16 (50/50)
(18) Polymer resulting from a combination of A-4/B-10 (50/50)
(19) Polymer resulting from a combination of A-10/B-12/B-10 (50/48/2)
(20) Polymer resulting from a combination of A-8/B-2 (50/50)
(21) Polymer resulting from a combination of A-7/A-16/B-10 (15/35/50)
(22) Polymer resulting from a combination of A-8/A-16/B-10 (15/35/50)
(23) Polymer resulting from a combination of A-9/A-16/B-10 (15/35/50)
(24) Polymer resulting from a combination of A-10/A-16/B-10 (15/35/50)
(25) Polymer resulting from a combination of A-8/B-13 (50/50)
(26) Polymer resulting from a combination of A-8/A-10/B-13 (15/35/50)

(27) Polymer resulting from a combination of A-8/B-13/B-10 (50/40/10)
(28) Polymer resulting from a combination of A-8/B-13/B-2 (50/40/10)
(29) Polymer resulting from a combination of A-9/B-13 (50/50)
(30) Polymer resulting from a combination of A-8/A-9/B-13 (25/25/50)
(31) Polymer resulting from a combination of A-9/A-10/B-13 (25/25/50)

The compounds A and B used in introducing ethylenically unsaturated reactive groups into intermediate polymers I and II at both ends are not critical as long as they have an ethylenically unsaturated reactive group such as an acryloyloxy, methacryloyloxy, acryloylimino, methacryloylimino, vinyl, allyl, diallylmethyl, allyloxy, diacryloylimino, and dimethacryloylimino group. Where intermediate polymers I and II as produced already have an ethylenically unsaturated reactive group as in the case of, for example, polymers (10), (11) and (13), they may be used as the (final) polymer in the practice of the invention without further reaction.

Preferred examples of compound A used in combination with intermediate polymer I are given below as E-1 to E-4.
E-1 $CH_2=CHCO_2C_2H_4NMe_2$
E-2 $CH_2=CHCONHC_3H_6NMe_2$

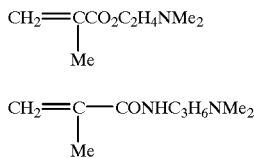

Preferred examples of compound B used in combination with intermediate polymer II are given below as F-1 to F-5.
F-1 $CH_2=CHOCH_2CH_2X$

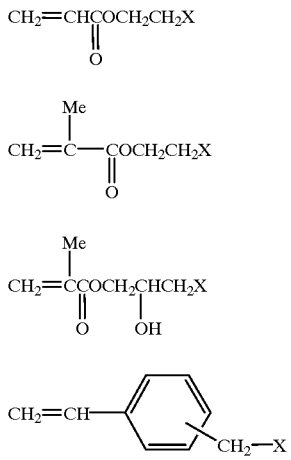

In the formulae of E-1 to E-4 and F-1 to F-5, Me is methyl and X is halogen as defined above.

In the practice of the invention, the polymers of formula (I), preferably formulae (II) and (III) are generally used alone although a mixture of two or more polymers may be used.

The humidity sensitive thin film used herein contains a crosslinked product of a polymer of formula (I), preferably formula (II) or (III) as previously described. The thin film is preferably formed by the following procedure. First a coating solution containing a polymer of formula (I), preferably formula (II) or (III) is prepared. Since the polymer is ionic and thus readily dissolvable in such solvents as water and alcohols, the solvent for the coating solution may be any of the solvents in which the polymer is soluble. Among others, water, methanol, ethanol, isopropyl alcohol, 2-methoxyethanol and 2-ethoxyethanol are preferred from the considerations of solubility, the storage stability of the coating solution, and ease of handling. At this point, a polymerization initiator, for example, 0.03 to 0.7% by weight of a benzophenone compound is preferably added to the solution so that the resulting coating is ready for crosslinking by subsequent exposure to radiation, typically ultraviolet radiation.

The coating solution is applied, preferably by coating, onto the undercoat layer on the insulating substrate having electrodes formed thereon to thereby form a humidity sensitive thin film. For the coating purpose, well-known techniques such as dipping, brush coating, gravure coating, screen printing, and spin coating techniques are useful. Any desired one of these coating techniques may be chosen depending on the overall procedure and the type and application of a final product.

After the coating is formed in this way, it is dried at a temperature of about 15 to 100° C. for about 3 to 15 minutes. Thereafter the coating or polymer is crosslinked, preferably by exposure to radiation, especially ultraviolet radiation. Crosslinking by exposure to ultraviolet radiation may be carried out by any well-known technique. Often ultraviolet radiation having an intensity of at least about 50 mW/cm$^2$ is irradiated in a dose of about 200 to 2,500 mJ/cm$^2$. Conventional light sources such as mercury lamps may be used as the ultraviolet source.

The humidity sensitive thin film as crosslinked preferably has a thickness of about 0.1 to 20 μm, especially about 0.5 to 10 μm. Outside this range, a thicker film would be slow in response of its electric resistance to humidity whereas a thinner film would produce lower outputs in the low humidity region and be less resistant to gases and water.

In the practice of the invention, a water-repellent coating may be formed on the humidity sensitive thin film in order to prevent any influence of water droplets adhering to the sensor for thereby insuring quick accurate humidity measurement. The water-repellent coating preferably has a contact angle with water of at least 90°, especially 90° to 130° and a sufficient thickness to allow for moisture penetration, typically up to 5 μm, especially 0.01 to 1 μm.

The material of which the water-repellent coating is constructed includes hydrophobic polymers, for example, fluorinated polymers such as polytetrafluoroethylene, olefinic polymers such as polyethylene and polypropylene, and silicone polymers. The water-repellent coating may be formed by any desired technique, typically by dissolving the material in a suitable solvent such as saturated carbon fluoride and coating the solution.

As long as the humidity sensor device of the invention includes the above-mentioned undercoat layer and humidity sensitive thin film on an insulating substrate having electrodes formed thereon, the remaining construction is not critical.

Referring to FIG. 1, there is illustrated in plan view one exemplary arrangement of the humidity sensor device.

The humidity sensor 1 includes a pair of interdigital or comb-shaped electrodes 4 on an insulating substrate 2. The pair of comb-shaped electrodes 4 are disposed on the substrate 2 and interdigitated with each other to define a gap 5 of a certain distance therebetween. The gap typically has a distance of about 100 to 500 μm. An undercoat layer 11 is formed over the insulating substrate 2 and comb-shaped electrodes 4, and a humidity sensitive thin film 3 is formed thereon. The comb-shaped electrodes 4 are provided at one end with electrode tabs 6 to which leads 7 are connected with solder welds 8. A resist film 9 is formed for preventing diffusion of the electrode material.

In detecting humidity in the surrounding atmosphere, voltage, preferably AC voltage is applied across the electrodes 4. Since the humidity sensitive thin film 3 changes its electrical resistance or impedance in accordance with the humidity, the output voltage changes therewith, in terms of which the humidity is detectable. The applied voltage is typically up to about 12 volts.

The insulating substrate 2 used herein may be formed of any desired material which is electrically insulating and well receptive to the electrodes 4 and undercoat layer 11. Useful substrates are glass, plastics, ceramics and metals coated with insulating material.

The electrodes 4 may be made of any conventional electrode material. For example, they are formed by screen printing low resistance paste containing Au or $RuO_2$ and optionally glass frit, followed by high temperature firing. The electrode tabs 6 may be made of any conventional material which is compatible with the solder 8. For example, Ag—Pd alloy is printed in a conventional manner and baked at high temperatures to form the electrode tabs 6. Where gold is used as the electrodes 4, it is preferred that the resist film 9 of resist or glass is further provided in order to prevent diffusion of Au during soldering. No limits are imposed on the thickness and configuration of the resist film 9 as long as it is effective for preventing diffusion of Au during soldering.

The humidity sensor of the present invention is not limited to the illustrated embodiment. Any desired shape or arrangement may be employed.

EXAMPLE

Examples of the present invention are given below by way of illustration and not by way of limitation.

Example 1

According to the first reaction scheme, 8.6 g (0.05 mol) of N,N,N',N'-tetramethyl-1,6-diaminohexane and 14.4 g (0.06 mol) of 1,12-dichlorododecane were dissolved in 20 g of methanol and stirred for 96 hours at the reflux temperature, effecting quaternization reaction to form an intermediate polymer as shown in reaction formula (1) below. Then 10.2 g (0.06 mol) of N-(3-dimethylaminopropyl)methacrylamide and 0.2 g of m-dinitrobenzene as a polymerization inhibitor were added to the reaction solution. The solution was stirred at 35° C. for 100 hours, introducing a reactive group into the intermediate polymer at its end as shown in reaction formula (2) below.

reaction formula (1)

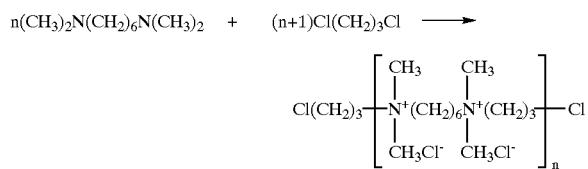

reaction formula (2)

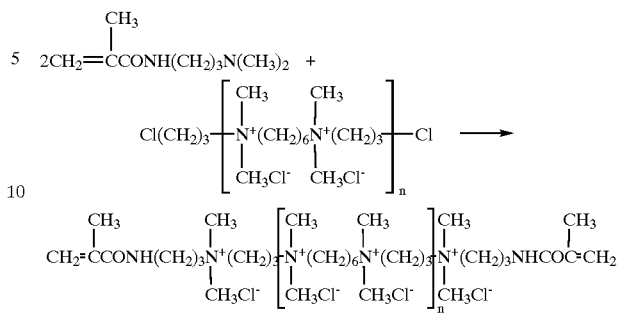

The reaction solution was added dropwise to a large volume of acetone whereupon the polymer precipitated. The precipitate was collected by filtration and then dried in vacuum. After precipitation and purification of the polymer in this way, a 2-ethoxymethanol solution containing 5% by weight of the polymer was prepared. To the solution 0.02% by weight of Irgacure 184 (commercially available from Ciba Specialty Chemicals) was added as a polymerization initiator to complete a coating solution. Note that the polymer had Mn of about 5,000 prior to crosslinking.

A humidity sensor 1 as shown in FIG. 1 was fabricated. A porous ceramic substrate of alumina was used as the insulating substrate 2. Comb-shaped electrodes 4 were formed on the substrate by screen printing paste containing $RuO_2$ and glass frit and firing at high temperature. The interdigital electrodes defined a gap of about 225 μm wide therebetween.

On the insulating substrate having electrodes formed thereon, 0.8 μl of an aqueous solution containing 1 wt % of vinyltrimethoxysilane (KBM1003 by Shin-Etsu Chemical Co., Ltd.) and 1 wt % of acetic acid was added dropwise, followed by air drying. The coating was washed with methanol and heat treated at 120° C. for 10 minutes, forming an undercoat layer 11.

The coating solution was coated onto the undercoat layer 11 on the insulating substrate 2 by dispensing an aliquot of 1.5 μl and then dried at room temperature for 30 minutes, forming a polymer coating. In a nitrogen atmosphere, the coatings on the electrode-bearing surface and the rear surface of the substrate were exposed to ultraviolet radiation for 5 minutes on each surface, causing the polymer to crosslink. The dose of ultraviolet radiation was 25,000 mJ/cm². The resulting humidity sensitive thin film 3 had a thickness of 3 μm.

The humidity sensor thus fabricated was evaluated for output and examined by a water resistance test.

For evaluating the output, a divided flow humidity generating machine model SRH-1 (manufactured by Shinei K. K.) was used. The humidity sensor was incorporated in the circuit described and shown in JP-A 2-123843. The humidity sensor incorporated in the circuit was set in the humidity generating machine where the relative humidity was changed stepwise from a low level to a high level and then from the high level to the low level both at 25° C. During the humidity cycling process, the humidity sensor which was allowed to stand at a selected relative humidity for 10 minutes was measured for output voltage. The selected relative humidity levels were RH 0%, RH 10%, RH 20%, RH 30%, RH 50%, RH 70%, and RH 90%. The results are plotted in FIG. 2.

Figure 3:
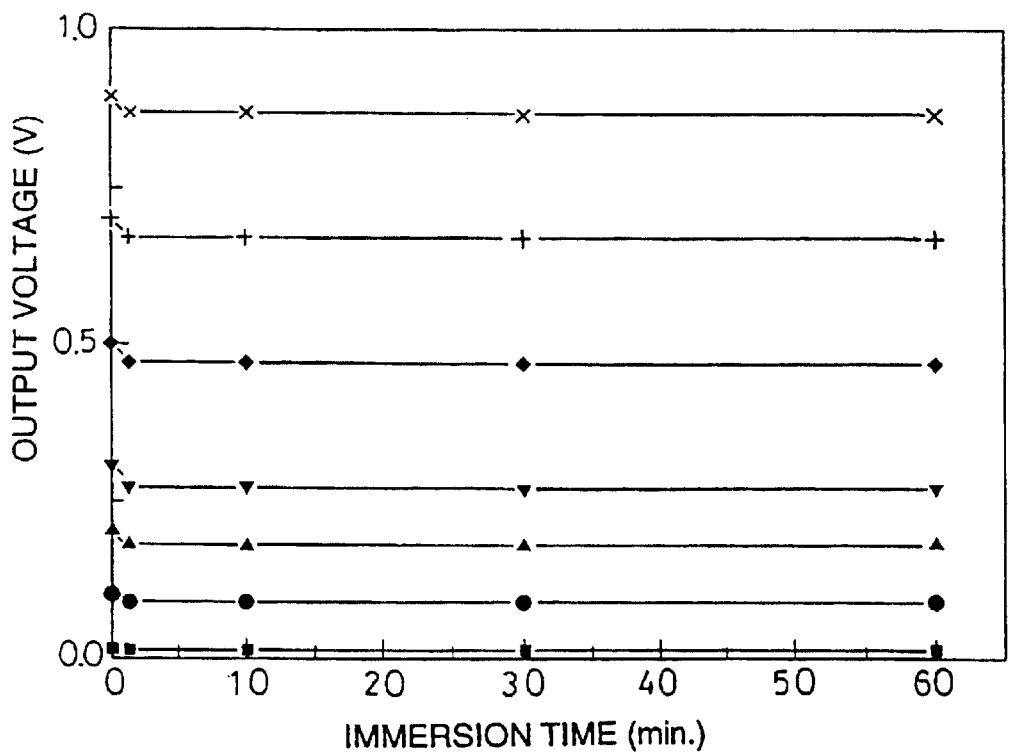
FIG. 3 is a graph showing the water resistance of the humidity sensor of Example 1.

In the water resistance test, the humidity sensor having undergone humidity cycling for output voltage monitoring as mentioned above was immersed in distilled water for 1 minute, dried in air, and measured for output voltage again, which was compared with the initial output voltage (prior to water immersion). The time duration when the humidity sensor was immersed in distilled water was prolonged to 10 minutes, 30 minutes and 60 minutes whereupon the output voltage was similarly measured. The results are plotted in FIG. 3.

Figure 2:
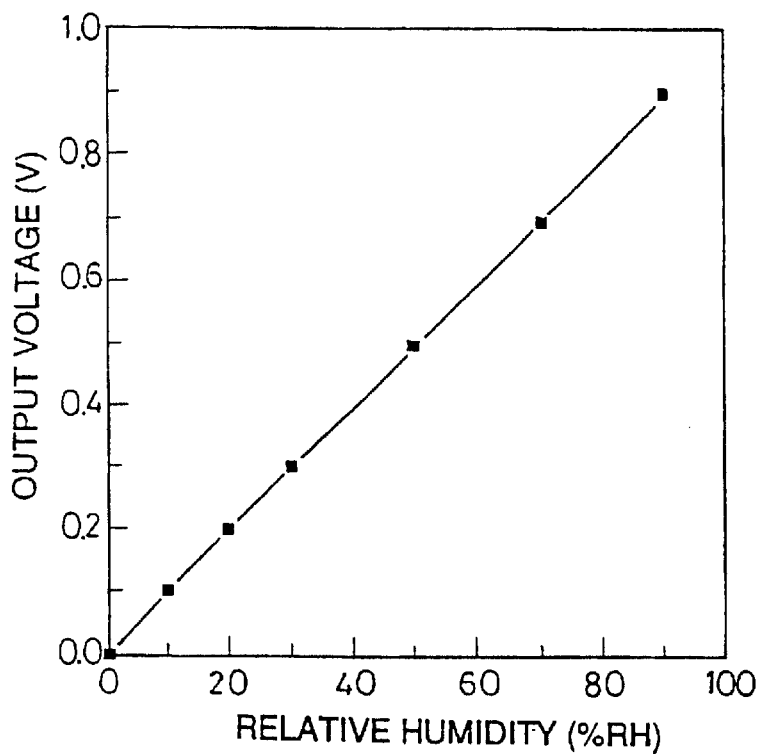
FIG. 2 is a graph showing the output voltage versus relative humidity of the humidity sensor of Example 1.

It is evident from FIG. 2 that the inventive humidity sensor exhibits no hysteresis and is able to measure low humidity, especially in a region of RH 10% or lower. It is evident from FIG. 3 that the inventive humidity sensor is fully resistant to water. The advantages of the present invention are thus demonstrated.

Example 2

8.6 g (0.05 mol) of N,N,N',N'-tetramethyl-1,6-diaminohexane and 7.7 g (0.06 mol) of 1,3-dichloro-2-propanol were dissolved in 8.1 g of isopropanol and stirred for 50 hours at the reflux temperature, effecting quaternization reaction to form an intermediate polymer. Then 10.2 g (0.06 mol) of N-(3-dimethylaminopropyl)methacrylamide and 0.2 g of m-dinitrobenzene as a polymerization inhibitor were added to the reaction solution. The solution was stirred at 45° C. for 120 hours, introducing a reactive group into the intermediate polymer at its end. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 110,000 prior to crosslinking.

Figure 4:
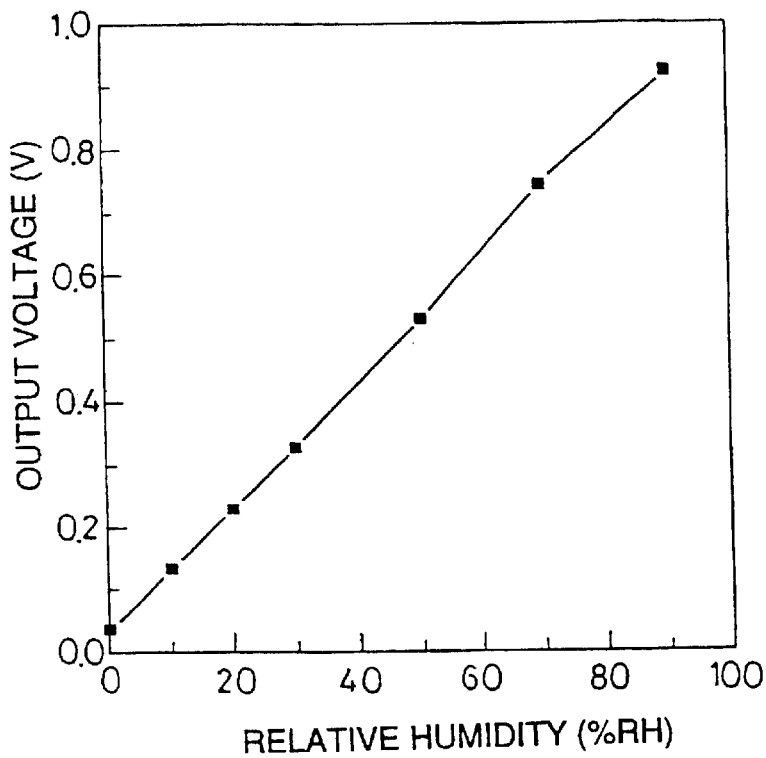
FIGS. 4 and 5 are graphs showing the output and water resistance of the sensor of Example 2, respectively.
Figure 5:
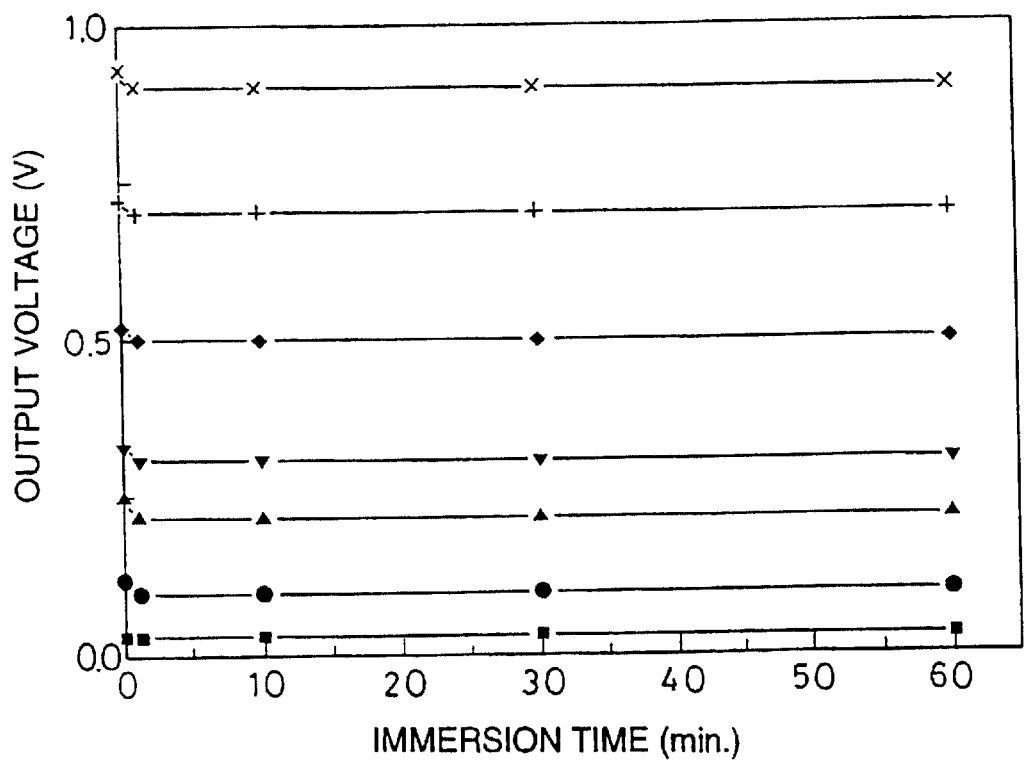

The humidity sensor was evaluated for output and examined by the water resistance test as in Example 1. FIG. 4 shows plots of output voltage versus relative humidity and FIG. 5 shows the results of the water resistance test. The advantages of the present invention are evident from FIGS. 4 and 5.

Example 3

5.6 g (0.05 mol) of 1,4-diazabicyclo[2.2.2]octane and 7.1 g (0.05 mol) of 1,5-dichloropentane were dissolved in 6.4 g of 2-ethoxyethanol and stirred for 60 hours at the reflux temperature, effecting quaternization reaction. The reaction solution was added dropwise to a large volume of acetone whereupon the product was precipitated and purified. The product and 2.3 g (0.02 mol) of 1,3-dichloropropane were dissolved in 6.4 g of 2-ethoxyethanol. The reaction solution was stirred for 20 hours at the reflux temperature, effecting quaternization reaction again to form an intermediate polymer. It was similarly precipitated and purified. There were added 10.2 g (0.06 mol) of N-(3-dimethylaminopropyl) methacrylamide and 0.2 g of m-dinitrobenzene as a polymerization inhibitor. The solution was stirred at 45° C. for 120 hours, introducing a reactive group into the intermediate polymer at its end. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 90,000 prior to crosslinking.

Figure 6:
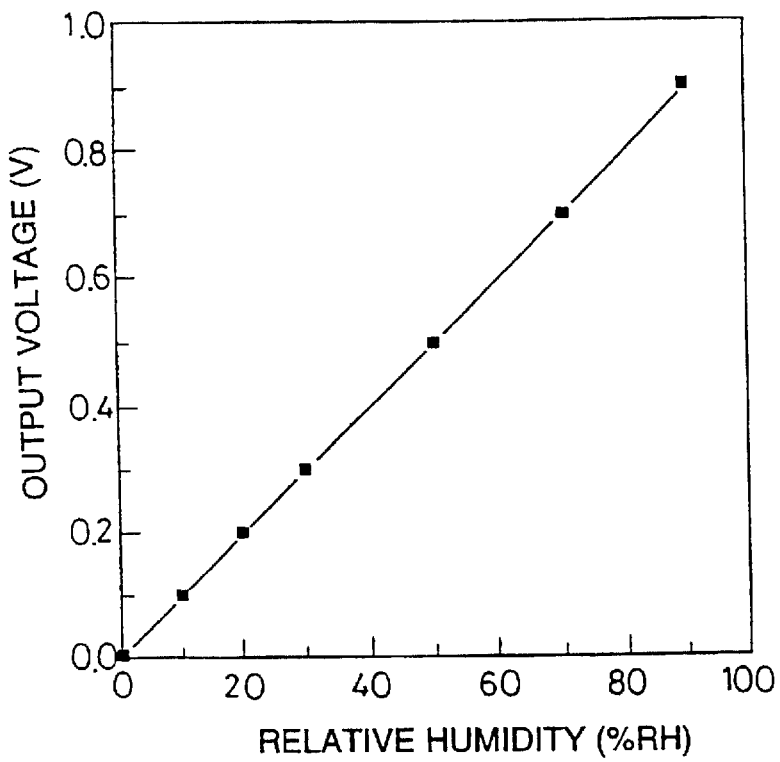
FIGS. 6 and 7 are graphs showing the output and water resistance of the sensor of Example 3, respectively.
Figure 7:
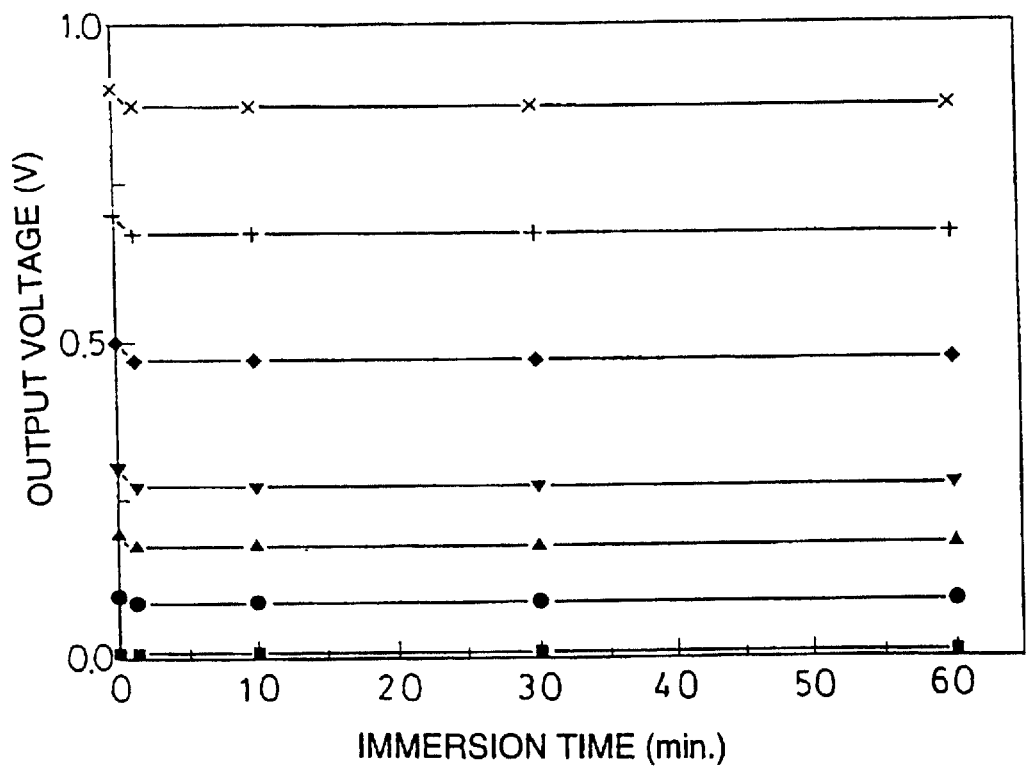

The humidity sensor was evaluated for output and examined by the water resistance test as in Example 1. FIG. 6 shows plots of output voltage versus relative humidity and FIG. 7 shows the results of the water resistance test. The advantages of the present invention are evident from FIGS. 6 and 7.

Example 4

9.9 g (0.05 mol) of 1,3-di(4-pyridyl)propane and 6.8 g (0.06 mol) of 1,3-dichloropropane were dissolved in 8.8 g of 2-ethoxyethanol and stirred for 75 hours at the reflux temperature, effecting quaternization reaction to form an intermediate polymer. Then 10.2 g (0.06 mol) of N-(3-dimethylaminopropyl) methacrylamide and 0.2 g of m-dinitrobenzene as a polymerization inhibitor were added to the reaction solution. The solution was stirred at 45° C. for 120 hours, introducing a reactive group into the intermediate polymer at its end. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 80,000 prior to crosslinking.

Figure 8:
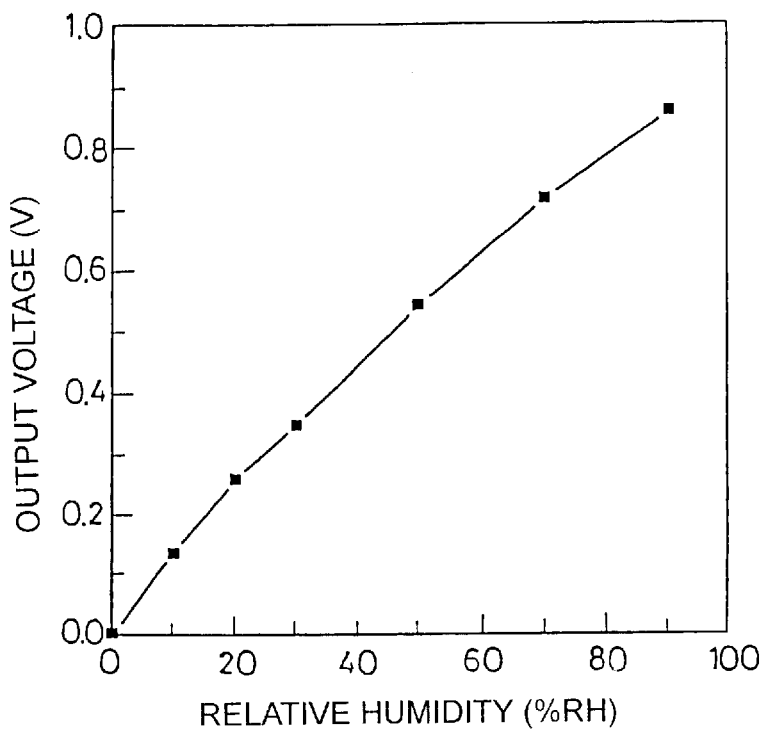
FIGS. 8 and 9 are graphs showing the output and water resistance of the sensor of Example 4, respectively.
Figure 9:
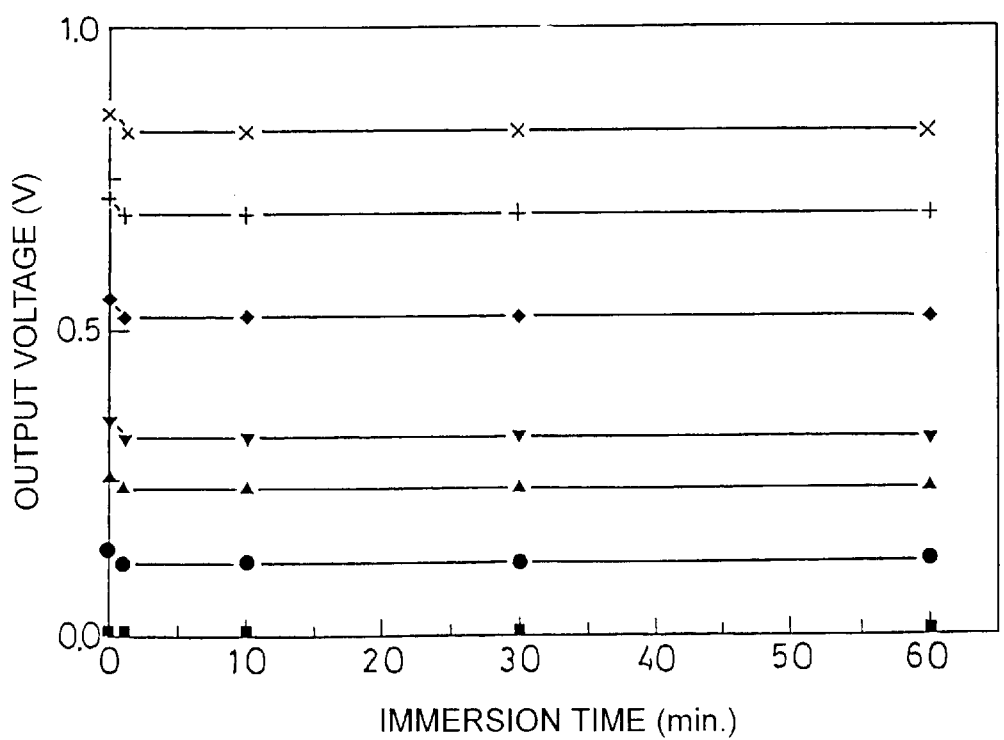

The humidity sensor was evaluated for output and examined by the water resistance test as in Example 1. FIG. 8 shows plots output voltage versus relative humidity and FIG. 9 shows the results of the water resistance test. The advantages of the present invention are evident from FIGS. 8 and 9.

Example 5

9.3 g (0.05 mol) of N,N,N',N'-tetraethyl-1,3-diaminopropane and 6.8 g (0.06 mol) of 1,3-dichloropropane were dissolved in 8.5 g of 2-ethoxyethanol and stirred for 60 hours at the reflux temperature, effecting quaternization reaction to form an intermediate polymer. Then 10.2 g (0.06 mol) of N-(3-dimethylaminopropyl) methacrylamide and 0.2 g of m-dinitrobenzene as a polymerization inhibitor were added to the reaction solution. The solution was stirred at 45° C. for 120 hours, introducing a reactive group into the intermediate polymer at its end. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 80,000 prior to crosslinking.

Figure 10:
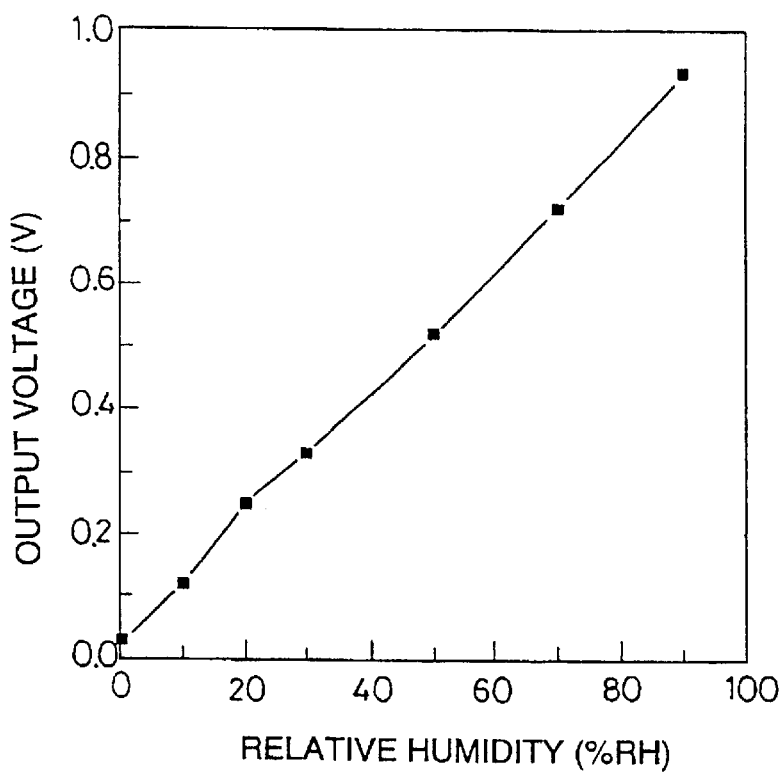
FIGS. 10 and 11 are graphs showing the output and water resistance of the sensor of Example 5, respectively.
Figure 11:
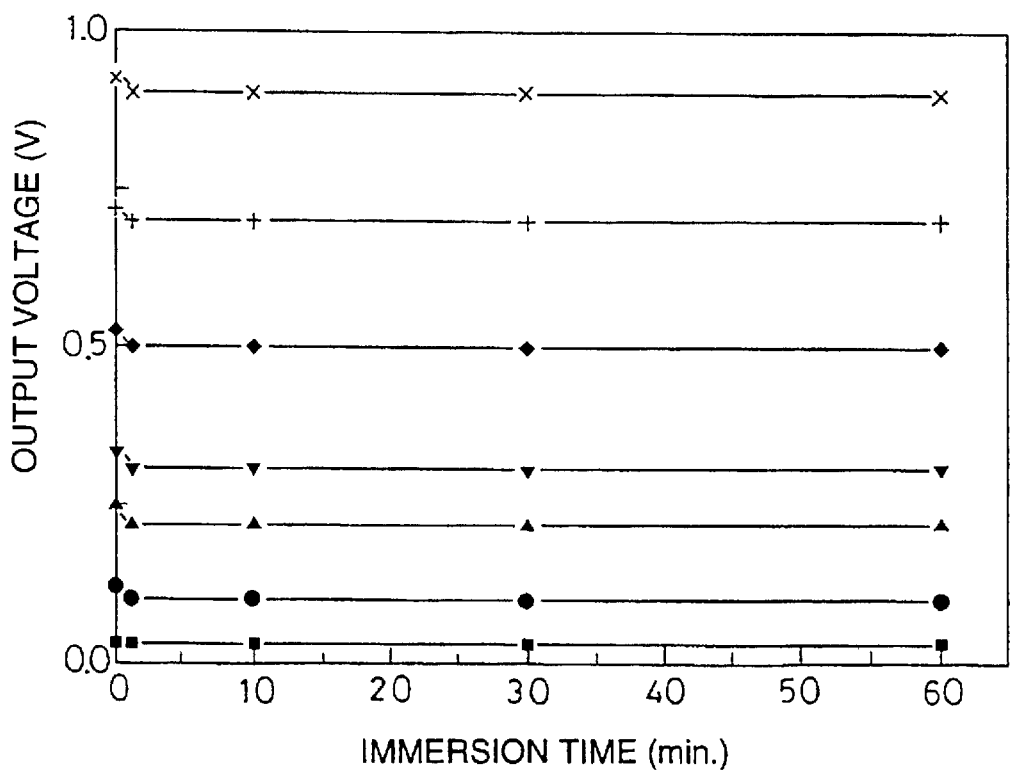

The humidity sensor was evaluated for output and examined by the water resistance test as in Example 1. FIG. 10 shows plots of output voltage versus relative humidity and FIG. 11 shows the results of the water resistance test. The advantages of the present invention are evident from FIGS. 10 and 11.

Example 6

5.7 g (0.05 mol) of N,N'-dimethylpiperazine and 6.8 g (0.06 mol) of 1,3-dichloropropane were dissolved in 6.7 g of 2-ethoxyethanol and stirred for 60 hours at the reflux temperature, effecting quaternization reaction to form an intermediate polymer. Then 10.2 g (0.06 mol) of N-(3-dimethylaminopropyl) methacrylamide and 0.2 g of m-dinitrobenzene as a polymerization inhibitor were added to the reaction solution. The solution was stirred at 45° C. for 120 hours, introducing a reactive group into the intermediate polymer at its end. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 100,000 prior to crosslinking.

Figure 12:
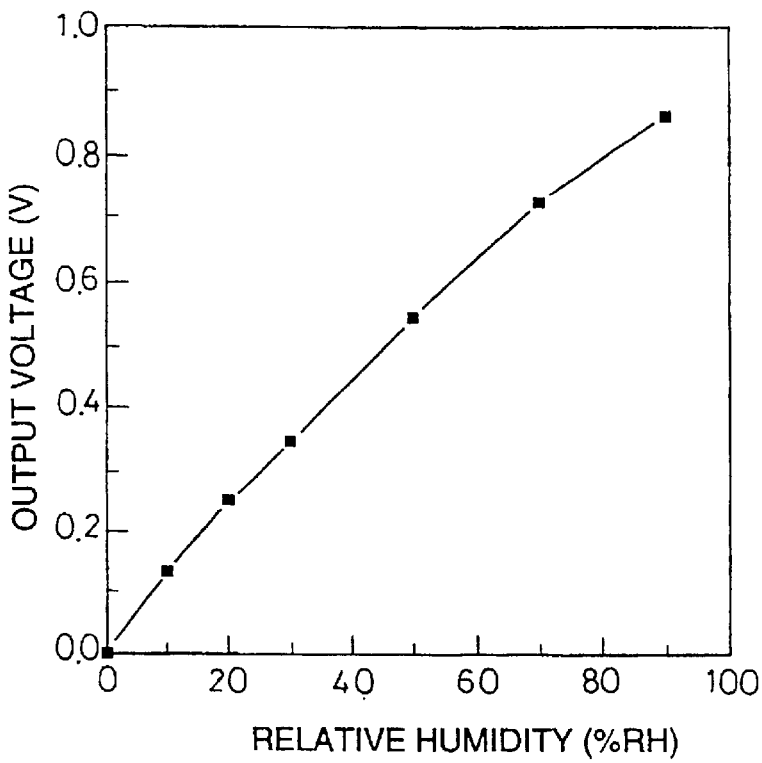
FIGS. 12 and 13 are graphs showing the output and water resistance of the sensor of Example 6, respectively.
Figure 13:
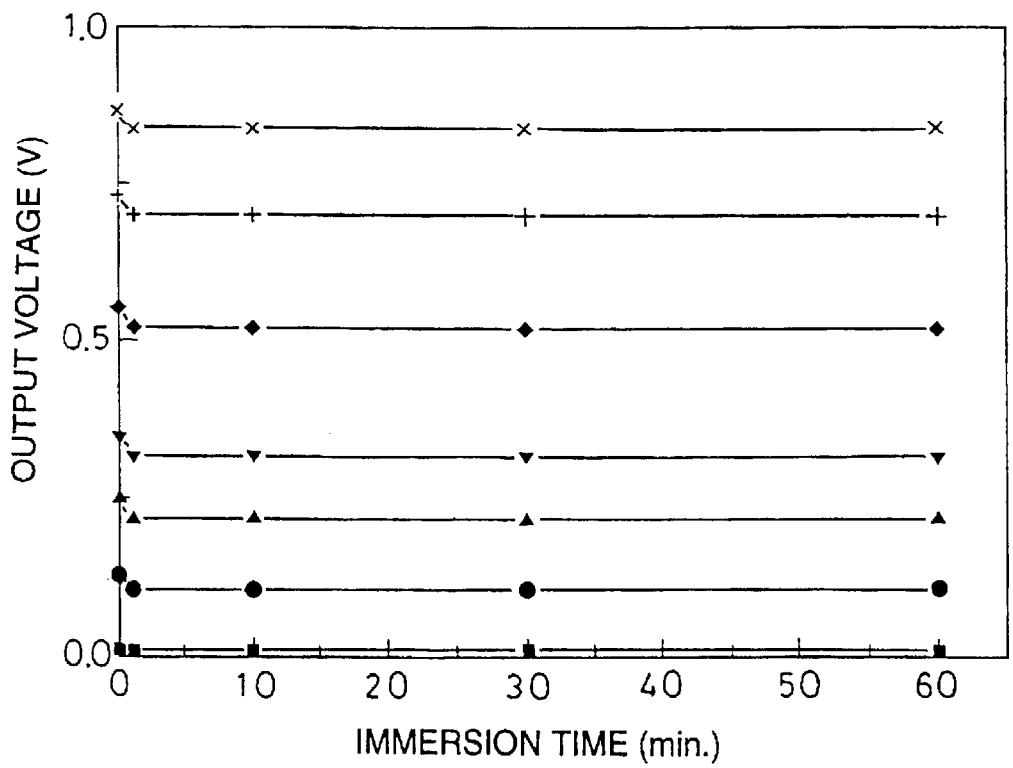

The humidity sensor was evaluated for output and examined by the water resistance test as in Example 1. FIG. 12 shows plots of output voltage versus relative humidity and FIG. 13 shows the results of the water resistance test. The advantages of the present invention are evident from FIGS. 12 and 13.

Example 7

8.6 g (0.05 mol) of N,N,N',N'-tetramethyl-1,6-diaminohexane and 10.5 g (0.06 mol) of α,α'-dichloro-p-xylene were dissolved in 9.6 g of 2-ethoxyethanol and stirred for 70 hours at the reflux temperature, effecting quaternization reaction to form an intermediate polymer. Then 10.2 g (0.06 mol) of N-(3-dimethylaminopropyl) methacrylamide and 0.2 g of m-dinitrobenzene as a polymerization inhibitor were added to the reaction solution. The solution was stirred at 45° C. for 120 hours, introducing a reactive group into the intermediate polymer at its end. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 80,000 prior to crosslinking.

Figure 14:
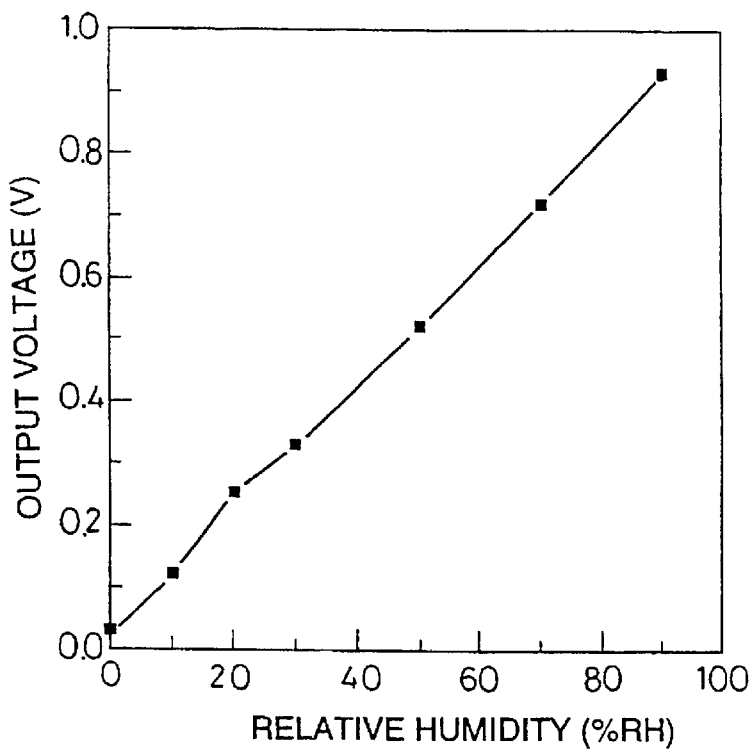
FIGS. 14 and 15 are graphs showing the output and water resistance of the sensor of Example 7, respectively.
Figure 15:
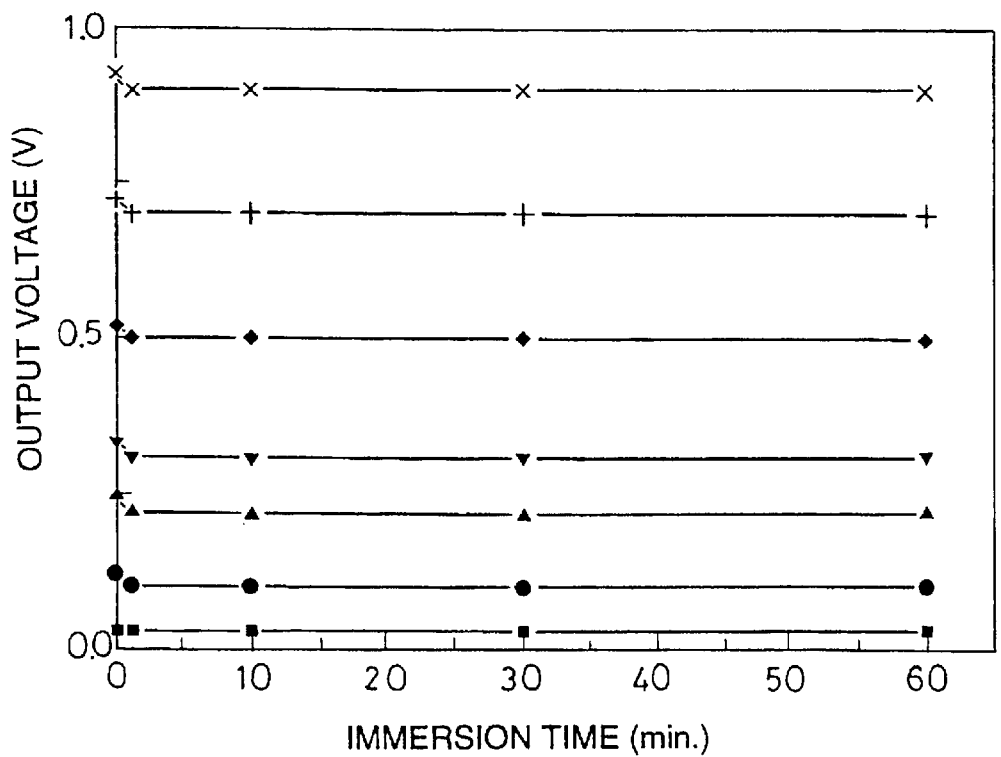

The humidity sensor was evaluated for output and examined by the water resistance test as in Example 1. FIG. 14 shows plots of output voltage versus relative humidity and FIG. 15 shows the results of the water resistance test. The advantages of the present invention are evident from FIGS. 14 and 15.

Example 8

0.36 g (0.0025 mol) of N,N,N',N'-tetramethyl-2-butene-1,4-diaminobutane, 5.3 g (0.048 mol) of 1,4-diazabicyclo [2.2.2]octane, and 5.7 g (0.05 mol) of 1,3-dichloropropane were dissolved in 7.4 g of ethanol and stirred for 70 hours at the reflux temperature, effecting quaternization reaction. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 80,000 prior to crosslinking.

Figure 16:
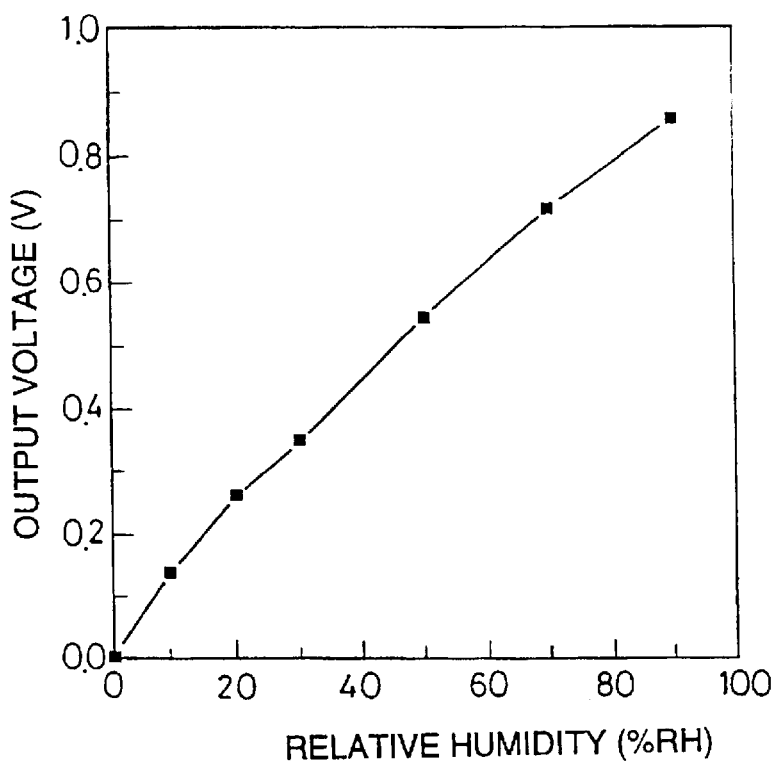
FIGS. 16 and 17 are graphs showing the output and water resistance of the sensor of Example 8, respectively.
Figure 17:
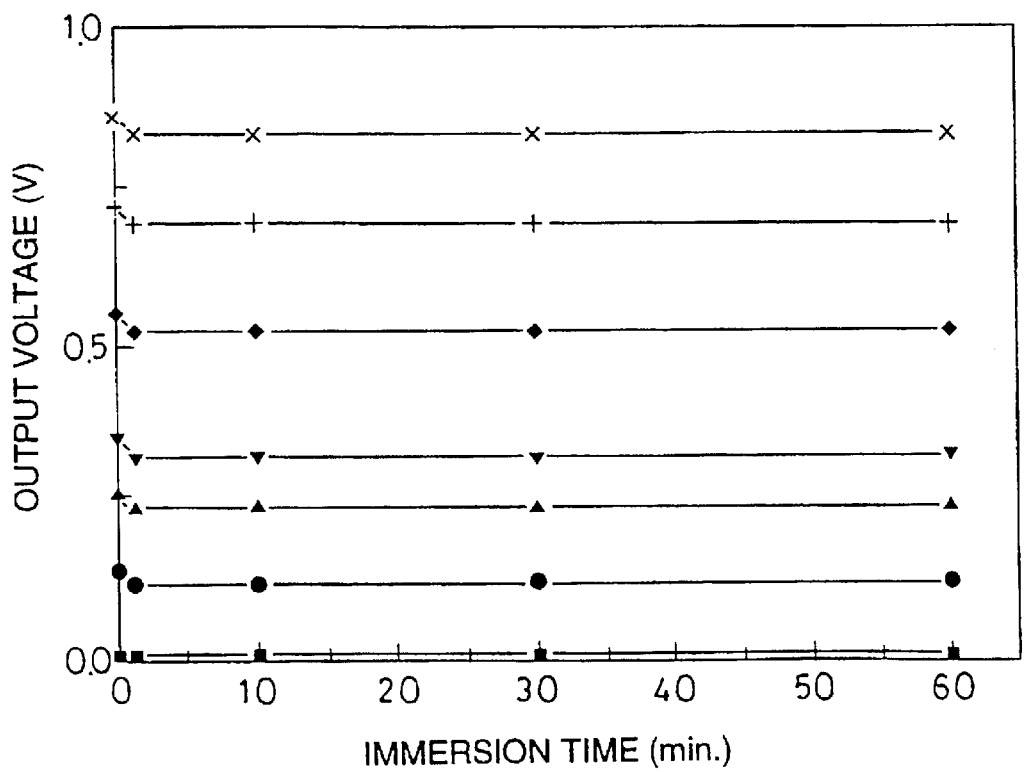

The humidity sensor was evaluated for output and examined by the water resistance test as in Example 1. FIG. 16 shows plots of output voltage versus relative humidity and FIG. 17 shows the results of the water resistance test. The advantages of the present invention are evident from FIGS. 16 and 17.

Example 9

8.6 g (0.05 mol) of N,N,N',N'-tetramethyl-1,6-diaminohexane and 12.1 g (0.06 mol) of 1,3-dibromopropane were dissolved in 10.9 g of methanol and stirred for 10 hours at the reflux temperature, effecting quaternization reaction to form an intermediate polymer. Then 9.36 g (0.06 mol) of N-(3-dimethylaminopropyl) acrylamide and 0.4 g of m-dinitrobenzene as a polymerization inhibitor were added to the reaction solution. The solution was stirred at 35° C. for 100 hours, introducing a reactive group into the intermediate polymer at its end. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 150,000 prior to crosslinking.

Figure 18:
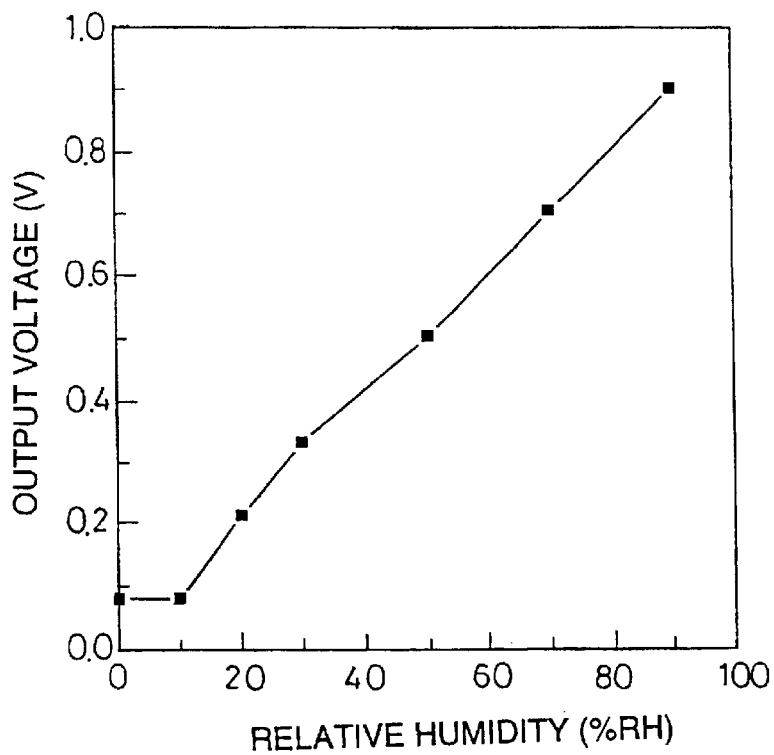
FIGS. 18 and 19 are graphs showing the output and water resistance of the sensor of Example 9, respectively.
Figure 19:
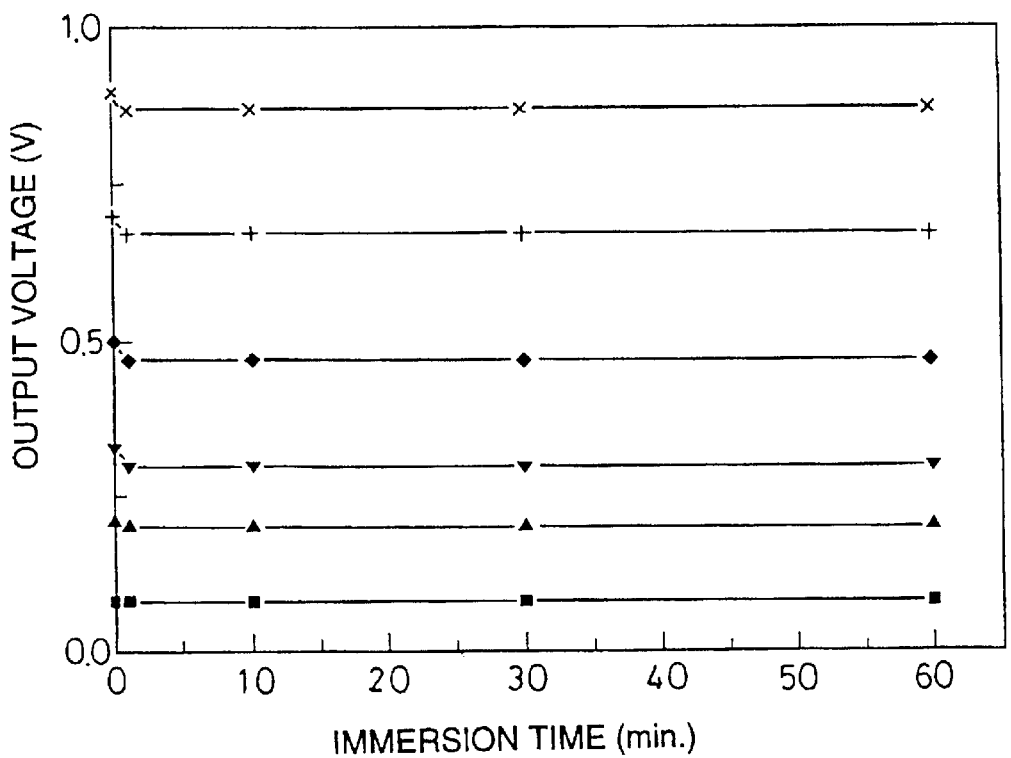

The humidity sensor was evaluated for output and examined by the water resistance test as in Example 1. FIG. 18 shows plots of output voltage versus relative humidity and FIG. 19 shows the results of the water resistance test. It is seen from FIG. 18 that this sensor enabled humidity measurement over a relatively wide region although measurement was impossible in the region of RH 0% through 10% because the dibromo compound was used as the dihalogen compound. The sensor had improved water resistance as seen from FIG. 19.

Example 10

5.6 g (0.05 mol) of 1,4-diazabicyclo[2.2.2]octane and 13.1 g (0.06 mol) of 1,3-dibromo-2-propanol were dissolved in 9.4 g of 2-ethoxyethanol and stirred for 30 hours at the reflux temperature, effecting quaternization reaction to form an intermediate polymer. Then 10.2 g (0.06 mol) of N-(3-dimethylaminopropyl) methacrylamide and 0.4 g of m-dinitrobenzene as a polymerization inhibitor were added to the reaction solution. The solution was stirred at 35° C. for 100 hours, introducing a reactive group into the intermediate polymer at its end. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 130,000 prior to crosslinking.

Figure 20:
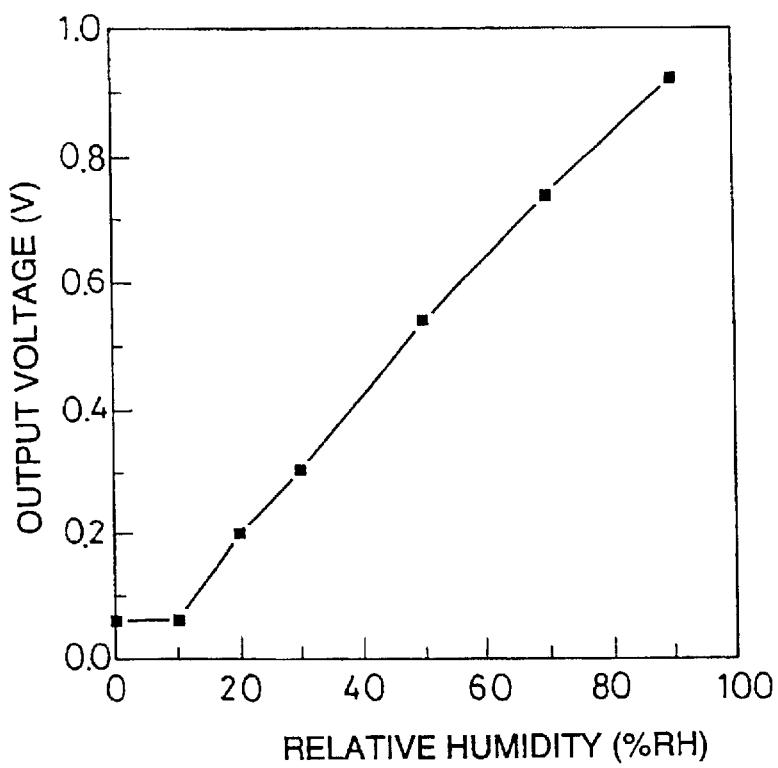
FIGS. 20 and 21 are graphs showing the output and water resistance of the sensor of Example 10, respectively.
Figure 21:
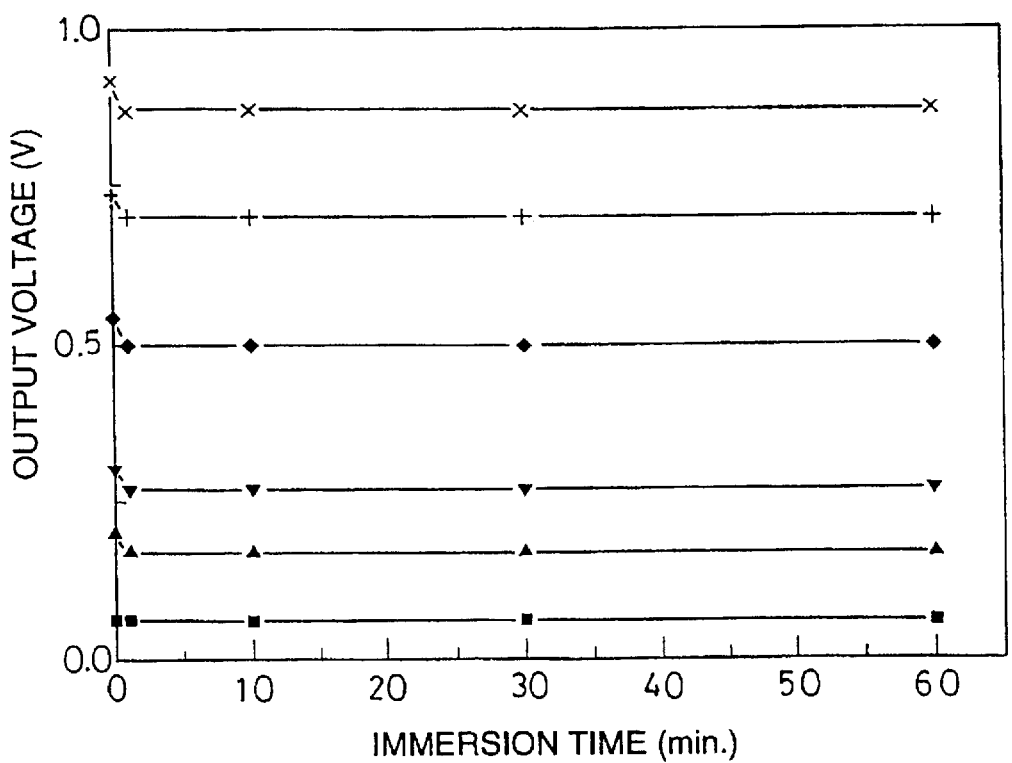

The humidity sensor was evaluated for output and examined by the water resistance test as in Example 1. FIG. 20 shows plots of output voltage versus relative humidity and FIG. 21 shows the results of the water resistance test. FIGS. 20 and 21 show that the results are the same as in Example 9.

Example 11

According to the second reaction scheme, 10.3 g (0.06 mol) of N,N,N',N'-tetramethyl-1,6-diaminohexane and 5.7 g (0.05 mol) of 1,3-dichloropropane were dissolved in 8.0 g of methanol and stirred for 25 hours at the reflux temperature, effecting quaternization reaction to form an intermediate polymer as shown in reaction formula (3) below. Then 6.4 g (0.06 mol) of 2-chloroethyl vinyl ether and 0.2 g of m-dinitrobenzene as a polymerization inhibitor were added to the reaction solution. The solution was stirred at 35° C. for 100 hours, introducing a reactive group into the intermediate polymer at its end as shown in reaction formula (4) below. Note that the polymer had Mn of about 110,000 prior to crosslinking.

reaction formula (3)

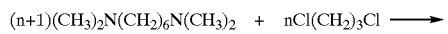

$(n+1)(CH_3)_2N(CH_2)_6N(CH_3)_2 + nCl(CH_2)_3Cl \longrightarrow$

-continued

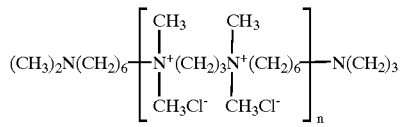

reaction formula (4)

2CH₂=CH—O—(CH₂)₂Cl +

(CH₃)₂N(CH₂)₆—[N⁺(CH₃)—(CH₂)₃—N⁺(CH₃)—(CH₂)₆]ₙ—N(CH₃)₂  (with CH₃Cl⁻ counterions) →

CH₂=CH—O—(CH₂)₂—[N⁺(CH₃)(CH₃Cl⁻)(CH₂)₆—N⁺(CH₃)(CH₃Cl⁻)—(CH₂)₃]ₙ—N⁺(CH₃)(CH₃Cl⁻)(CH₂)₆—N⁺(CH₃)(CH₃Cl⁻)—(CH₂)₂O—CH=CH₂

A humidity sensor was fabricated as in Example 1 and similarly evaluated for output and water resistance. The results were equivalent to those of Example 1.

Example 12

0.82 g (0.0025 mol) of N,N,N',N'-tetraallyl-1,4-diaminobutane, 5.3 g (0.048 mol) of 1,4-diazabicyclo[2.2.2]octane, and 5.7 g (0.05 mol) of 1,3-dichloropropane were dissolved in 7.4 g of ethanol and stirred for 70 hours at the reflux temperature, effecting quaternization reaction. The resulting polymer was precipitated and purified. Except that this polymer was used as a conductive component, a humidity sensor was fabricated as in Example 1 by preparing a coating solution of the polymer and coating it to form a humidity sensitive thin film. Note that the polymer had Mn of about 110,000 prior to crosslinking.

Figure 22:
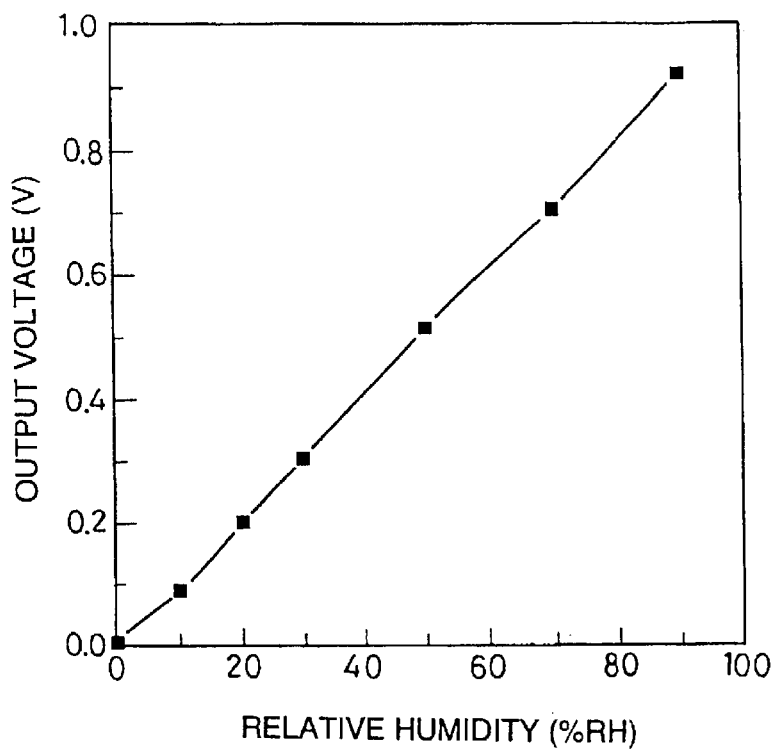
FIGS. 22 and 23 are graphs showing the output and water resistance of the sensor of Example 12, respectively.
Figure 23:
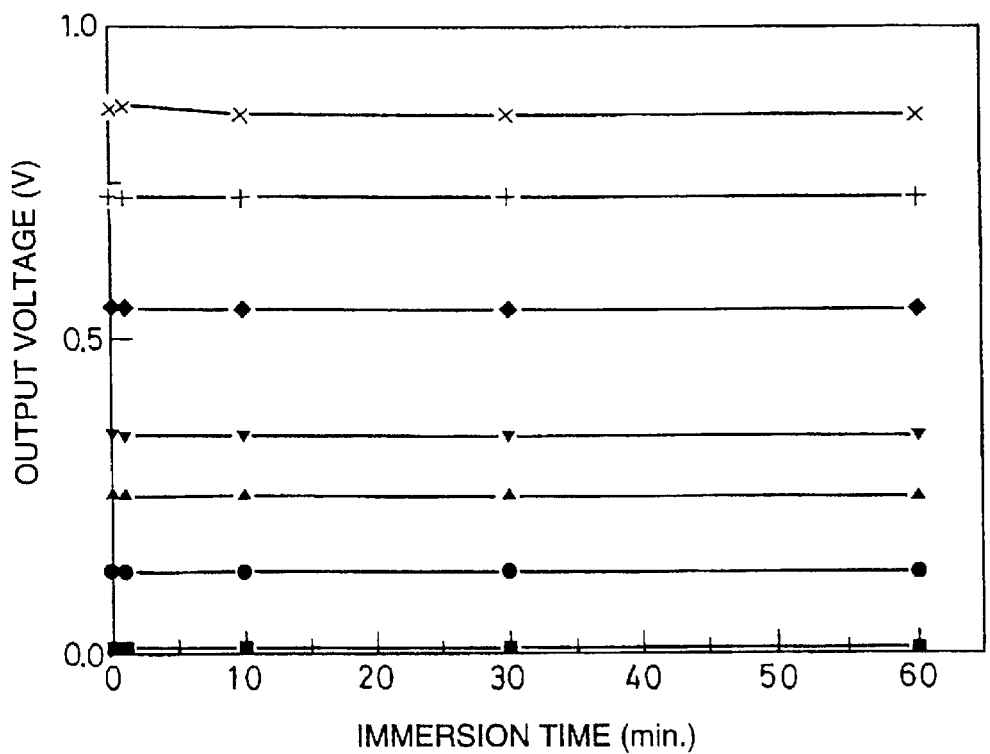

The humidity sensor was evaluated for output and examined by the water resistance test as in Example 1. FIG. 22 shows plots of output voltage versus relative humidity and FIG. 23 shows the results of the water resistance test. The advantages of the present invention are evident from FIGS. 22 and 23.

Example 13

A humidity sensor was fabricated as in Example 1 except that in introducing a reactive group into the intermediate polymer at its end, the reaction solution was stirred for 20 hours at the reflux temperature instead of stirring for 100 hours at 35° C. Note that the polymer had Mn of about 130,000 prior to crosslinking.

Figure 24:
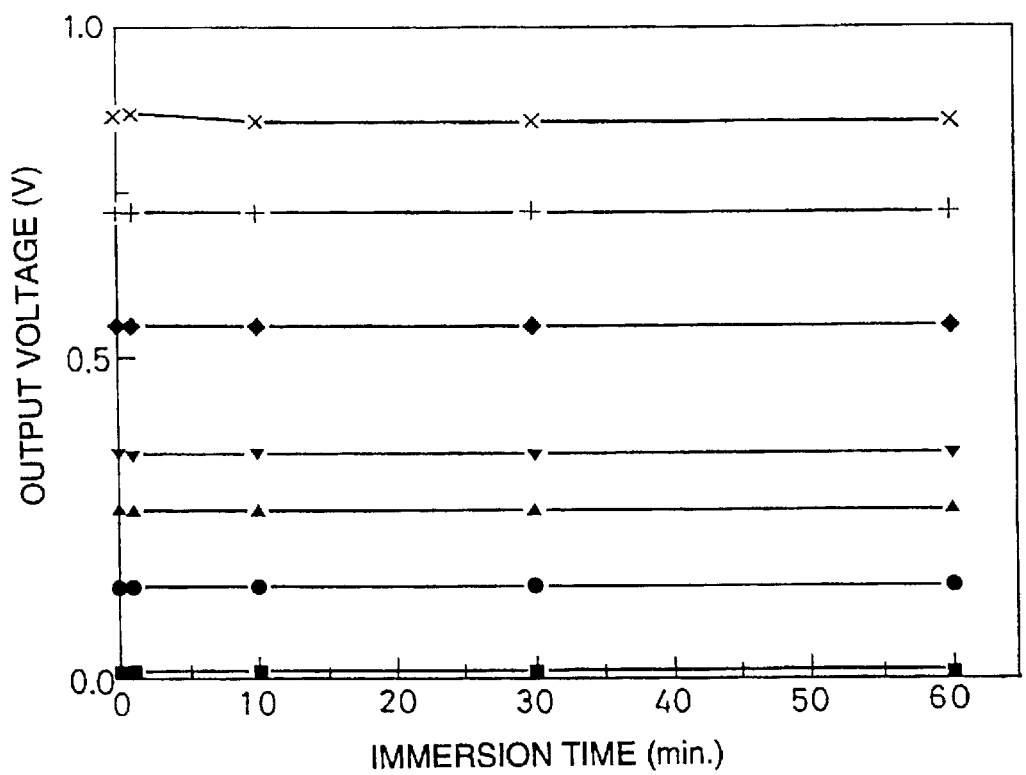
FIGS. 24–32 are graphs showing the water resistance of the humidity sensors of Examples 13–21, respectively.

The humidity sensor was evaluated for output and examined by the water resistance test as in Example 1. The output voltage versus relative humidity was the same as in Example 1. FIG. 24 shows the results of the water resistance test. The water resistance of the sensor of this Example was better than that of Example 1 since the reactive group was introduced into the intermediate polymer at a higher temperature than in Example 1 whereby some reactive groups underwent polymerization.

Example 14

A humidity sensor was fabricated as in Example 2 except that in introducing a reactive group into the intermediate polymer at its end, the reaction solution was stirred for 25 hours at 80° C. instead of stirring for 120 hours at 45° C. Note that the polymer had Mn of about 90,000 prior to crosslinking.

Figure 25:
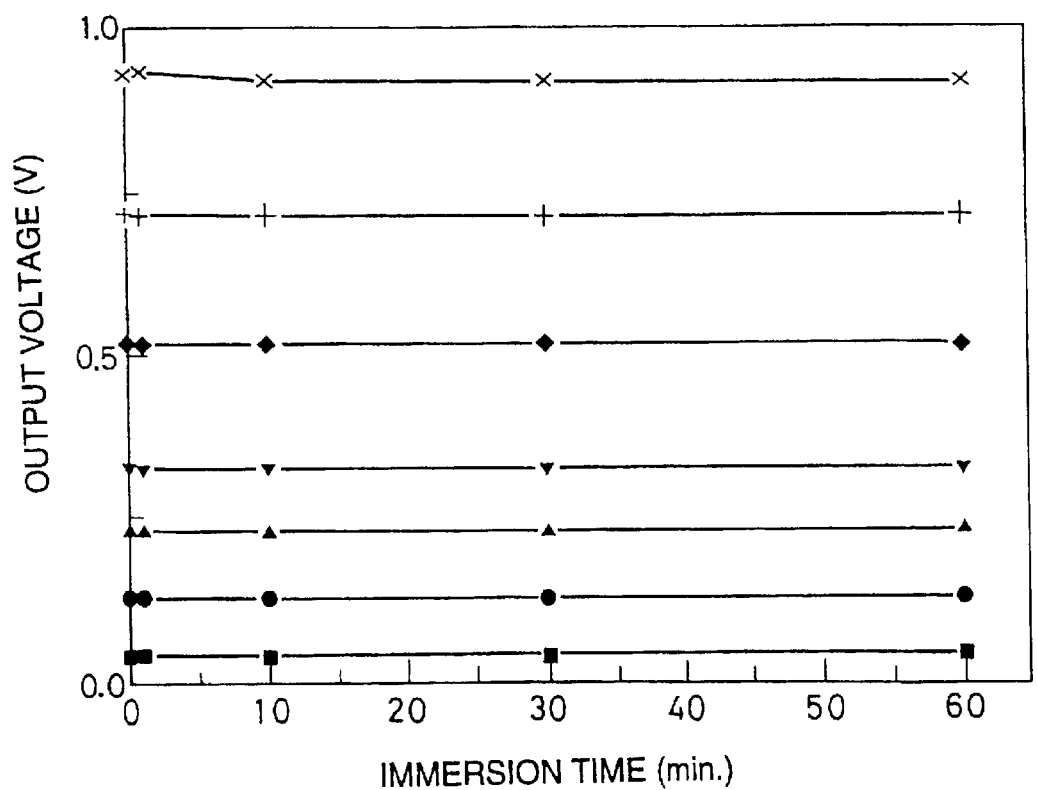

The humidity sensor was evaluated for output and examined by the water resistance test as in Example 1. The output voltage versus relative humidity was the same as in Example 2. FIG. 25 shows the results of the water resistance test. The water resistance of the sensor of this Example was better than that of Example 2 since the reactive group was introduced into the intermediate polymer at a higher temperature than in Example 2 whereby some reactive groups underwent polymerization.

Example 15

A humidity sensor was fabricated as in Example 3 except that in introducing a reactive group into the intermediate polymer at its end, the reaction solution was stirred for 20 hours at 80° C. instead of stirring for 120 hours at 45° C. Note that the polymer had Mn of about 80,000 prior to crosslinking.

Figure 26:
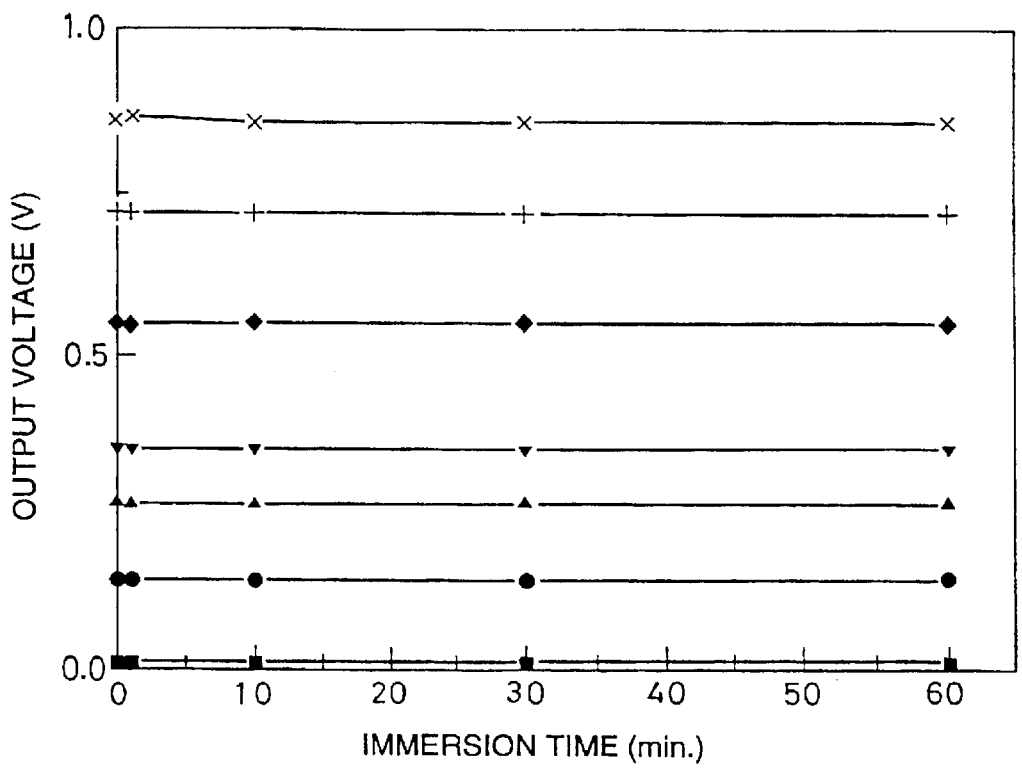

The humidity sensor was evaluated for output and examined by the water resistance test as in Example 1. The output voltage versus relative humidity was the same as in Example 3. FIG. 26 shows the results of the water resistance test. The water resistance of the sensor of this Example was better than that of Example 3 since the reactive group was introduced into the intermediate polymer at a higher temperature than in Example 3 whereby some reactive groups underwent polymerization.

Example 16

A humidity sensor was fabricated as in Example 5 except that in introducing a reactive group into the intermediate polymer at its end, the reaction solution was stirred for 20 hours at 80° C. instead of stirring for 120 hours at 45° C. Note that the polymer had Mn of about 80,000 prior to crosslinking.

Figure 27:
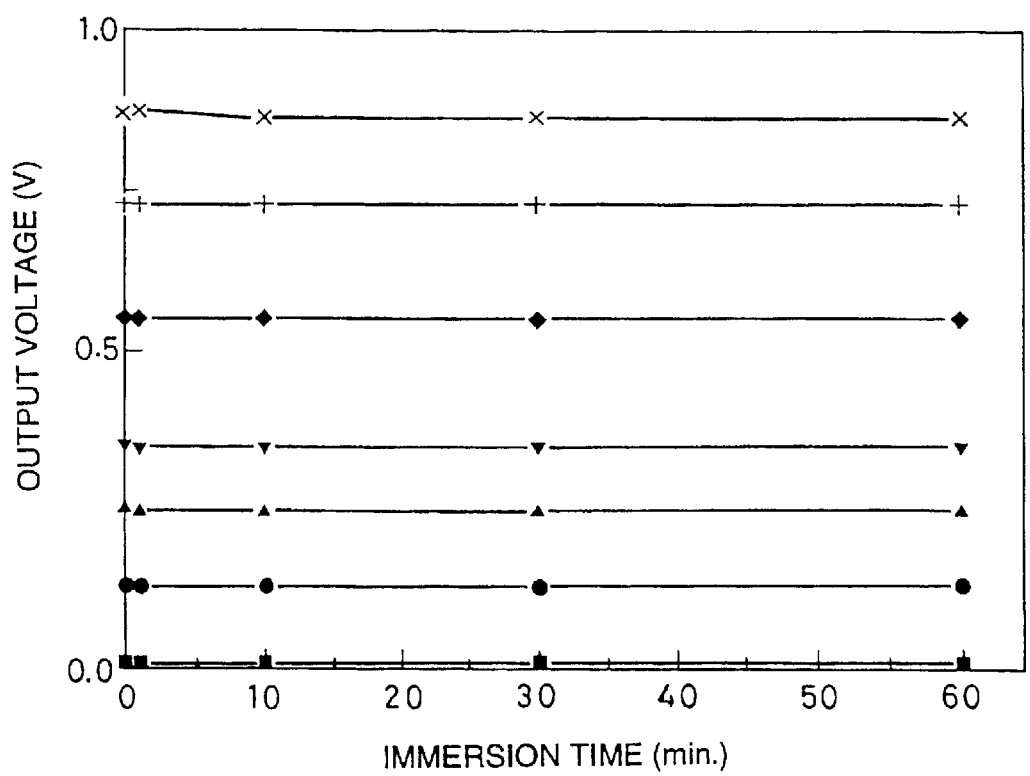

The humidity sensor was evaluated for output and examined by the water resistance test as in Example 1. The output voltage versus relative humidity was the same as in Example 5. FIG. 27 shows the results of the water resistance test. The water resistance of the sensor of this Example was better than that of Example 5 since the reactive group was introduced into the intermediate polymer at a higher temperature than in Example 5 whereby some reactive groups underwent polymerization.

Example 17

A humidity sensor was fabricated as in Example 6 except that in introducing a reactive group into the intermediate polymer at its end, the reaction solution was stirred for 20 hours at 80° C. instead of stirring for 120 hours at 45° C. Note that the polymer had Mn of about 80,000 prior to crosslinking.

Figure 28:
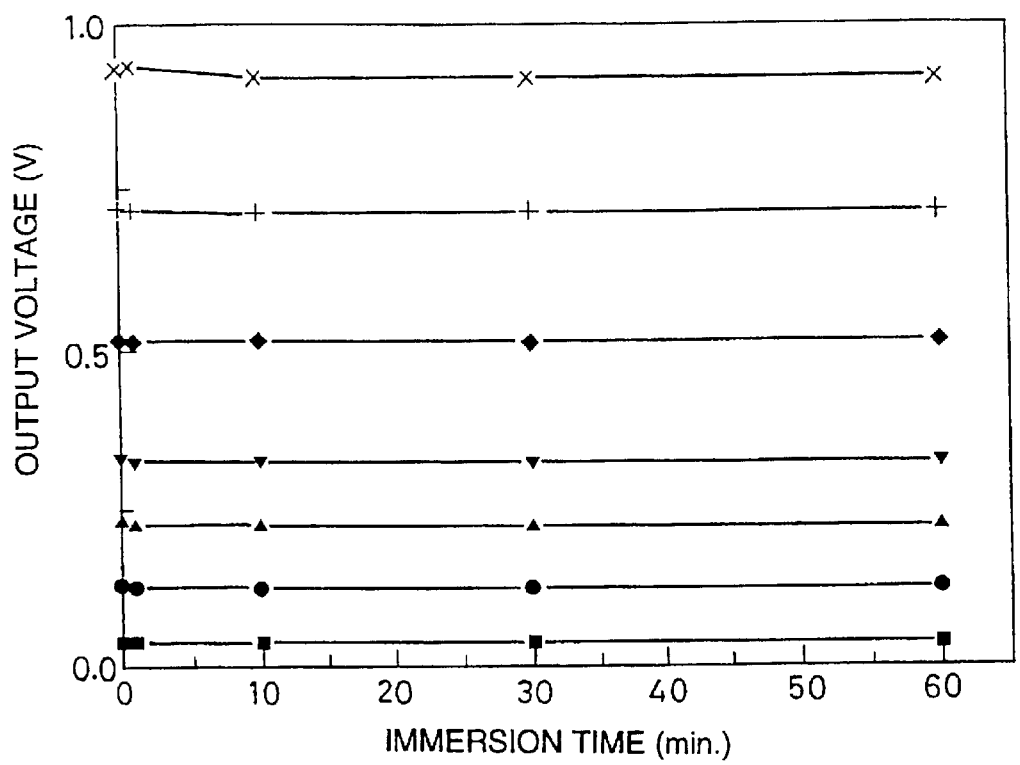

The humidity sensor was evaluated for output and examined by the water resistance test as in Example 1. The output voltage versus relative humidity was the same as in Example 6. FIG. 28 shows the results of the water resistance test. The water resistance of the sensor of this Example was better than that of Example 6 since the reactive group was introduced into the intermediate polymer at a higher temperature than in Example 6 whereby some reactive groups underwent polymerization.

Example 18

A humidity sensor was fabricated as in Example 7 except that in introducing a reactive group into the intermediate polymer at its end, the reaction solution was stirred for 20 hours at 80° C. instead of stirring for 120 hours at 45° C. Note that the polymer had Mn of about 100,000 prior to crosslinking.

Figure 29:
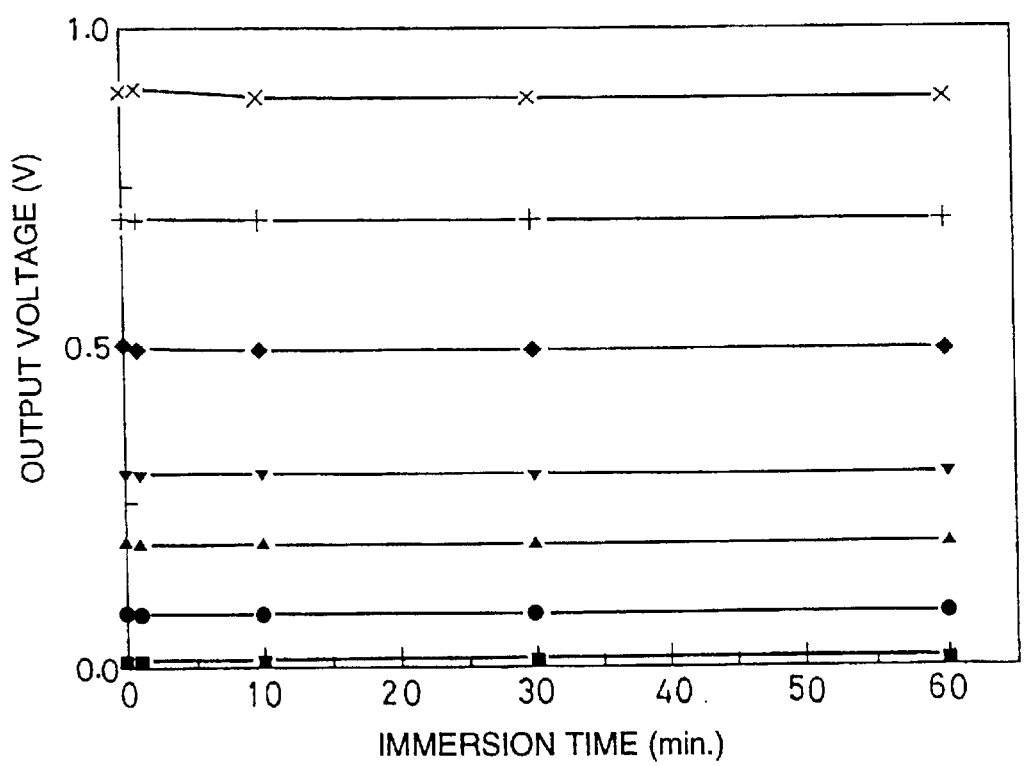

The humidity sensor was evaluated for output and examined by the water resistance test as in Example 1. The output voltage versus relative humidity was the same as in Example 7. FIG. 29 shows the results of the water resistance test. The water resistance of the sensor of this Example was better than that of Example 7 since the reactive group was introduced into the intermediate polymer at a higher temperature than in Example 7 whereby some reactive groups underwent polymerization.

Example 19

A humidity sensor was fabricated as in Example 8 except that in introducing a reactive group into the intermediate polymer at its end, the reaction solution was stirred for 20 hours at 80° C. instead of stirring for 100 hours at 35° C. Note that the polymer had Mn of about 80,000 prior to crosslinking.

Figure 30:
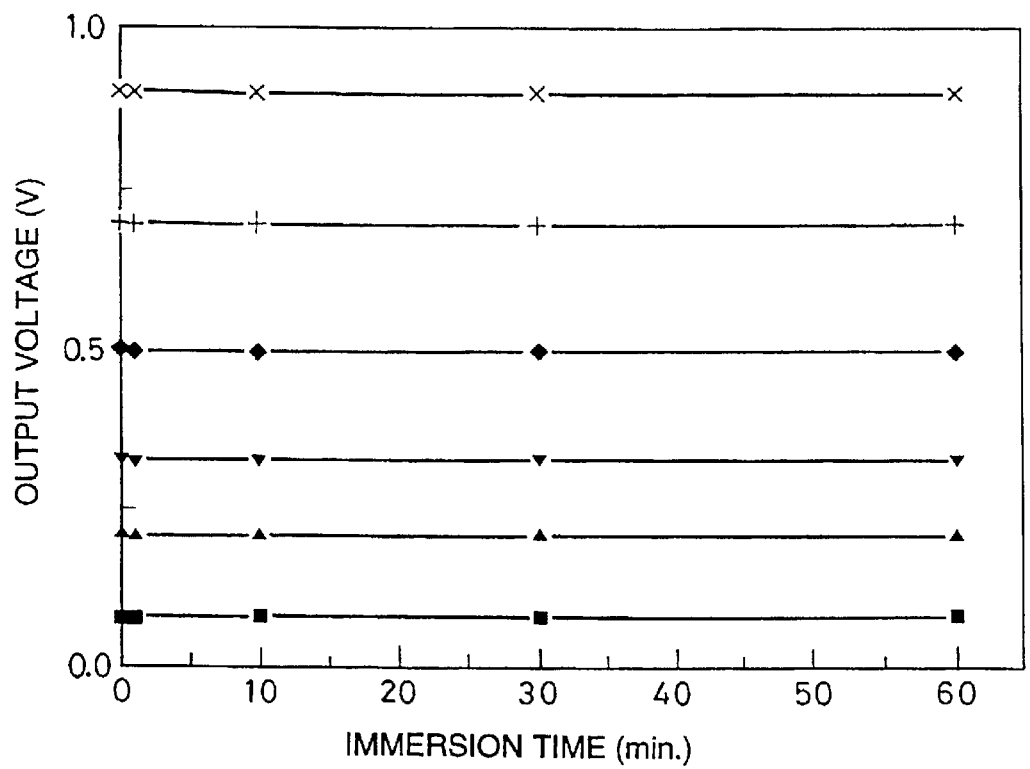

The humidity sensor was evaluated for output and examined by the water resistance test as in Example 1. The output voltage versus relative humidity was the same as in Example 8. FIG. 30 shows the results of the water resistance test. The water resistance of the sensor of this Example was better than that of Example 8 since the reactive group was introduced into the intermediate polymer at a higher temperature than in Example 8 whereby some reactive groups underwent polymerization.

Example 20

A humidity sensor was fabricated as in Example 10 except that in introducing a reactive group into the intermediate polymer at its end, the reaction solution was stirred for 20 hours at the reflux temperature instead of stirring for 100 hours at 35° C. Note that the polymer had Mn of about 150,000 prior to crosslinking.

Figure 31:
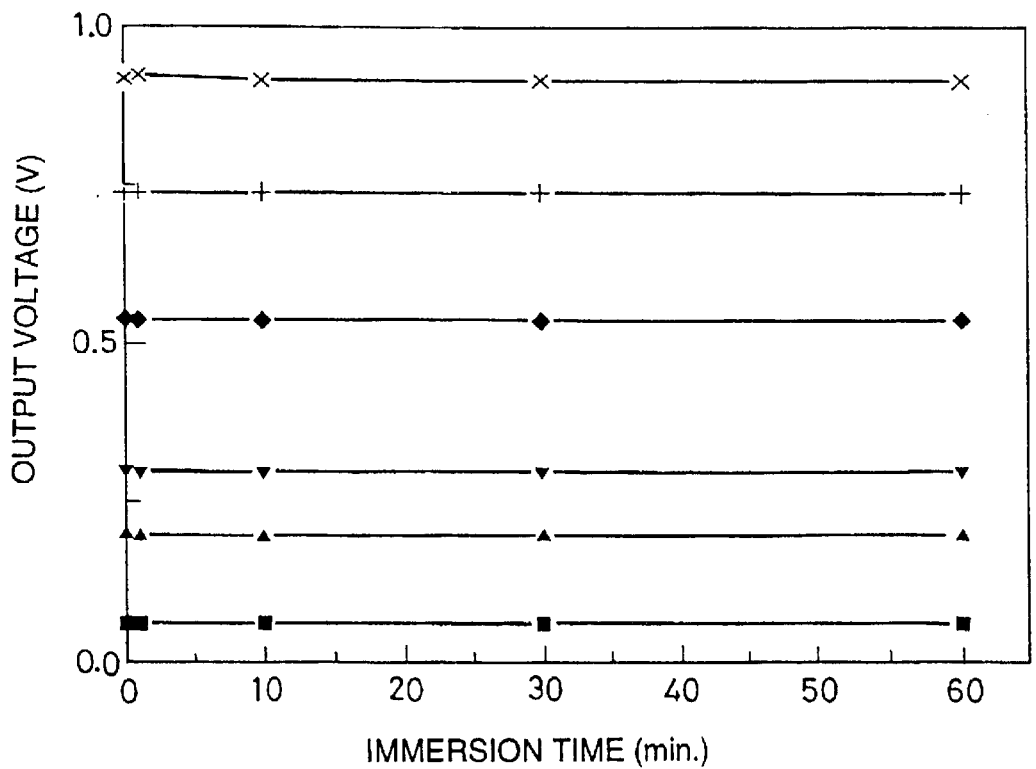

The humidity sensor was evaluated for output and examined by the water resistance test as in Example 1. The output voltage versus relative humidity was the same as in Example 10. FIG. 31 shows the results of the water resistance test. The water resistance of the sensor of this Example was better than that of Example 10 since the reactive group was introduced into the intermediate polymer at a higher temperature than in Example 10 whereby some reactive groups underwent polymerization.

Example 21

A humidity sensor was fabricated as in Example 11 except that in introducing a reactive group into the intermediate polymer at its end, the reaction solution was stirred for 20 hours at 80° C. instead of stirring for 100 hours at 35° C. Note that the polymer had Mn of about 150,000 prior to crosslinking.

Figure 32:
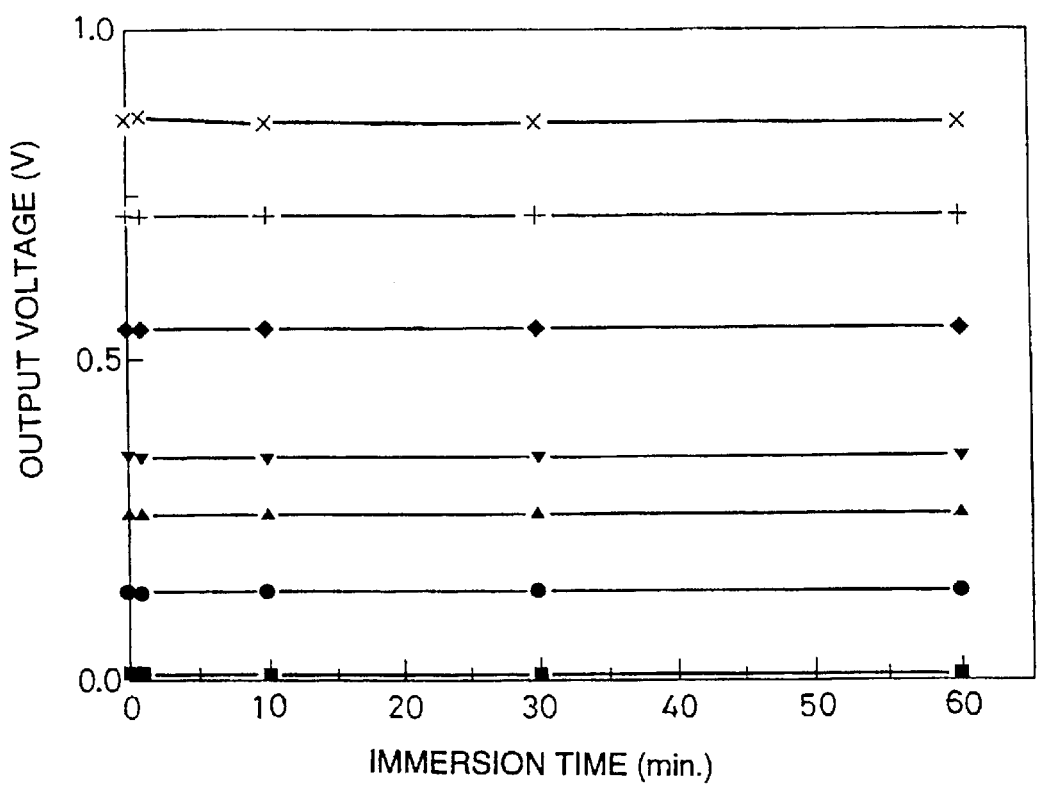

The humidity sensor was evaluated for output and examined by the water resistance test as in Example 1. The output voltage versus relative humidity was the same as in Example 11. FIG. 32 shows the results of the water resistance test. The water resistance of the sensor of this Example was better than that of Example 11 since the reactive group was introduced into the intermediate polymer at a higher temperature than in Example 11 whereby some reactive groups underwent polymerization.

Example 22

In 10.0 g of methanol were dissolved 4.25 g (0.020 mol) of 1,3-di(4-pyridyl)propane, 8.13 g (0.047 mol) of N,N,N',N'-tetramethyl-1,6-diaminohexane, and 7.62 g (0.067 mol) of 1,3-dichloropropane. The solution was stirred for 25 hours at the reflux temperature, effecting quaternization reaction. At the end of reaction, the reaction solution was cooled, to which 3.81 g (0.034 mol) of 1,3-dichloropropane and 20.0 g of methanol were added. The solution was stirred for a further 25 hours at the reflux temperature. At the end of reaction, the reaction solution was cooled, to which 30 g of 2-propanol was added. The reaction solution was added dropwise to a large volume of acetone whereupon an intermediate polymer precipitated. The precipitate was collected by filtration through a glass filter and dried in vacuum.

Then 15.0 g of the intermediate polymer, 15.0 g of N-(3-dimethylaminopropyl) methacrylamide and 0.2 g of m-dinitrobenzene as a polymerization inhibitor were dissolved in 30.0 g of methanol. The solution was stirred at the reflux temperature for 20 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum.

Except that this polymer was used as a conductive component, a humidity sensor was fabricated as in Example 1 by preparing a coating solution of the polymer and coating it to form a humidity sensitive thin film. Note that the polymer had Mn of about 130,000 prior to crosslinking.

Figure 33:
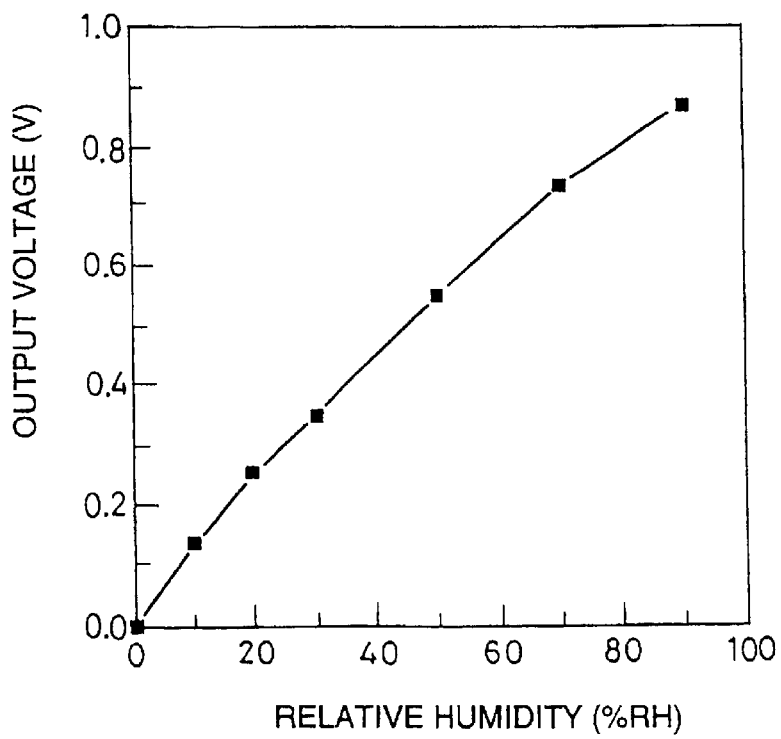
FIGS. 33 and 34 are graphs showing the output and water resistance of the sensor of Example 22, respectively.
Figure 34:
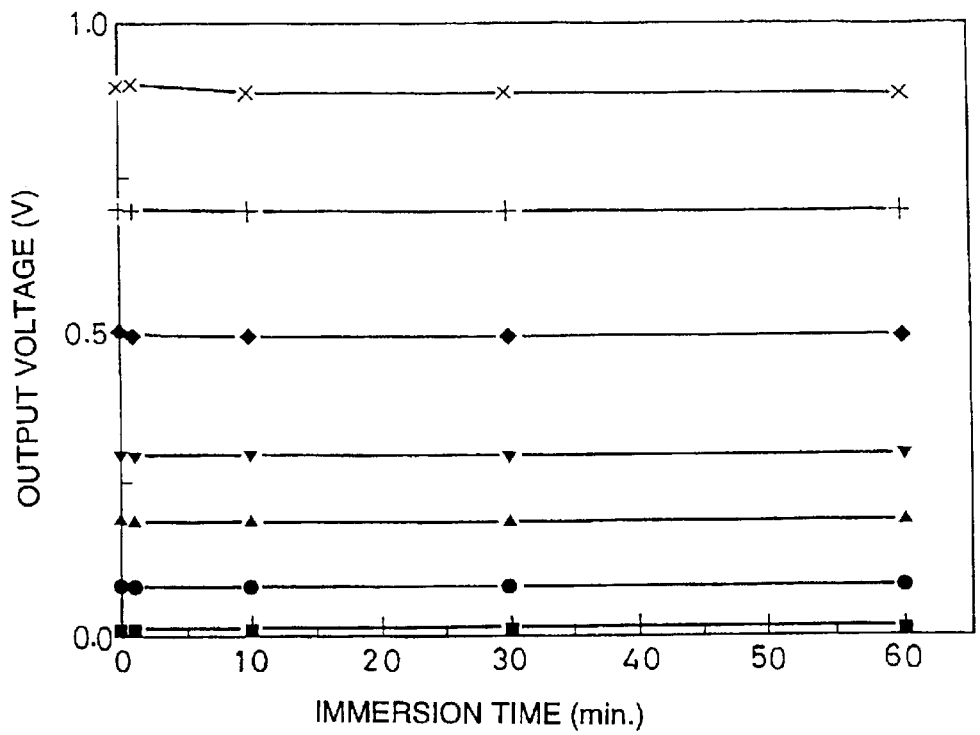

The humidity sensor was evaluated for output and examined by the water resistance test as in Example 1. FIG. 33 shows plots of output voltage versus relative humidity and FIG. 34 shows the results of the water resistance test. The advantages of the present invention are evident from FIGS. 33 and 34.

Example 23

In 10.0 g of methanol were dissolved 2.52 g (0.022 mol) of 1,4-diazabicyclo[2.2.2]octane, 9.03 g (0.052 mol) of N,N,N',N'-tetramethyl-1,6-diaminohexane, and 8.46 g (0.075 mol) of 1,3-dichloropropane. The solution was stirred for 25 hours at the reflux temperature, effecting quaternization reaction. At the end of reaction, the reaction solution was cooled, to which 4.23 g (0.037 mol) of 1,3-dichloropropane and 20.0 g of methanol were added. The reaction solution was stirred for a further 25 hours at the reflux temperature. At the end of reaction, the reaction solution was cooled, to which 30 g of 2-propanol was added. The reaction solution was added dropwise to a large volume of acetone whereupon an intermediate polymer precipitated.

The precipitate was collected by filtration through a glass filter and dried in vacuum.

Then 15.0 g of the intermediate polymer, 15.0 g of N-(3-dimethylaminopropyl)methacrylamide and 0.2 g of m-dinitrobenzene as a polymerization inhibitor were dissolved in 30.0 g of methanol. The solution was stirred at the reflux temperature for 20 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum.

Except that this polymer was used as a conductive component, a humidity sensor was fabricated as in Example 1 by preparing a coating solution of the polymer and coating it to form a humidity sensitive thin film. Note that the polymer had Mn of about 110,000 prior to crosslinking.

Figure 35:
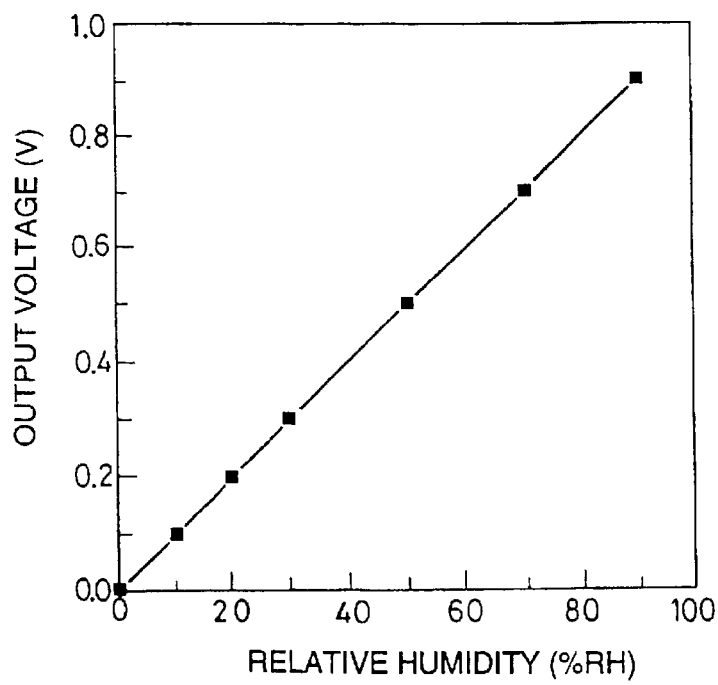
FIGS. 35 and 36 are graphs showing the output and water resistance of the sensor of Example 23, respectively.
Figure 36:
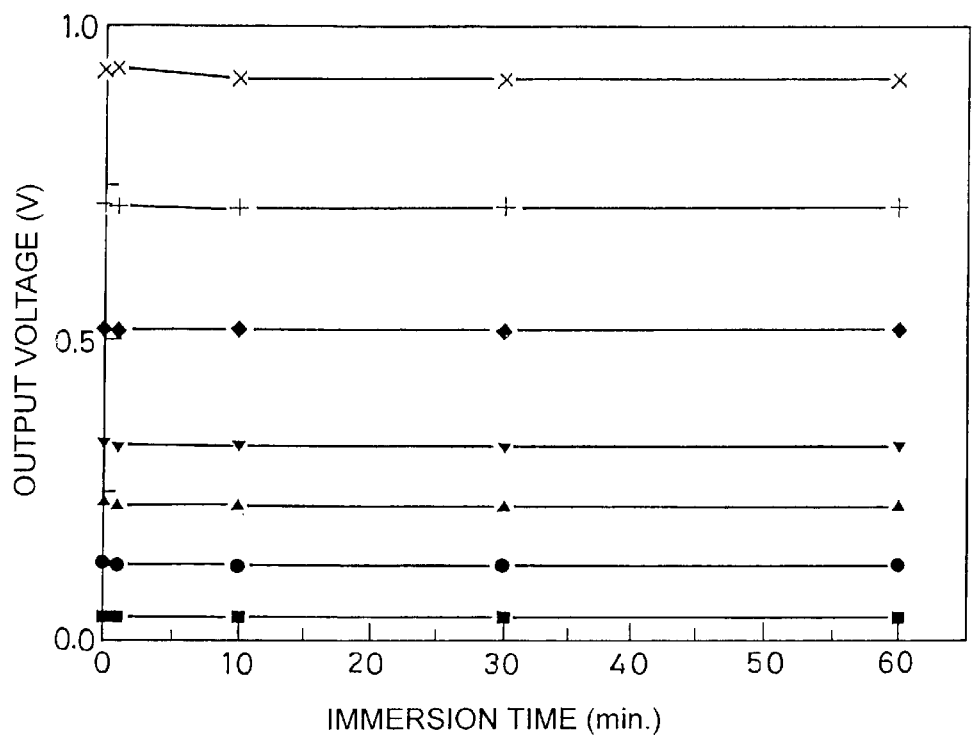

The humidity sensor was evaluated for output and examined by the water resistance test as in Example 1. FIG. 35 shows plots of output voltage versus relative humidity and FIG. 36 shows the results of the water resistance test. The advantages of the present invention are evident from FIGS. 35 and 36.

Example 24

In 10.0 g of methanol were dissolved 2.51 g (0.022 mol) of N,N'-dimethylpiperazine, 9.01 g (0.052 mol) of N,N,N',N'-tetramethyl-1,6-diaminohexane, and 8.44 g (0.075 mol) of 1,3-dichloropropane. The solution was stirred for 25 hours at the reflux temperature, effecting quaternization reaction. At the end of reaction, the reaction solution was cooled, to which 4.22 g (0.037 mol) of 1,3-dichloropropane and 20.0 g of methanol were added. The reaction solution was stirred for a further 25 hours at the reflux temperature. At the end of reaction, the reaction solution was cooled, to which 30 g of 2-propanol was added. The reaction solution was added dropwise to a large volume of acetone whereupon an intermediate polymer precipitated. The precipitate was collected by filtration through a glass filter and dried in vacuum.

Then 15.0 g of the intermediate polymer, 15.0 g of N-(3-dimethylaminopropyl)methacrylamide and 0.2 g of m-dinitrobenzene as a polymerization inhibitor were dissolved in 30.0 g of methanol. The solution was stirred at the reflux temperature for 20 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum.

Except that this polymer was used as a conductive component, a humidity sensor was fabricated as in Example 1 by preparing a coating solution of the polymer and coating it to form a humidity sensitive thin film. Note that the polymer had Mn of about 120,000 prior to crosslinking.

Figure 37:
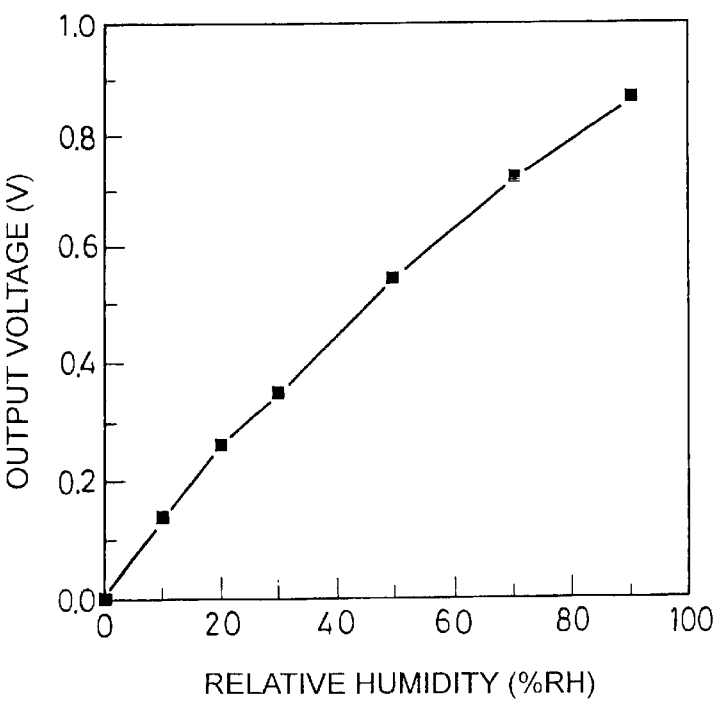
FIGS. 37 and 38 are graphs showing the output and water resistance of the sensor of Example 24, respectively.
Figure 38:
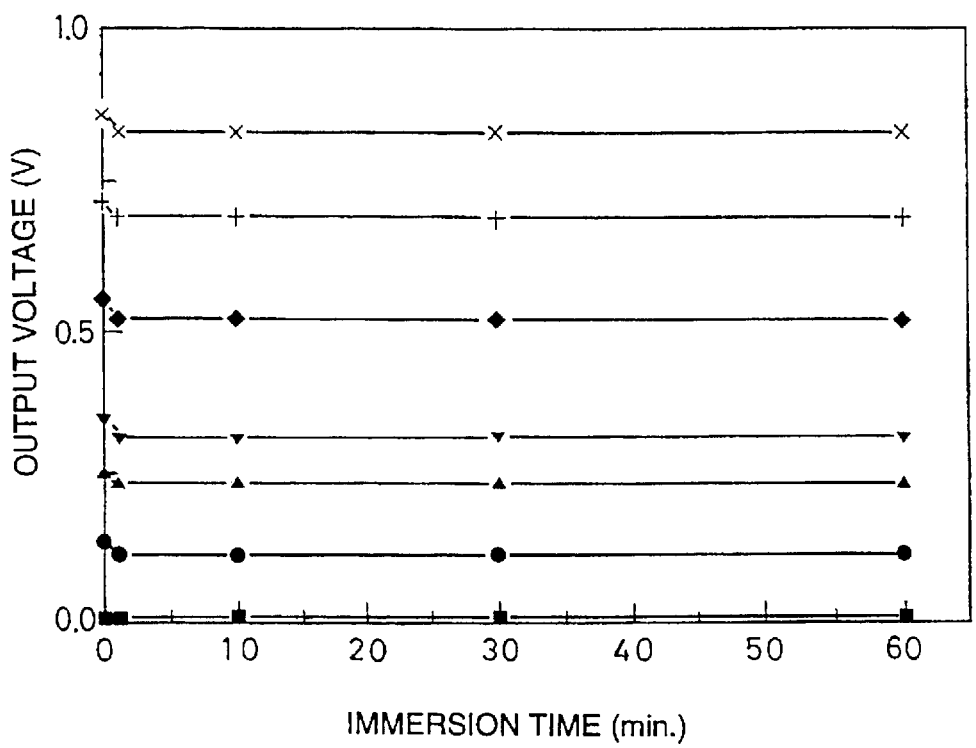

The humidity sensor was evaluated for output and examined by the water resistance test as in Example 1. FIG. 37 shows plots of output voltage versus relative humidity and FIG. 38 shows the results of the water resistance test. The advantages of the present invention are evident from FIGS. 37 and 38.

Example 25

In 10.0 g of methanol were dissolved 4.69 g (0.020 mol) of N,N'-dimethyl-1,3-dipiperidylpropane, 7.90 g (0.046 mol) of N,N,N',N'-tetramethyl-1,6-diaminohexane, and 7.41 g (0.066 mol) of 1,3-dichloropropane. The solution was stirred for 25 hours at the reflux temperature, effecting quaternization reaction. At the end of reaction, the reaction solution was cooled, to which 3.71 g (0.033 mol) of 1,3-dichloropropane and 20.0 g of methanol were added. The reaction solution was stirred for a further 25 hours at the reflux temperature. At the end of reaction, the reaction solution was cooled, to which 30 g of 2-propanol was added. The reaction solution was added dropwise to a large volume of acetone whereupon an intermediate polymer precipitated. The precipitate was collected by filtration through a glass filter and dried in vacuum.

Then 15.0 g of the intermediate polymer, 15.0 g of N-(3-dimethylaminopropyl)methacrylamide and 0.2 g of m-dinitrobenzene as a polymerization inhibitor were dissolved in 30.0 g of methanol. The solution was stirred at the reflux temperature for 20 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum.

Except that this polymer was used as a conductive component, a humidity sensor was fabricated as in Example 1 by preparing a coating solution of the polymer and coating it to form a humidity sensitive thin film. Note that the polymer had Mn of about 90,000 prior to crosslinking.

Figure 39:
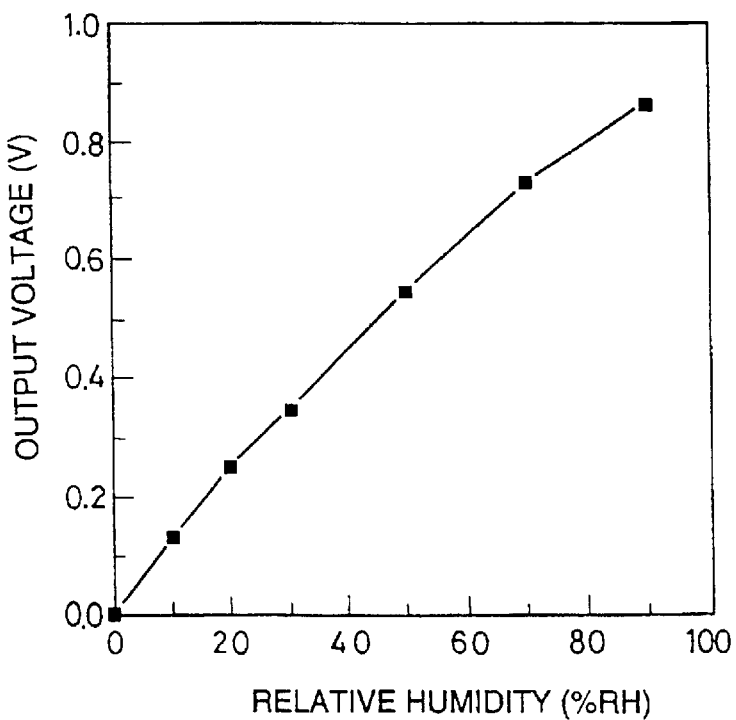
FIGS. 39 and 40 are graphs showing the output and water resistance of the sensor of Example 25, respectively.
Figure 40:
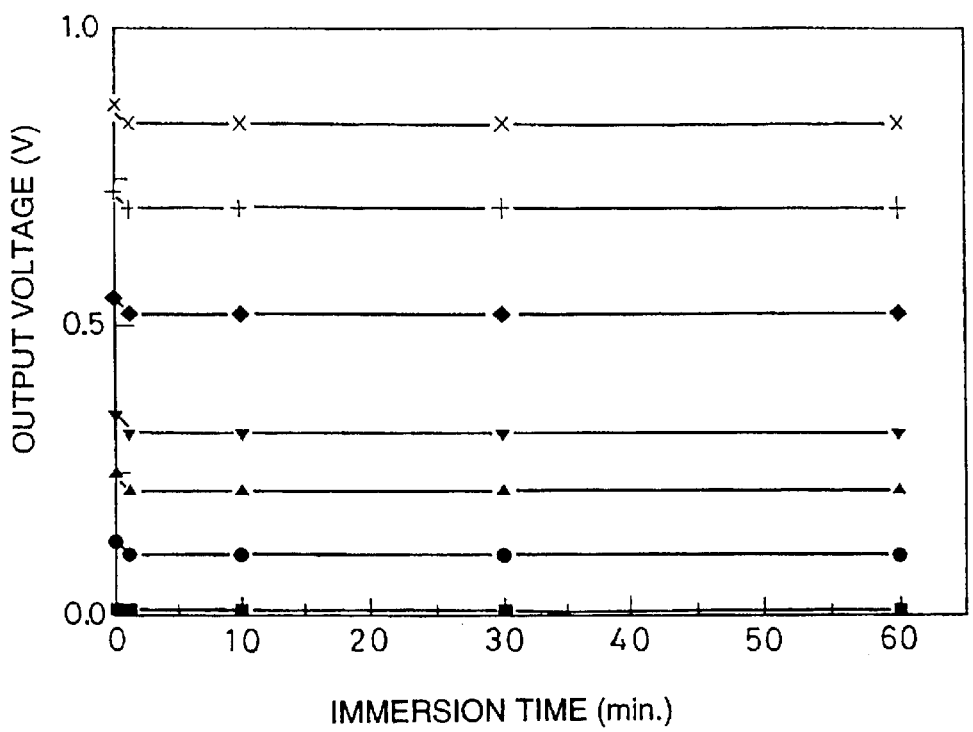

The humidity sensor was evaluated for output and examined by the water resistance test as in Example 1. FIG. 39 shows plots of output voltage versus relative humidity and FIG. 40 shows the results of the water resistance test. The advantages of the present invention are evident from FIGS. 39 and 40.

Example 26

In 10.0 g of methanol were dissolved 9.29 g (0.083 mol) of 1,4-diazabicyclo[2.2.2]octane and 10.71 g (0.069 mol) of 1,6-dichlorohexane. The solution was stirred for 15 hours at the reflux temperature, effecting quaternization reaction. At the end of reaction, the reaction solution was cooled, to which 4.65 g (0.041 mol) of 1,4-diazabicyclo[2.2.2]octane and 20.0 g of methanol were added. The reaction solution was stirred for a further 15 hours at the reflux temperature. At the end of reaction, the reaction solution was cooled, to which 30 g of 2-propanol was added. The reaction solution was added dropwise to a large volume of acetone whereupon an intermediate polymer precipitated. The precipitate was collected by filtration through a glass filter and dried in vacuum (yield 15.5 g).

Then 15.0 g of the intermediate polymer and 15.0 g of vinylbenzyl chloride (mixture of m- and p-forms) were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 20.3 g).

Except that this polymer was used as a conductive component, a humidity sensor was fabricated as in Example 1 by preparing a coating solution of the polymer and coating it to form a humidity sensitive thin film. Note that the polymer had Mn of about 50,000 prior to crosslinking.

Figure 41:
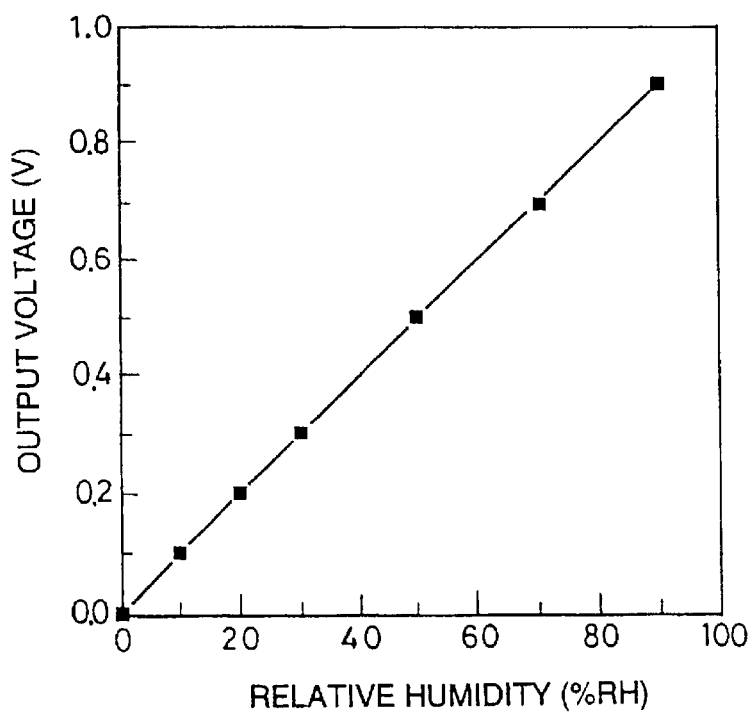
FIGS. 41 and 42 are graphs showing the output and water resistance of the sensor of Example 26, respectively.
Figure 42:
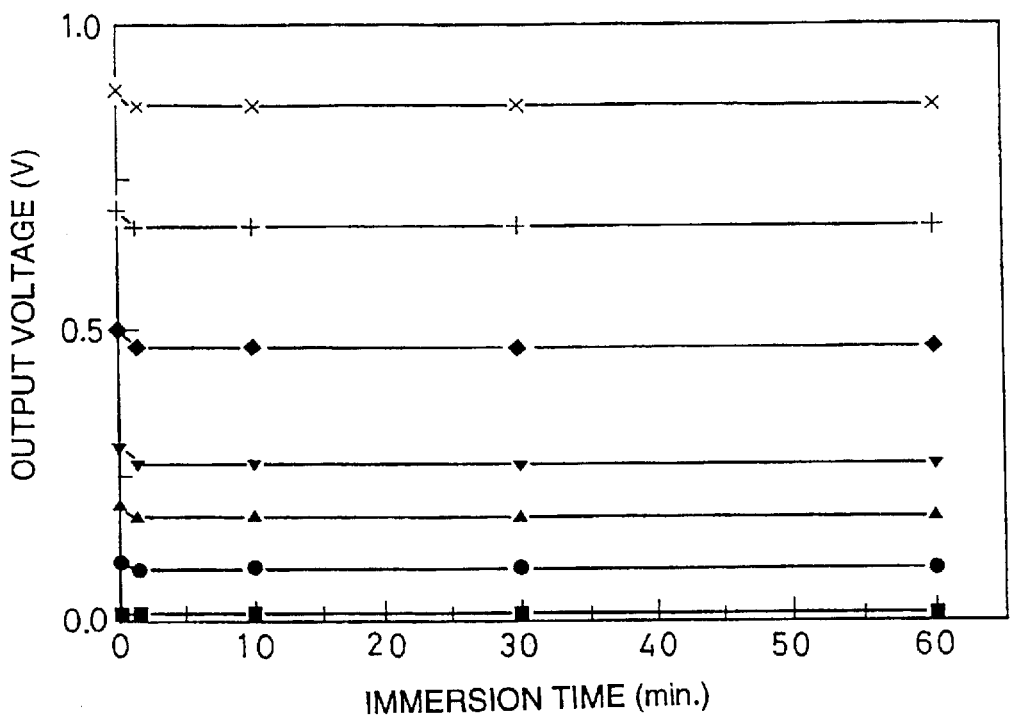

The humidity sensor was evaluated for output and examined by the water resistance test as in Example 1. FIG. 41 shows plots of output voltage versus relative humidity and FIG. 42 shows the results of the water resistance test. The advantages of the present invention are evident from FIGS. 41 and 42.

Example 27

In 10.0 g of methanol were dissolved 3.68 g (0.033 mol) of 1,4-diazabicyclo[2.2.2]octane, 7.83 g (0.033 mol) of 4,4'-trimethylenebis(1-methylpiperidine), and 8.49 g (0.055 mol) of 1,6-dichlorohexane. The solution was stirred for 15 hours at the reflux temperature, effecting quaternization reaction. At the end of reaction, the reaction solution was cooled, to which 3.68 g (0.033 mol) of 1,4-diazabicyclo [2.2.2]octane and 20.0 g of methanol were added. The reaction solution was stirred for a further 15 hours at the reflux temperature. At the end of reaction, the reaction solution was cooled, to which 30 g of 2-propanol was added. The reaction solution was added dropwise to a large volume of acetone whereupon an intermediate polymer precipitated. The precipitate was collected by filtration through a glass filter and dried in vacuum (yield 16.2 g).

Then 15.0 g of the intermediate polymer and 15.0 g of vinylbenzyl chloride (mixture of m- and p-forms) were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 19.2 g).

Except that this polymer was used as a conductive component, a humidity sensor was fabricated as in Example 1 by preparing a coating solution of the polymer and coating it to form a humidity sensitive thin film. Note that the polymer had Mn of about 60,000 prior to crosslinking.

Figure 43:
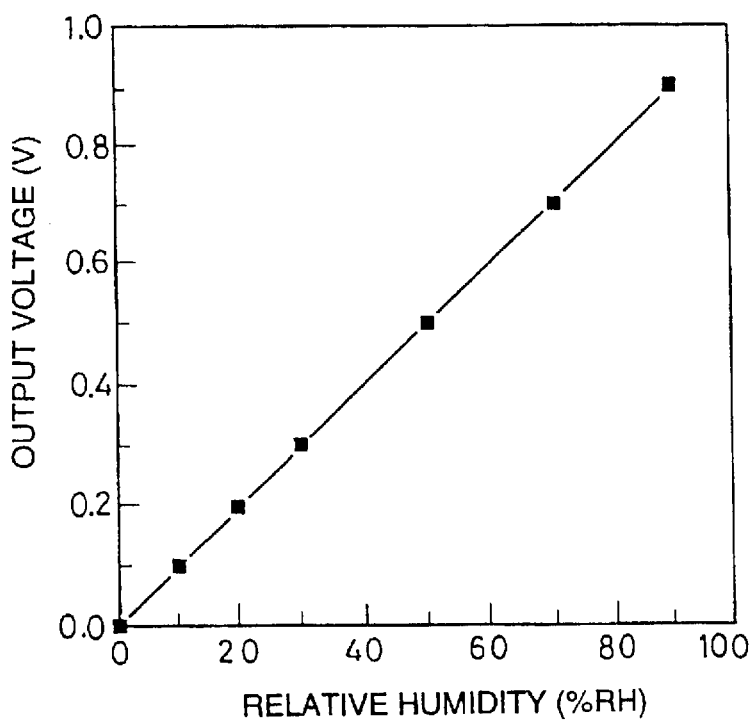
FIGS. 43 and 44 are graphs showing the output and water resistance of the sensor of Example 27, respectively.
Figure 44:
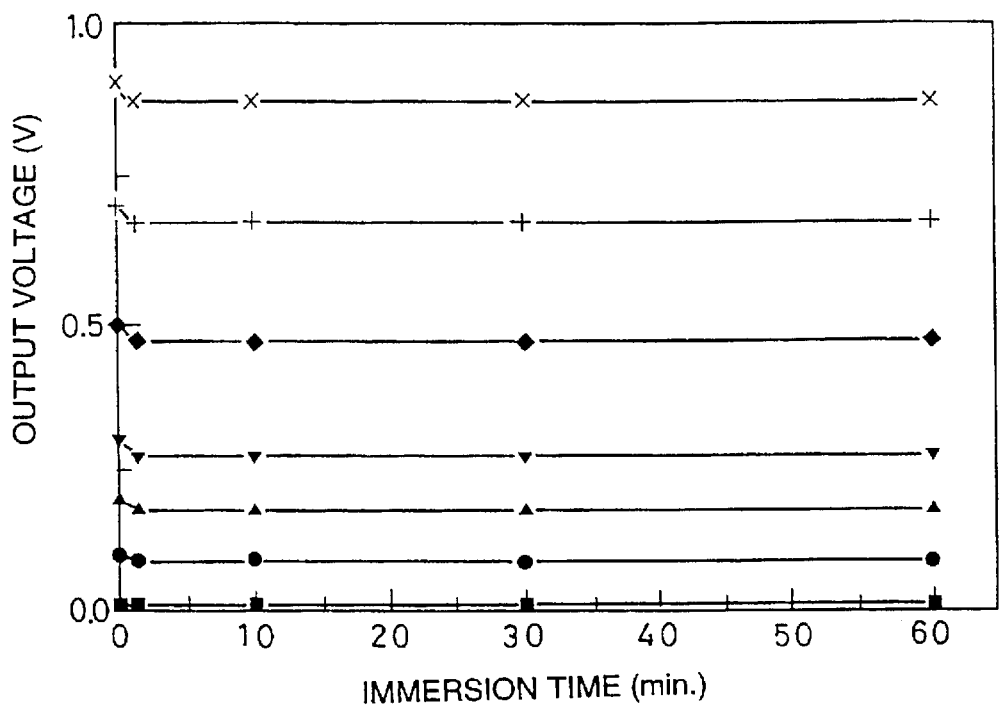

The humidity sensor was evaluated for output and examined by the water resistance test as in Example 1. FIG. 43 shows plots of output voltage versus relative humidity and FIG. 44 shows the results of the water resistance test. The advantages of the present invention are evident from FIGS. 43 and 44.

Example 28

In 10.0 g of methanol were dissolved 9.46 g (0.084 mol) of 1,4-diazabicyclo[2.2.2]octane, 8.72 g (0.056 mol) of 1,6-dichlorohexane, and 1.81 g (0.014 mol) of 1,3-dichloro-2-propanol. The solution was stirred for 15 hours at the reflux temperature, effecting quaternization reaction. At the end of reaction, the reaction solution was cooled, to which 4.73 g (0.042 mol) of 1,4-diazabicyclo [2.2.2]octane and 20.0 g of methanol were added. The reaction solution was stirred for a further 15 hours at the reflux temperature. At the end of reaction, the reaction solution was cooled, to which 30 g of 2-propanol was added. The reaction solution was added dropwise to a large volume of acetone whereupon an intermediate polymer precipitated. The precipitate was collected by filtration through a glass filter and dried in vacuum (yield 15.2 g).

Then 15.0 g of the intermediate polymer and 15.0 g of vinylbenzyl chloride (mixture of m- and p-forms) were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 18.2 g).

Except that this polymer was used as a conductive component, a humidity sensor was fabricated as in Example 1 by preparing a coating solution of the polymer and coating it to form a humidity sensitive thin film. Note that the polymer had Mn of about 40,000 prior to crosslinking.

Figure 45:
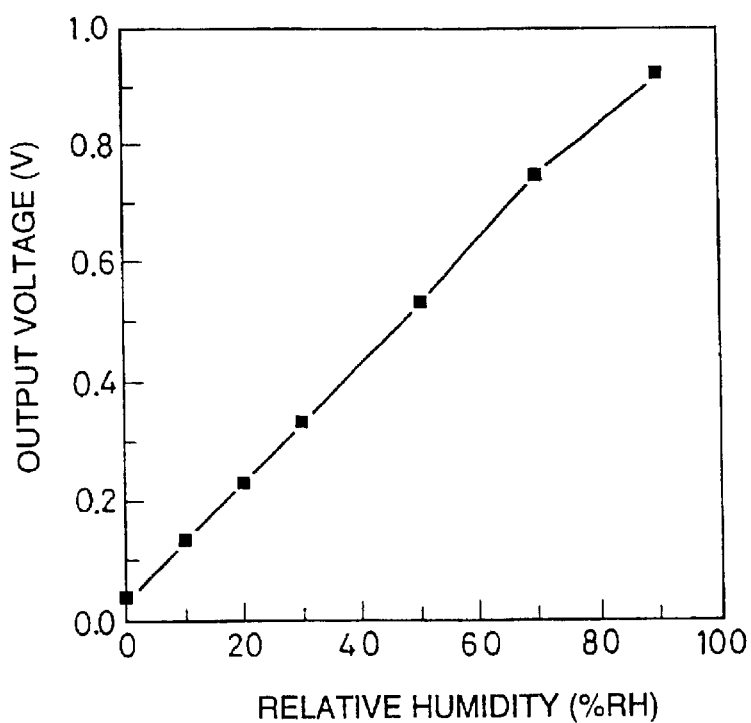
FIGS. 45 and 46 are graphs showing the output and water resistance of the sensor of Example 28, respectively.
Figure 46:
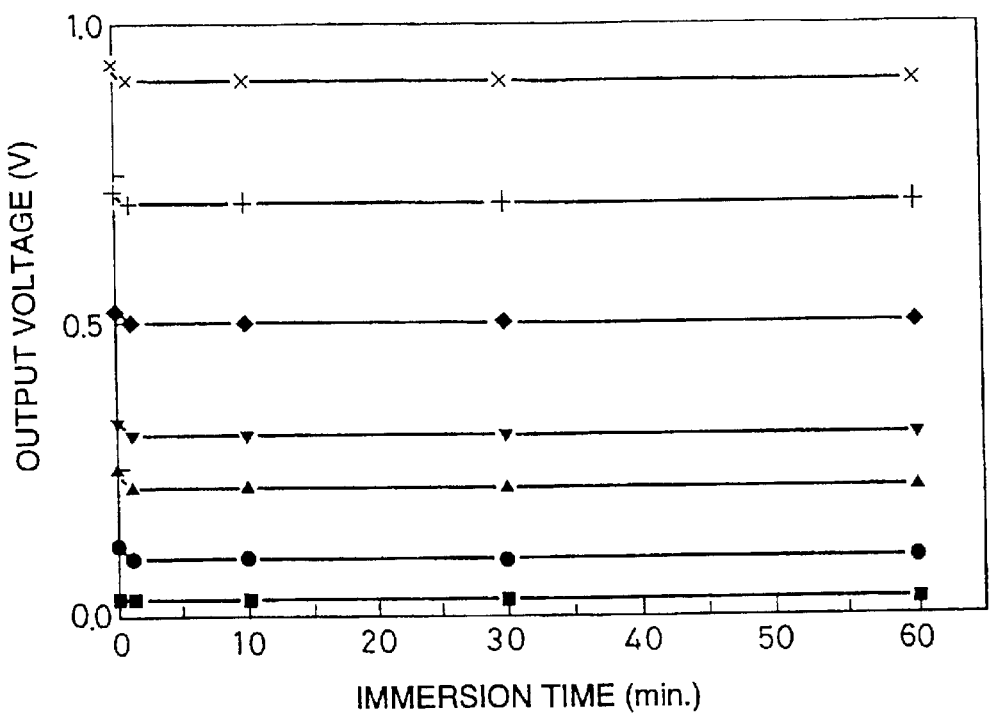

The humidity sensor was evaluated for output and examined by the water resistance test as in Example 1. FIG. 45 shows plots of output voltage versus relative humidity and FIG. 46 shows the results of the water resistance test. The advantages of the present invention are evident from FIGS. 45 and 46.

Example 29

In 10.0 g of methanol were dissolved 7.52 g (0.067 mol) of 1,4-diazabicyclo[2.2.2]octane and 12.48 g (0.080 mol) of 1,6-dichlorohexane. The solution was stirred for 15 hours at the reflux temperature, effecting quaternization reaction. At the end of reaction, the reaction solution was cooled, to which 6.24 g (0.040 mol) of 1,6-dichlorohexane and 20.0 g of methanol were added. The reaction solution was stirred for a further 15 hours at the reflux temperature. At the end of reaction, the reaction solution was cooled, to which 30 g of 2-propanol was added. The reaction solution was added dropwise to a large volume of acetone whereupon an intermediate polymer precipitated. The precipitate was collected by filtration through a glass filter and dried in vacuum (yield 17.5 g).

Then 15.0 g of the intermediate polymer and 15.0 g of N-(3-dimethylaminopropyl)methacrylamide were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 18.4 g).

Except that this polymer was used as a conductive component, a humidity sensor was fabricated as in Example 1 by preparing a coating solution of the polymer and coating it to form a humidity sensitive thin film. Note that the polymer had Mn of about 50,000 prior to crosslinking.

Figure 47:
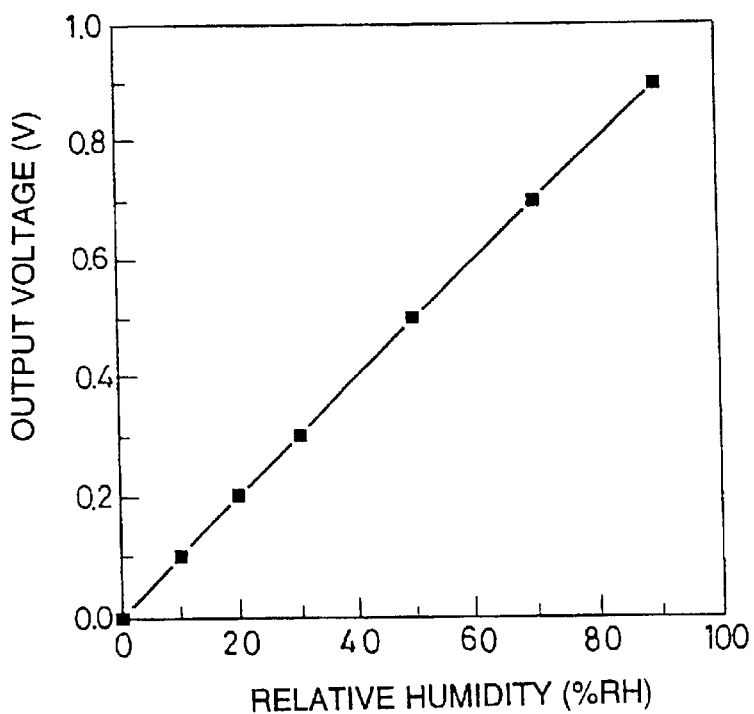
FIGS. 47 and 48 are graphs showing the output and water resistance of the sensor of Example 29, respectively.
Figure 48:
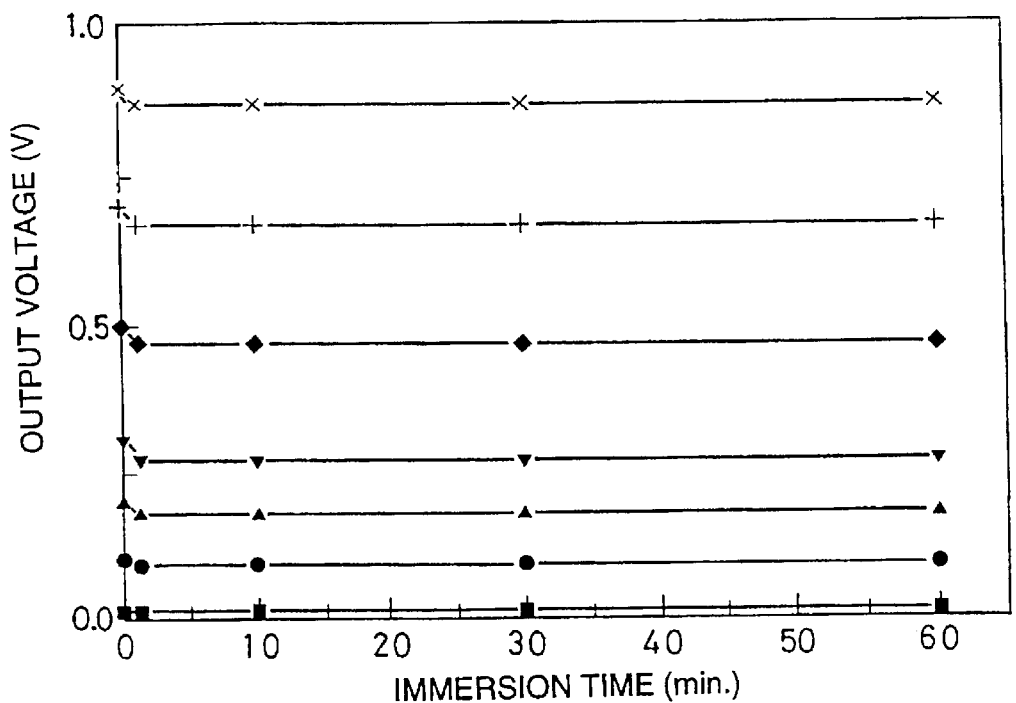

The humidity sensor was evaluated for output and examined by the water resistance test as in Example 1. FIG. 47 shows plots of output voltage versus relative humidity and FIG. 48 shows the results of the water resistance test. The advantages of the present invention are evident from FIGS. 47 and 48.

Example 30

The intermediate polymer synthesized, separated and purified in Example 29, 15.0 g, and 15.0 g of N-(3-dimethylaminopropyl) acrylamide were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 16.2 g).

Except that this polymer was used as a conductive component, a humidity sensor was fabricated as in Example 1 by preparing a coating solution of the polymer and coating it to form a humidity sensitive thin film. Note that the polymer had Mn of about 50,000 prior to crosslinking.

Figure 49:
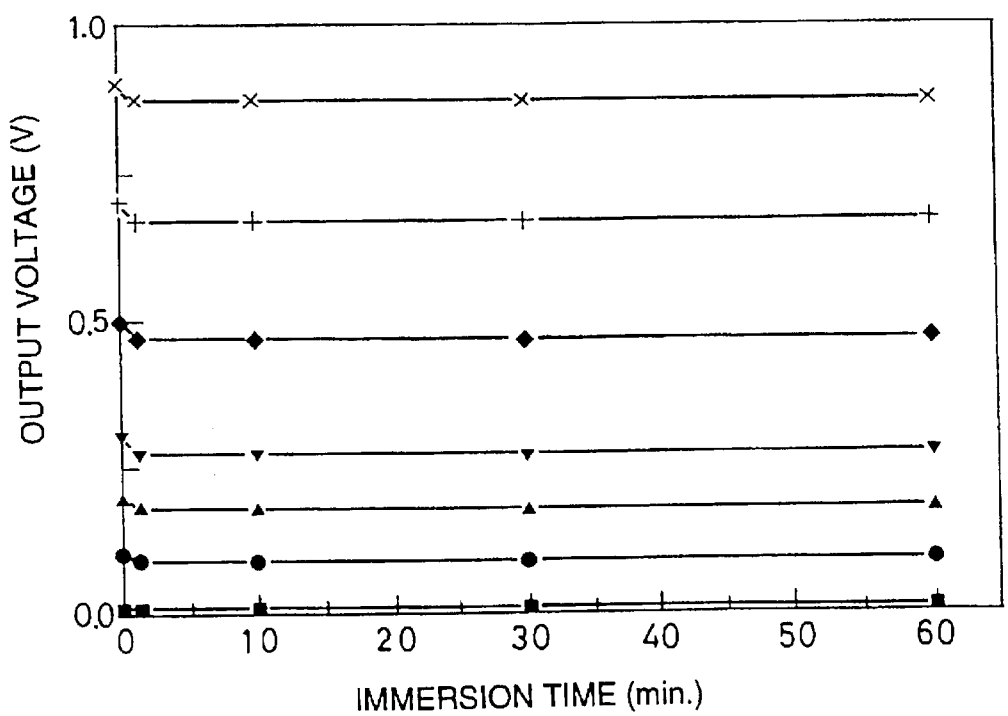
FIG. 49 is a graph showing the water resistance of the humidity sensor of Example 30.

The humidity sensor was evaluated for output and examined by the water resistance test as in Example 1. The output voltage versus relative humidity was the same as in Example 29. FIG. 49 shows the results of the water resistance test. The advantages of the present invention are evident from these results.

Example 31

In 10.0 g of methanol were dissolved 9.46 g (0.084 mol) of 1,4-diazabicyclo[2.2.2]octane, 8.72 g (0.056 mol) of 1,6-dichlorohexane, and 1.81 g (0.014 mol) of 1,3-dichloro-2-propanol. The solution was stirred for 15 hours at the reflux temperature, effecting quaternization reaction. At the end of reaction, the reaction solution was cooled, to which 5.42 g (0.042 mol) of 1,3-dichloro-2-propanol and 20.0 g of methanol were added. The reaction solution was stirred for a further 15 hours at the reflux temperature. At the end of reaction, the reaction solution was cooled and added dropwise to a large volume of acetone whereupon an intermediate polymer precipitated. The precipitate was collected by filtration through a glass filter and dried in vacuum (yield 18.1 g).

Then 15.0 g of the intermediate polymer and 15.0 g of N-(3-dimethylaminopropyl)methacrylamide were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 15.4 g).

Except that this polymer was used as a conductive component, a humidity sensor was fabricated as in Example 1 by preparing a coating solution of the polymer and coating it to form a humidity sensitive thin film. Note that the polymer had Mn of about 40,000 prior to crosslinking.

Figure 50:
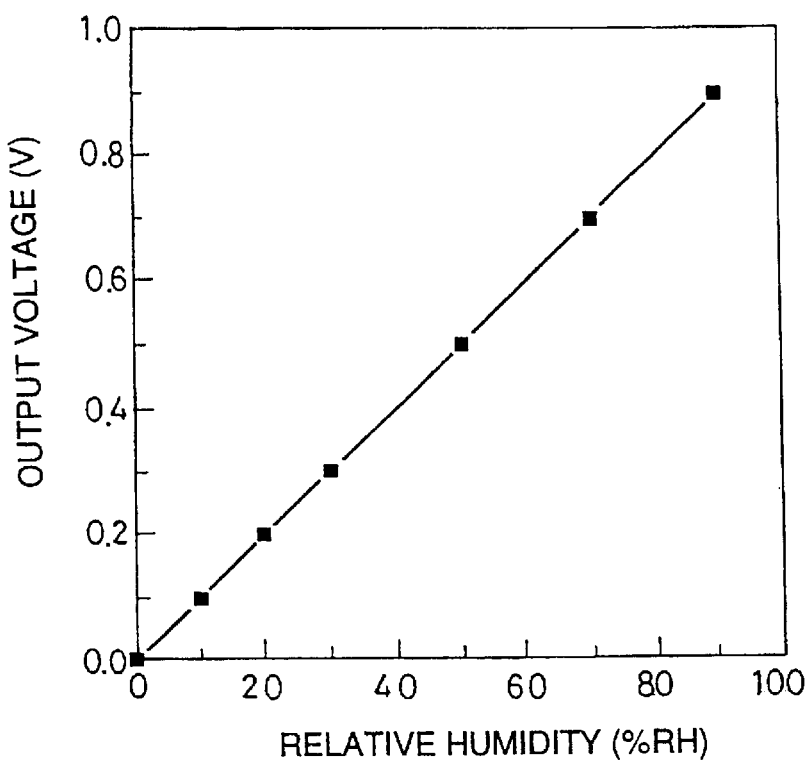
FIGS. 50 and 51 are graphs showing the output and water resistance of the sensor of Example 31, respectively.
Figure 51:
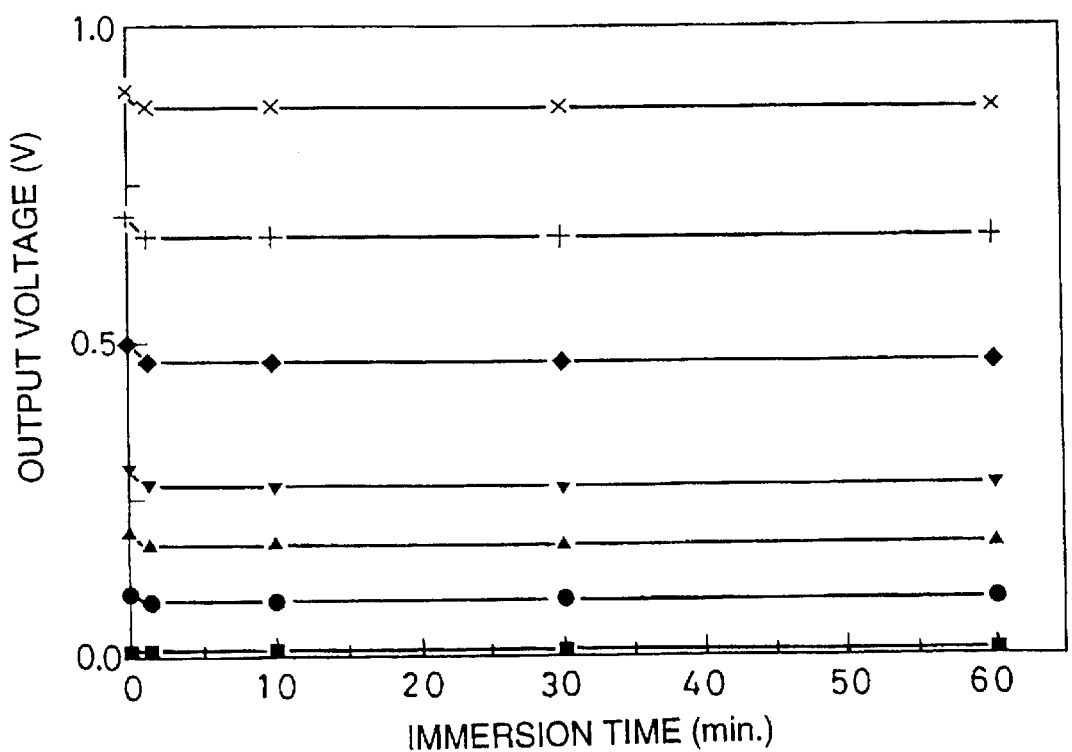

The humidity sensor was evaluated for output and examined by the water resistance test as in Example 1. FIG. 50 shows plots of output voltage versus relative humidity and FIG. 51 shows the results of the water resistance test. The advantages of the present invention are evident from FIGS. 50 and 51.

Example 32

In 10.0 g of methanol were dissolved 9.38 g (0.082 mol) of N,N'-dimethylpiperazine and 10.62 g (0.068 mol) of 1,6-dichlorohexane. The solution was stirred for 15 hours at the reflux temperature, effecting quaternization reaction. At the end of reaction, the reaction solution was cooled, to which 4.69 g (0.041 mol) of N,N'-dimethylpiperazine and 20.0 g of methanol were added. The reaction solution was stirred for a further 15 hours at the reflux temperature. At the end of reaction, the reaction solution was cooled and added dropwise to a large volume of acetone whereupon an intermediate polymer precipitated. The precipitate was collected by filtration through a glass filter and dried in vacuum (yield 15.1 g).

Then 15.0 g of the intermediate polymer and 15.0 g of vinylbenzyl chloride (mixture of m- and p-forms) were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 19.2 g).

Except that this polymer was used as a conductive component, a humidity sensor was fabricated as in Example 1 by preparing a coating solution of the polymer and coating it to form a humidity sensitive thin film. Note that the polymer had Mn of about 50,000 prior to crosslinking.

Figure 52:
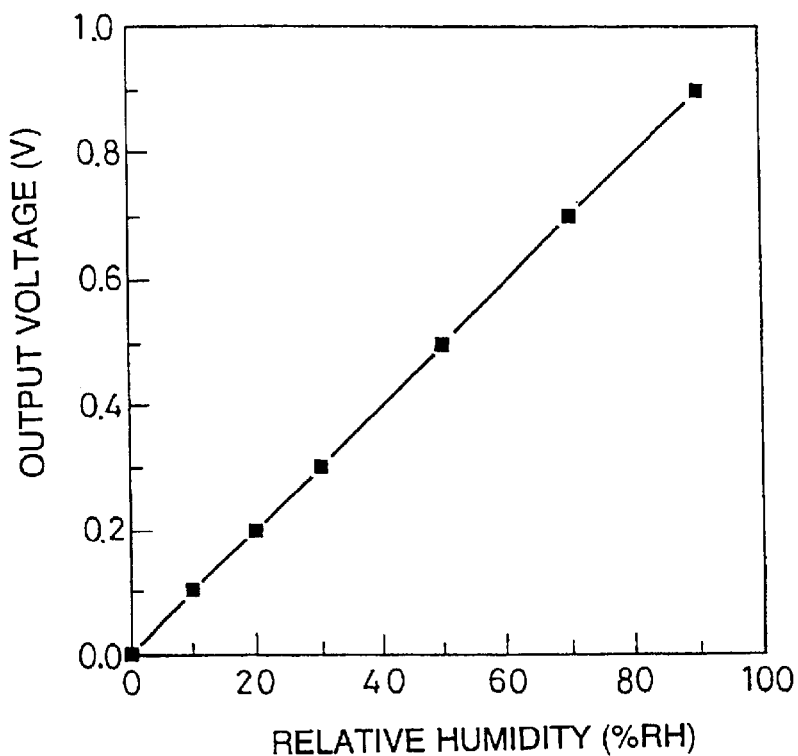
FIGS. 52 and 53 are graphs showing the output and water resistance of the sensor of Example 32, respectively.
Figure 53:
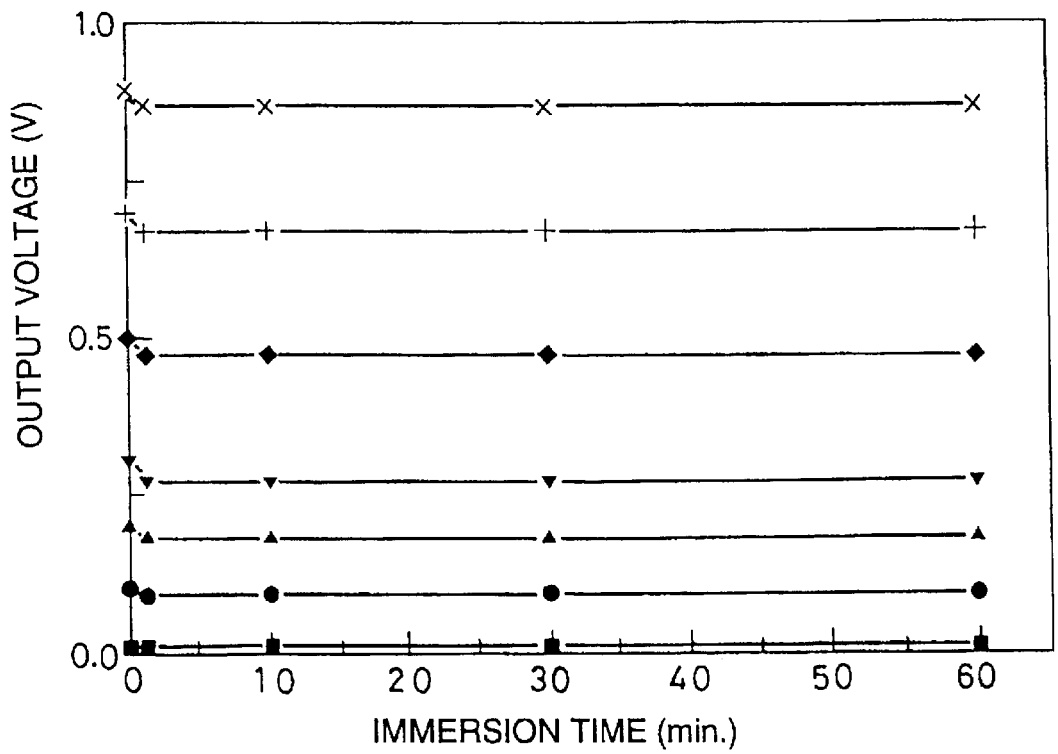

The humidity sensor was evaluated for output and examined by the water resistance test as in Example 1. FIG. 52 shows plots of output voltage versus relative humidity and FIG. 53 shows the results of the water resistance test. The advantages of the present invention are evident from FIGS. 52 and 53.

Example 33

In 10.0 g of methanol were dissolved 4.63 g (0.041 mol) of 1,4-diazabicyclo[2.2.2]octane, 4.71 g (0.041 mol) of N,N'-dimethylpiperazine, and 10.66 g (0.069 mol) of 1,6-dichlorohexane. The solution was stirred for 15 hours at the reflux temperature, effecting quaternization reaction. At the end of reaction, the reaction solution was cooled, to which 4.63 g (0.041 mol) of 1,4-diazabicyclo [2.2.2]octane and 20.0 g of methanol were added. The reaction solution was stirred for a further 15 hours at the reflux temperature. At the end of reaction, the reaction solution was cooled and added dropwise to a large volume of acetone whereupon an intermediate polymer precipitated. The precipitate was collected by filtration through a glass filter and dried in vacuum (yield 17.2 g).

Then 15.0 g of the intermediate polymer and 15.0 g of vinylbenzyl chloride (mixture of m- and p-forms) were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 20.2 g).

Except that this polymer was used as a conductive component, a humidity sensor was fabricated as in Example 1 by preparing a coating solution of the polymer and coating it to form a humidity sensitive thin film. Note that the polymer had Mn of about 70,000 prior to crosslinking.

Figure 54:
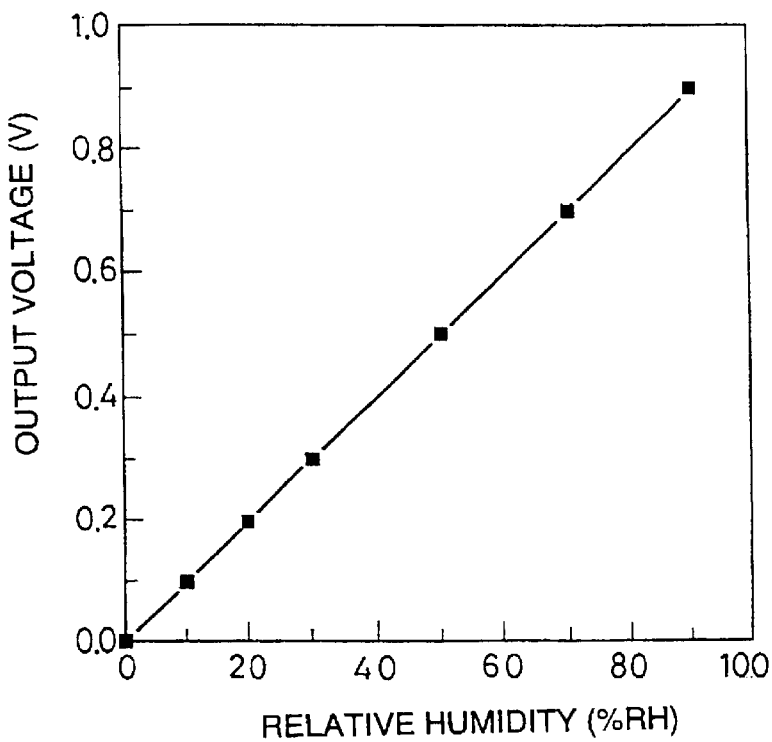
FIGS. 54 and 55 are graphs showing the output and water resistance of the sensor of Example 33, respectively.
Figure 55:
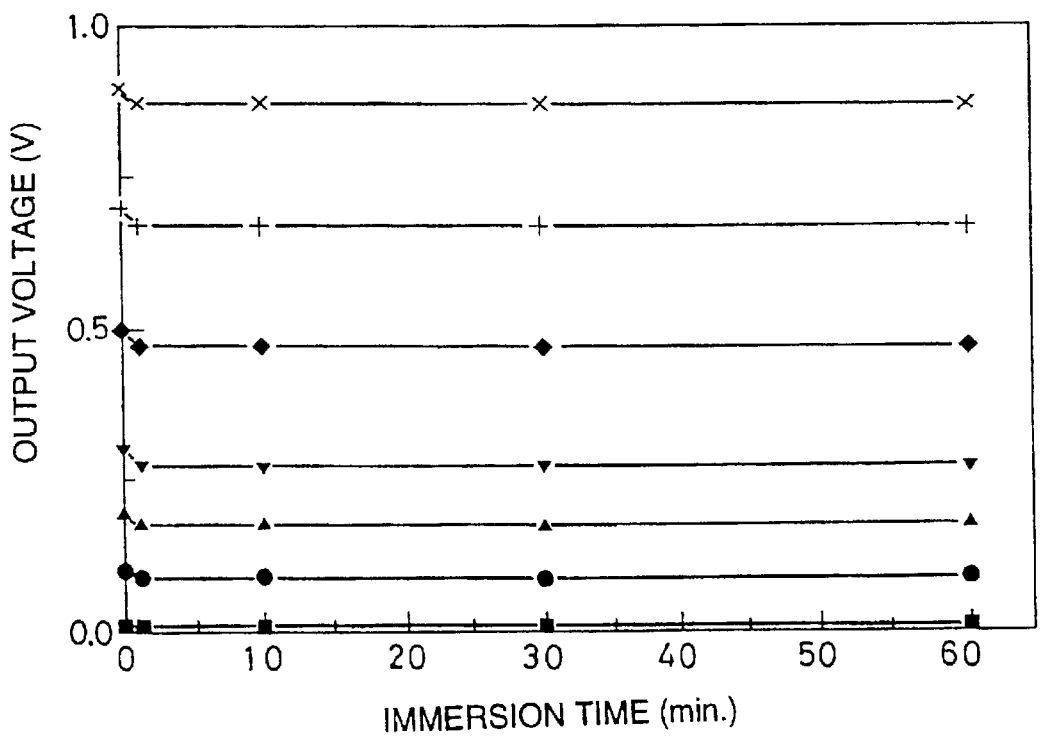

The humidity sensor was evaluated for output and examined by the water resistance test as in Example 1. FIG. 54 shows plots of output voltage versus relative humidity and FIG. 55 shows the results of the water resistance test. The advantages of the present invention are evident from FIGS. 54 and 55.

Example 34

In 10.0 g of methanol were dissolved 8.48 g (0.074 mol) of N,N'-dimethylpiperazine and 13.82 g (0.089 mol) of 1,6-dichlorohexane. The solution was stirred for 15 hours at the reflux temperature, effecting quaternization reaction. At the end of reaction, the reaction solution was cooled, to which 6.91 g (0.045 mol) of 1,6-dichlorohexane and 20.0 g of methanol were added. The reaction solution was stirred for a further 15 hours at the reflux temperature. At the end of reaction, the reaction solution was cooled and added dropwise to a large volume of acetone whereupon an intermediate polymer precipitated. The precipitate was collected by filtration through a glass filter and dried in vacuum (yield 17.1 g).

Then 15.0 g of the intermediate polymer and 15.0 g of N-(3-dimethylaminopropyl)methacrylamide were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 17.4 g).

Except that this polymer was used as a conductive component, a humidity sensor was fabricated as in Example 1 by preparing a coating solution of the polymer and coating it to form a humidity sensitive thin film. Note that the polymer had Mn of about 70,000 prior to crosslinking.

Figure 56:
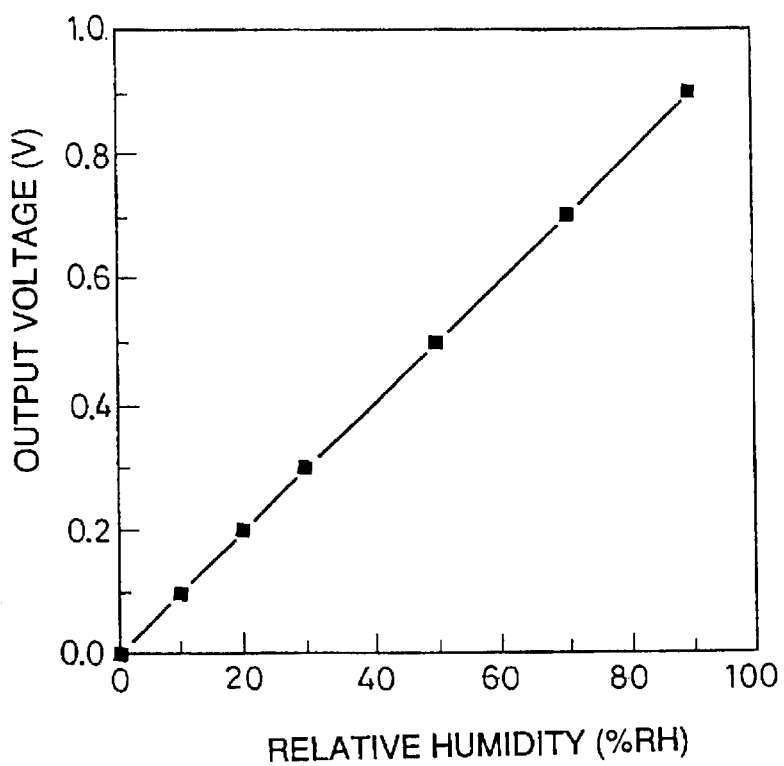
FIGS. 56 and 57 are graphs showing the output and water resistance of the sensor of Example 34, respectively.
Figure 57:
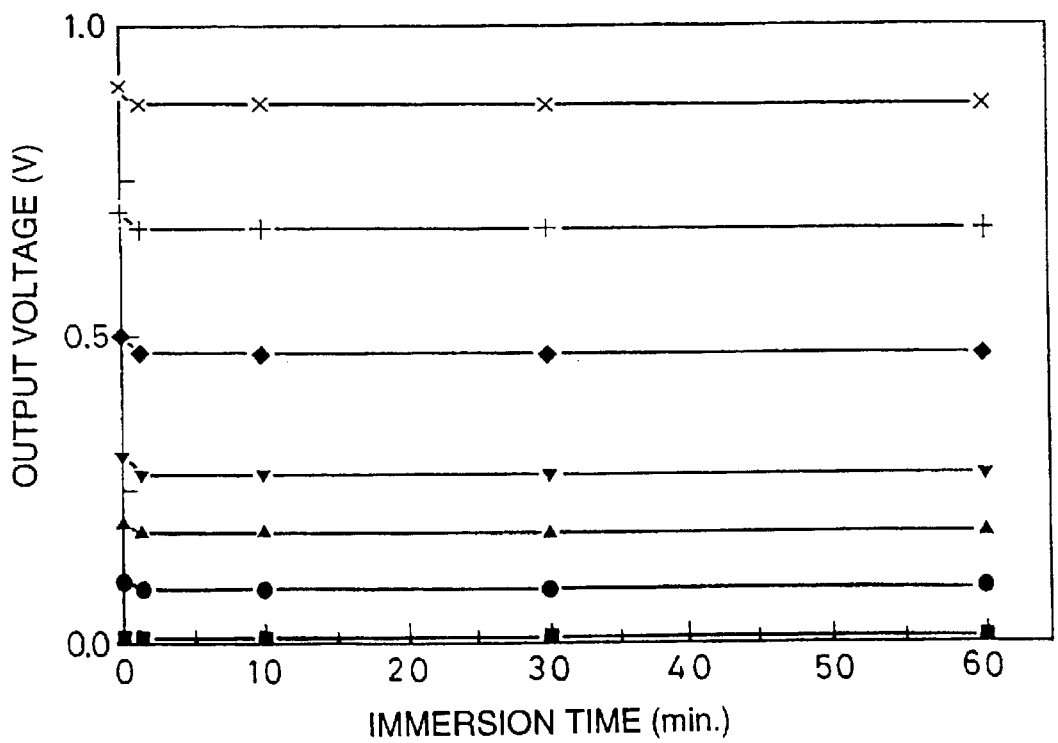

The humidity sensor was evaluated for output and examined by the water resistance test as in Example 1. FIG. 56 shows plots of output voltage versus relative humidity and FIG. 57 shows the results of the water resistance test. The advantages of the present invention are evident from FIGS. 56 and 57.

Example 35

The intermediate polymer synthesized, separated and purified in Example 34, 15.0 g, and 15.0 g of N-(3-dimethylaminopropyl) acrylamide were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 15.1 g).

Except that this polymer was used as a conductive component, a humidity sensor was fabricated as in Example 1 by preparing a coating solution of the polymer and coating it to form a humidity sensitive thin film. Note that the polymer had Mn of about 70,000 prior to crosslinking.

Figure 58:
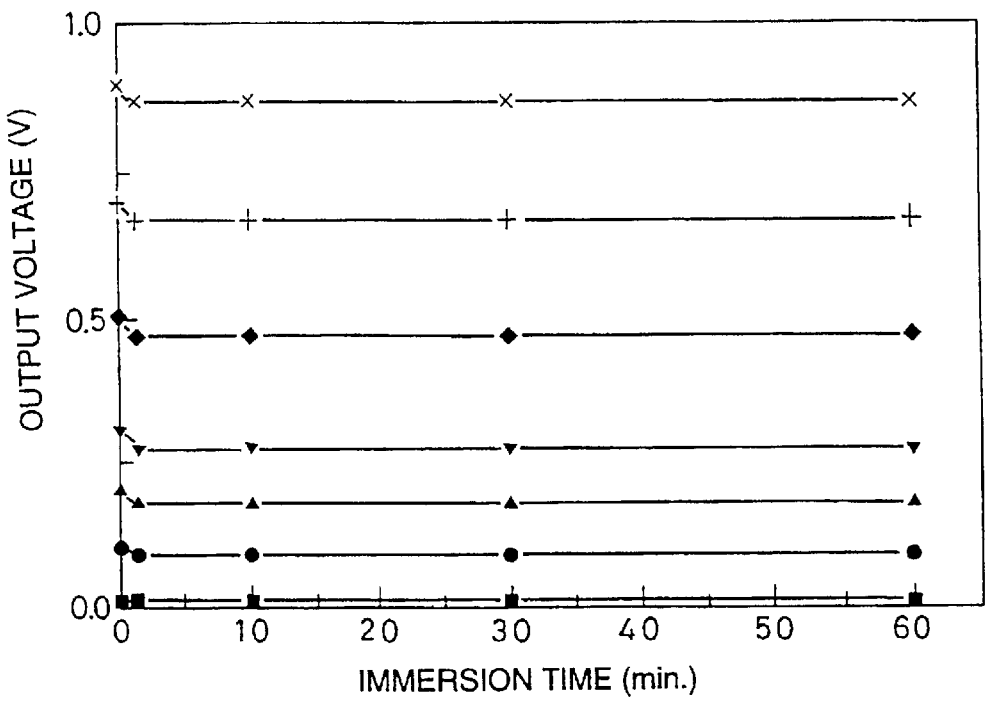
FIG. 58 is a graph showing the water resistance of the humidity sensor of Example 35.

The humidity sensor was evaluated for output and examined by the water resistance test as in Example 1. The output voltage versus relative humidity was the same as in Example 34. FIG. 58 shows the results of the water resistance test. The advantages of the present invention are evident from these results.

Example 36

In 10.0 g of methanol were dissolved 3.75 g (0.033 mol) of 1,4-diazabicyclo[2.2.2]octane, 3.82 g (0.033 mol) of N,N'-dimethylpiperazine, and 12.44 g (0.080 mol) of 1,6-dichlorohexane. The solution was stirred for 15 hours at the reflux temperature, effecting quaternization reaction. At the end of reaction, the reaction solution was cooled, to which 6.22 g (0.040 mol) of 1,6-dichlorohexane and 20.0 g of methanol were added. The reaction solution was stirred for a further 15 hours at the reflux temperature. At the end of reaction, the reaction solution was cooled, to which 30 g of 2-propanol was added. The resulting solution was added dropwise to a large volume of acetone whereupon an intermediate polymer precipitated. The precipitate was collected by filtration through a glass filter and dried in vacuum (yield 17.5 g).

Then 15.0 g of the intermediate polymer and 15.0 g of N-(3-dimethylaminopropyl)methacrylamide were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 18.4 g).

Except that this polymer was used as a conductive component, a humidity sensor was fabricated as in Example 1 by preparing a coating solution of the polymer and coating it to form a humidity sensitive thin film. Note that the polymer had Mn of about 50,000 prior to crosslinking.

Figure 59:
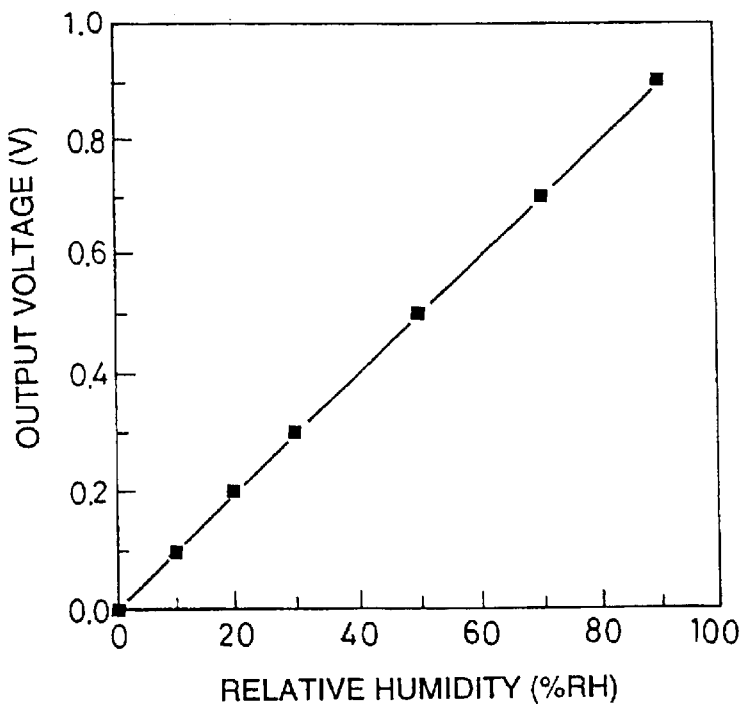
FIGS. 59 and 60 are graphs showing the output and water resistance of the sensor of Example 36, respectively.
Figure 60:
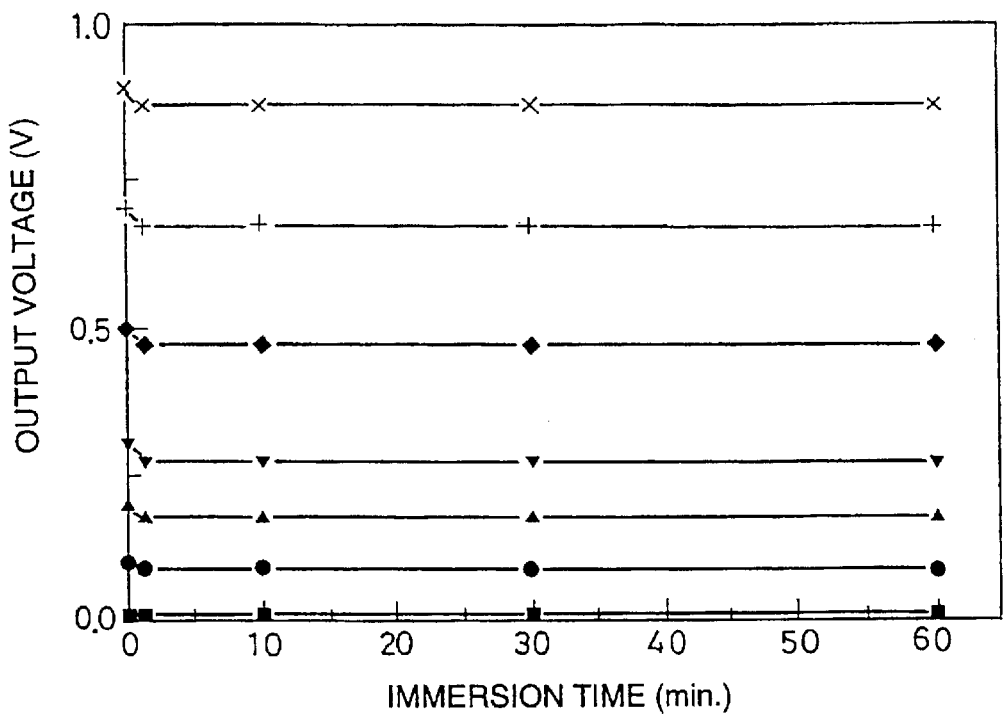

The humidity sensor was evaluated for output and examined by the water resistance test as in Example 1. FIG. 59 shows plots of output voltage versus relative humidity and FIG. 60 shows the results of the water resistance test. The advantages of the present invention are evident from FIGS. 59 and 60.

Example 37

The intermediate polymer synthesized, separated and purified in Example 36, 15.0 g, and 15.0 g of N-(3-dimethylaminopropyl) acrylamide were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 18.2 g).

Except that this polymer was used as a conductive component, a humidity sensor was fabricated as in Example 1 by preparing a coating solution of the polymer and coating it to form a humidity sensitive thin film. Note that the polymer had Mn of about 50,000 prior to crosslinking.

Figure 61:
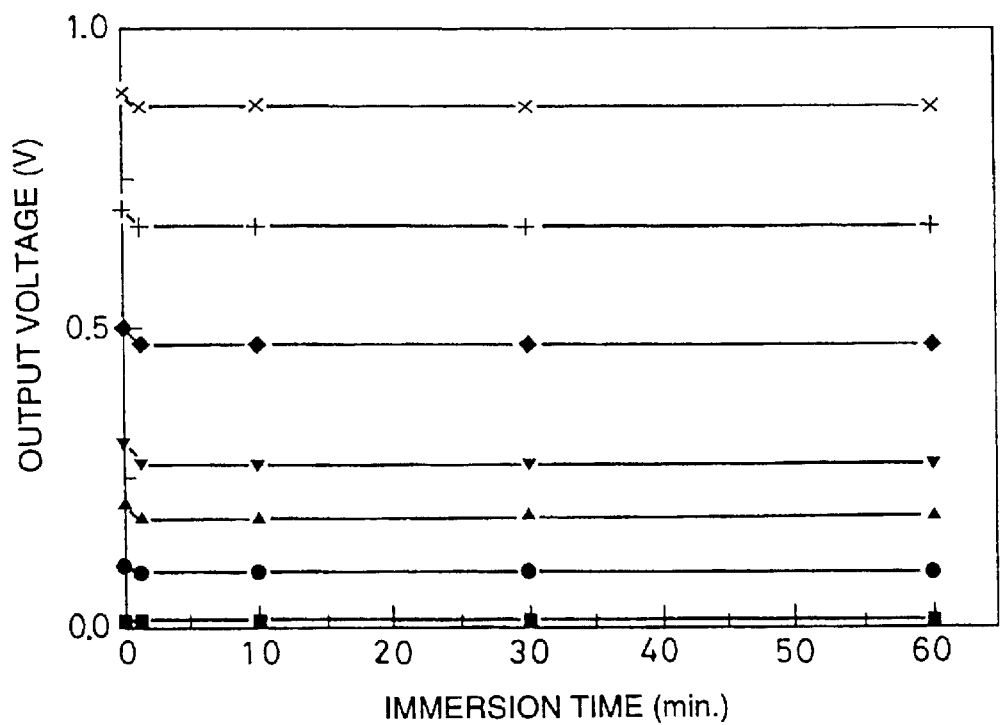
FIG. 61 is a graph showing the water resistance of the humidity sensor of Example 37.

The humidity sensor was evaluated for output and examined by the water resistance test as in Example 1. The output voltage versus relative humidity was the same as in Example 36. FIG. 61 shows the results of the water resistance test. The advantages of the present invention are evident from these results.

Example 38

In 10.0 g of methanol were dissolved 3.74 g (0.033 mol) of N,N'-dimethylpiperazine, 7.80 g (0.033 mol) of 4,4'-trimethylenebis(l-methylpiperidine), and 8.46 g (0.055 mol) of 1,6-dichlorohexane. The solution was stirred for 15 hours at the reflux temperature, effecting quaternization reaction. At the end of reaction, the reaction solution was cooled, to which 3.74 g (0.033 mol) of N,N'-dimethylpiperazine and 20.0 g of methanol were added. The reaction solution was stirred for a further 15 hours at the reflux temperature. At the end of reaction, the reaction solution was cooled and 30 g of 2-propanol was added thereto. The solution was added dropwise to a large volume of acetone whereupon an intermediate polymer precipitated. The precipitate was collected by filtration through a glass filter and dried in vacuum (yield 15.5 g).

Then 15.0 g of the intermediate polymer and 15.0 g of vinylbenzyl chloride (mixture of m- and p-forms) were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 12.2 g).

Except that this polymer was used as a conductive component, a humidity sensor was fabricated as in Example 1 by preparing a coating solution of the polymer and coating it to form a humidity sensitive thin film. Note that the polymer had Mn of about 60,000 prior to crosslinking.

Figure 62:
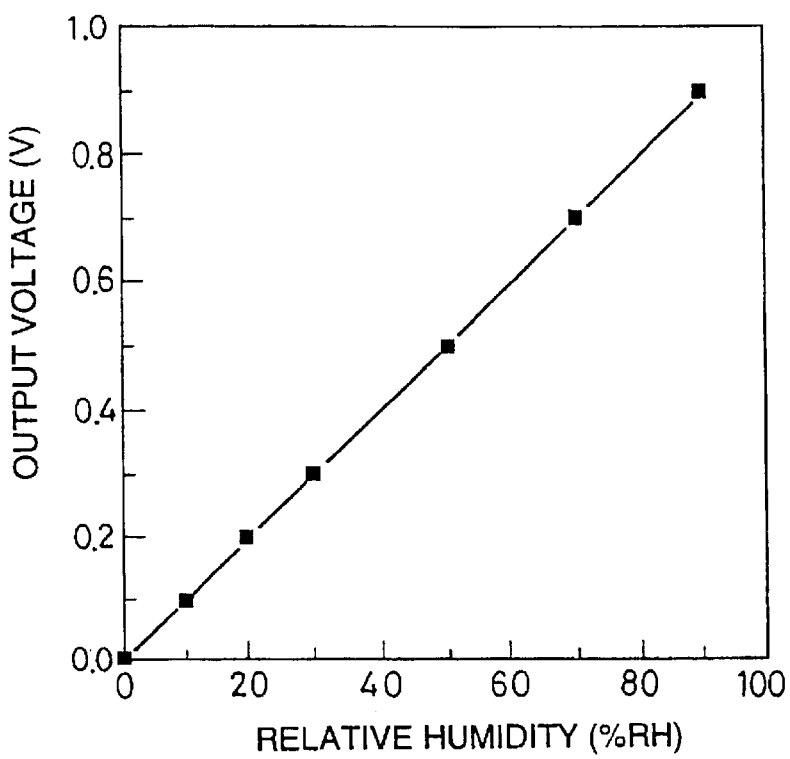
FIGS. 62 and 63 are graphs showing the output and water resistance of the sensor of Example 38, respectively.
Figure 63:
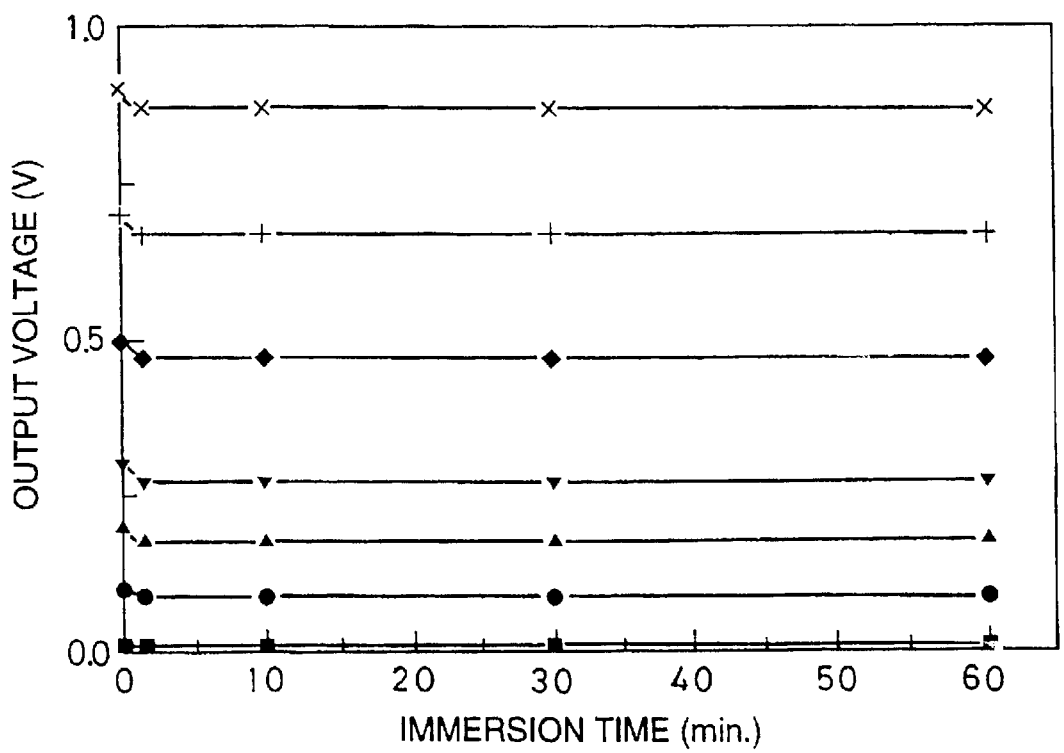

The humidity sensor was evaluated for output and examined by the water resistance test as in Example 1. FIG. 62 shows plots of output voltage versus relative humidity and FIG. 63 shows the results of the water resistance test. The advantages of the present invention are evident from FIGS. 62 and 63.

Example 39

In 10.0 g of methanol were dissolved 3.15 g (0.028 mol) of N,N'-dimethylpiperazine, 6.58 g (0.028 mol) of 4,4'-trimethylenebis(1-methylpiperidine), and 10.27 g (0.065 mol) of 1,6-dichlorohexane. The solution was stirred for 15 hours at the reflux temperature, effecting quaternization reaction. At the end of reaction, the reaction solution was cooled, to which 5.14 g (0.033 mol) of 1,6-dichlorohexane and 20.0 g of methanol were added. The reaction solution was stirred for a further 15 hours at the reflux temperature. At the end of reaction, the reaction solution was cooled and 30 g of 2-propanol was added thereto. The solution was added dropwise to a large volume of acetone whereupon an intermediate polymer precipitated. The precipitate was collected by filtration through a glass filter and dried in vacuum (yield 16.5 g).

Then 15.0 g of the intermediate polymer and 15.0 g of N-(3-dimethylaminopropyl)methacrylamide were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 15.4 g).

Except that this polymer was used as a conductive component, a humidity sensor was fabricated as in Example 1 by preparing a coating solution of the polymer and coating it to form a humidity sensitive thin film. Note that the polymer had Mn of about 50,000 prior to crosslinking.

Figure 64:
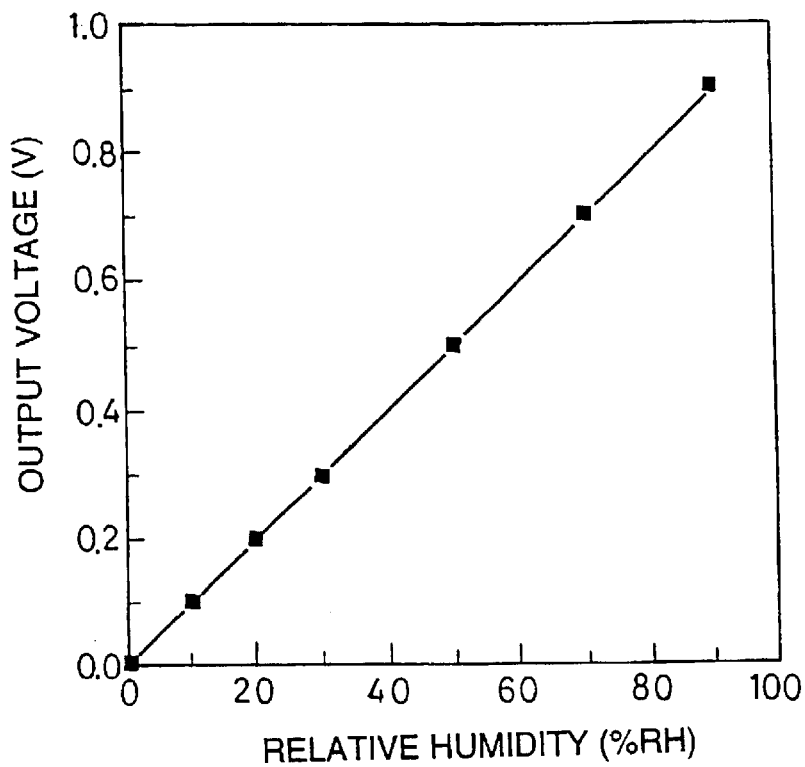
FIGS. 64 and 65 are graphs showing the output and water resistance of the sensor of Example 39, respectively.
Figure 65:
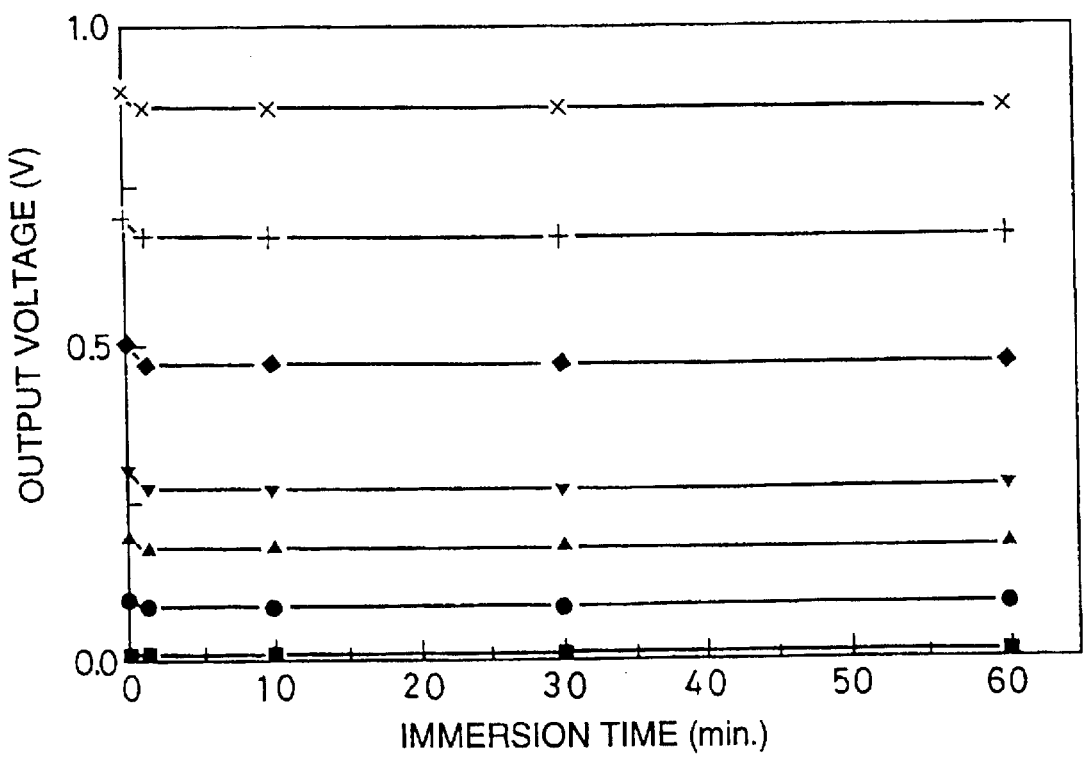

The humidity sensor was evaluated for output and examined by the water resistance test as in Example 1. FIG. 64 shows plots of output voltage versus relative humidity and FIG. 65 shows the results of the water resistance test. The advantages of the present invention are evident from FIGS. 64 and 65.

Example 40

The intermediate polymer synthesized, separated and purified in Example 39, 15.0 g, and 15.0 g of N-(3-dimethylaminopropyl) acrylamide were dissolved in 30.0 g of methanol. The solution was stirred at 25° C. for 24 hours, introducing a reactive group into the intermediate polymer at its end. At the end of reaction, 30 g of 2-propanol was added to the reaction solution, which was added dropwise to a large volume of acetone whereupon the polymer precipitated. The precipitate was collected by filtration through a glass filter and then dried in vacuum (yield 17.9 g).

Except that this polymer was used as a conductive component, a humidity sensor was fabricated as in Example 1 by preparing a coating solution of the polymer and coating it to form a humidity sensitive thin film. Note that the polymer had Mn of about 60,000 prior to crosslinking.

Figure 66:
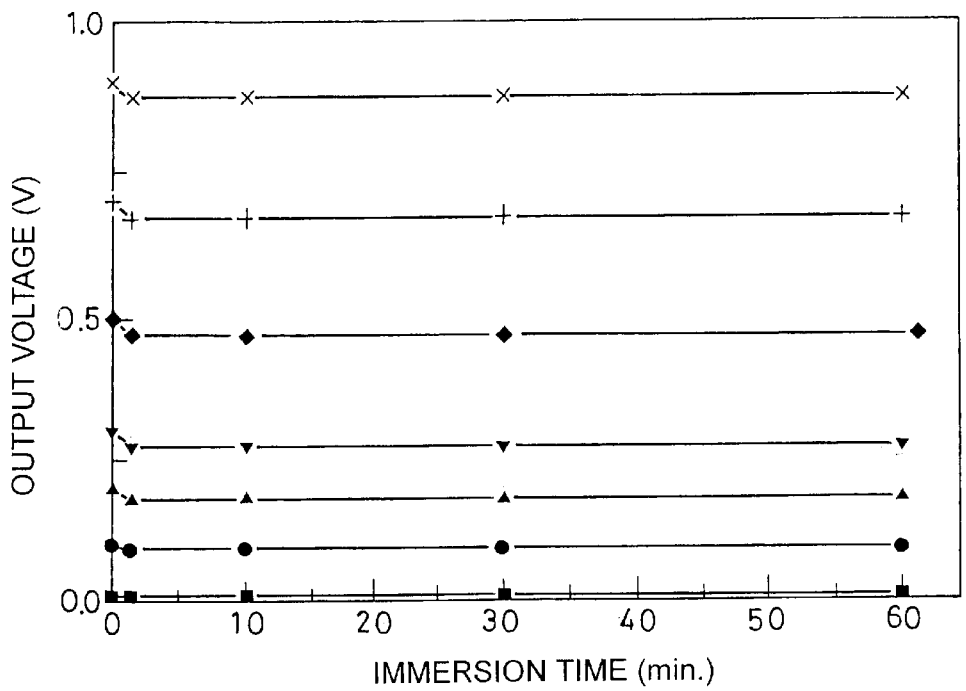
FIG. 66 is a graph showing the water resistance of the humidity sensor of Example 40.

The humidity sensor was evaluated for output and examined by the water resistance test as in Example 1. The output voltage versus relative humidity was the same as in Example 39. FIG. 66 shows the results of the water resistance test. The advantages of the present invention are evident from these results.

Example 41

Humidity sensitive thin films were prepared and humidity sensors were fabricated as in Examples 1–7, 9–11, and 13–40 except that a diamine compound and a dihalogen compound both other than the above-mentioned ones were used in different combinations, the amounts of these compounds added were changed in accordance with the first reaction scheme (Example 1) and the second reaction scheme (Example 13), and a compound having an ethylenically unsaturated reactive group was changed. For combinations of diamine and dihalogen compounds analogous to Examples 8 and 12, humidity sensitive thin films were prepared and humidity sensors were fabricated as in Example 1. These humidity sensors were similarly tested for output and water resistance, finding that results equivalent to those of Examples 1–40 were obtained depending on the particular diamine and dihalogen compounds and reaction conditions used.

Comparative Example 1

Figure 67:
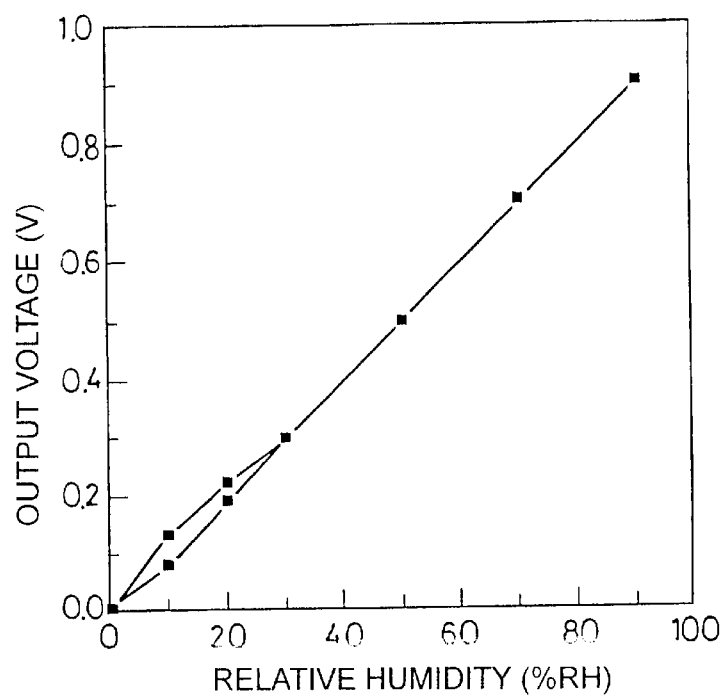
FIG. 67 is a graph showing the output of the humidity sensor of Comparative Example 1.

A humidity sensor was fabricated in accordance with JP-B 62-7976 and examined for output as in Example 1. FIG. 67 shows plots of output voltage versus relative humidity.

The humidity sensitive material used herein was poly(2-hydroxy-3-methacryloxypropyltrimethylammonium chloride) of the following formula. A humidity sensitive thin film was formed by coating a solution of this polymer to an electrode-bearing substrate, applying an ammonium bichromate solution to the coating, baking the coating, irradiating ultraviolet radiation for 2 or 3 minutes for crosslinking.

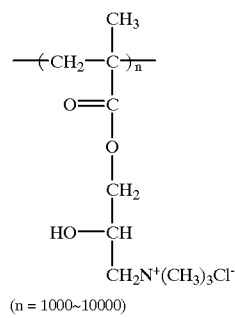

(n = 1000~10000)

It is seen from FIG. 67 that this sensor developed hysteresis in a region of RH 0% to 30%, suggesting inferior output property as compared with the inventive humidity sensors.

Comparative Example 2

The sensor of Example 1 in U.S. Pat. No. 5,546,802 was tested for output before and after exposure to chlorine gas.

Figure 68:
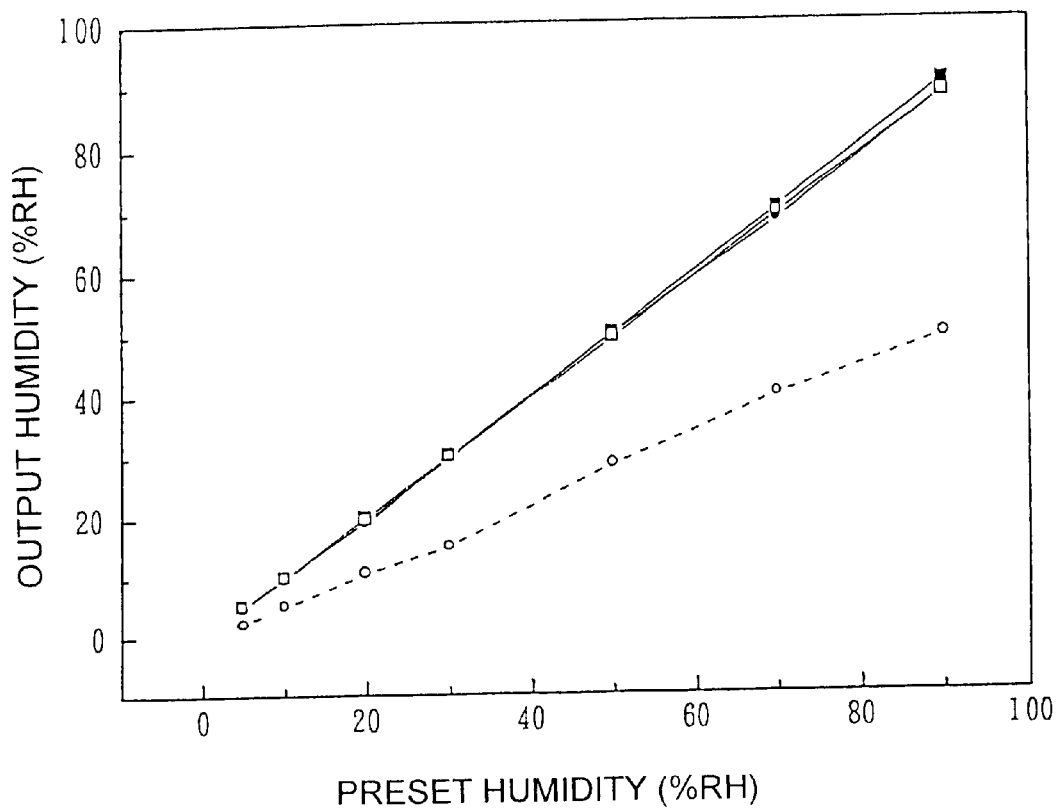
FIG. 68 is a graph showing the performance of the inventive and comparative sensors before and after exposure to chlorine gas.

The gas exposure was by holding the sensor for 96 hours in an atmosphere having a $Cl_2$ gas concentration of 1 ppm, a temperature of 40° C. and a relative humidity (RH) of 70–80%. The sensor of the present Example 1 was tested under the same conditions. The results are shown in FIG. 68. It is evident that the output of the inventive sensor remains unchanged before and after exposure to chlorine gas.

Comparative Example 3

Figure 69:
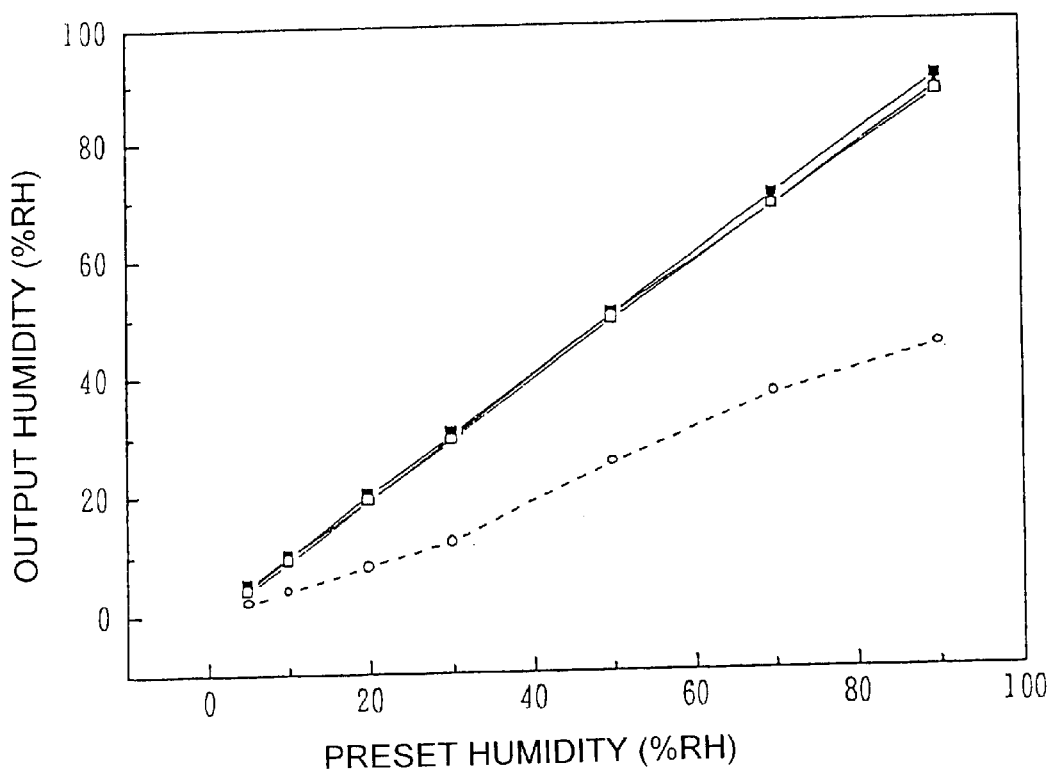
FIG. 69 is a graph showing the performance of the inventive and comparative sensors before and after exposure to nitrogen dioxide gas.

The sensor of Example 1 in U.S. Pat. No. 5,546,802 was tested for output before and after exposure to nitrogen dioxide gas. The gas exposure was by holding the sensor for 96 hours in an atmosphere having a $NO_2$ gas concentration of 1 ppm, a temperature of 40° C. and RH 70–80%. The sensor of the present Example 1 was tested under the same conditions. The results are shown in FIG. 69. It is evident that the output of the inventive sensor remains unchanged before and after exposure to $NO_2$ gas.

Comparative Example 4

Figure 70:
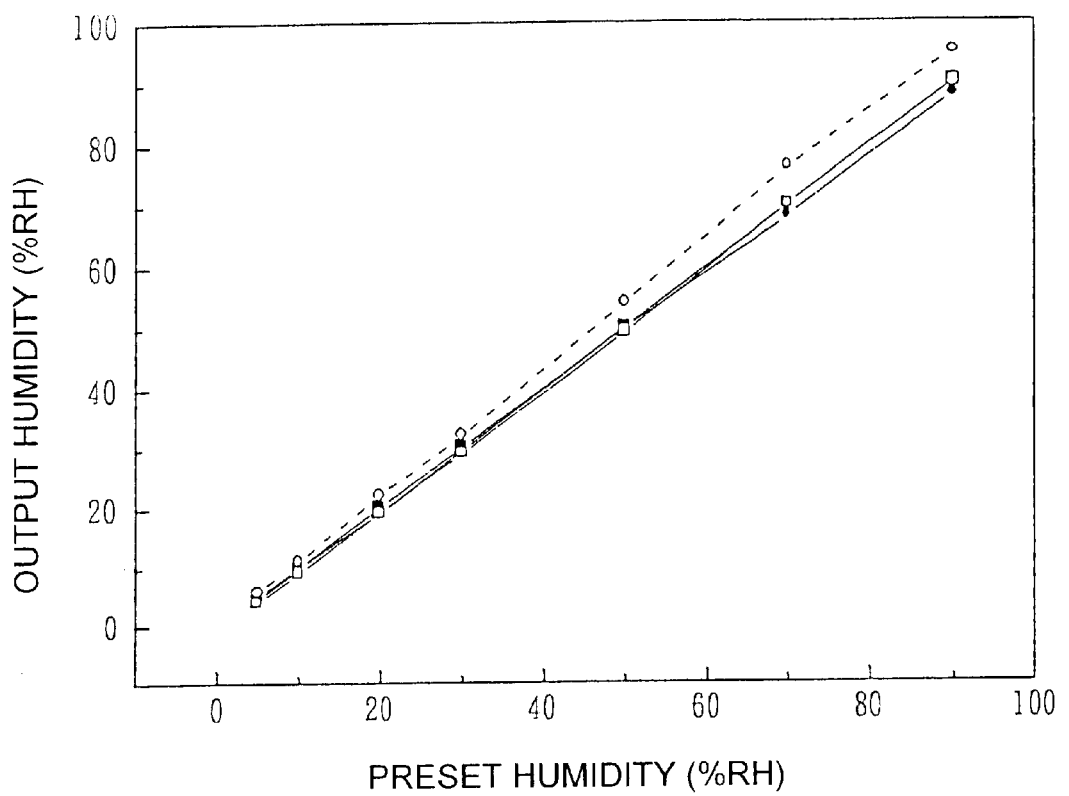
FIG. 70 is a graph showing the performance of the inventive and comparative sensors before and after exposure to sulfur dioxide gas.

The sensor of Example 1 in U.S. Pat. No. 5,546,802 was tested for output before and after exposure to sulfur dioxide gas. The gas exposure was by holding the sensor for 96 hours in an atmosphere having a $SO_2$ gas concentration of 5 ppm, a temperature of 40° C. and RH 70–80%. The sensor of the present Example 1 was tested under the same conditions. The results are shown in FIG. 70. It is evident that the output of the inventive sensor remains unchanged before and after exposure to $SO_2$ gas.

Comparative Example 5

Figure 71:
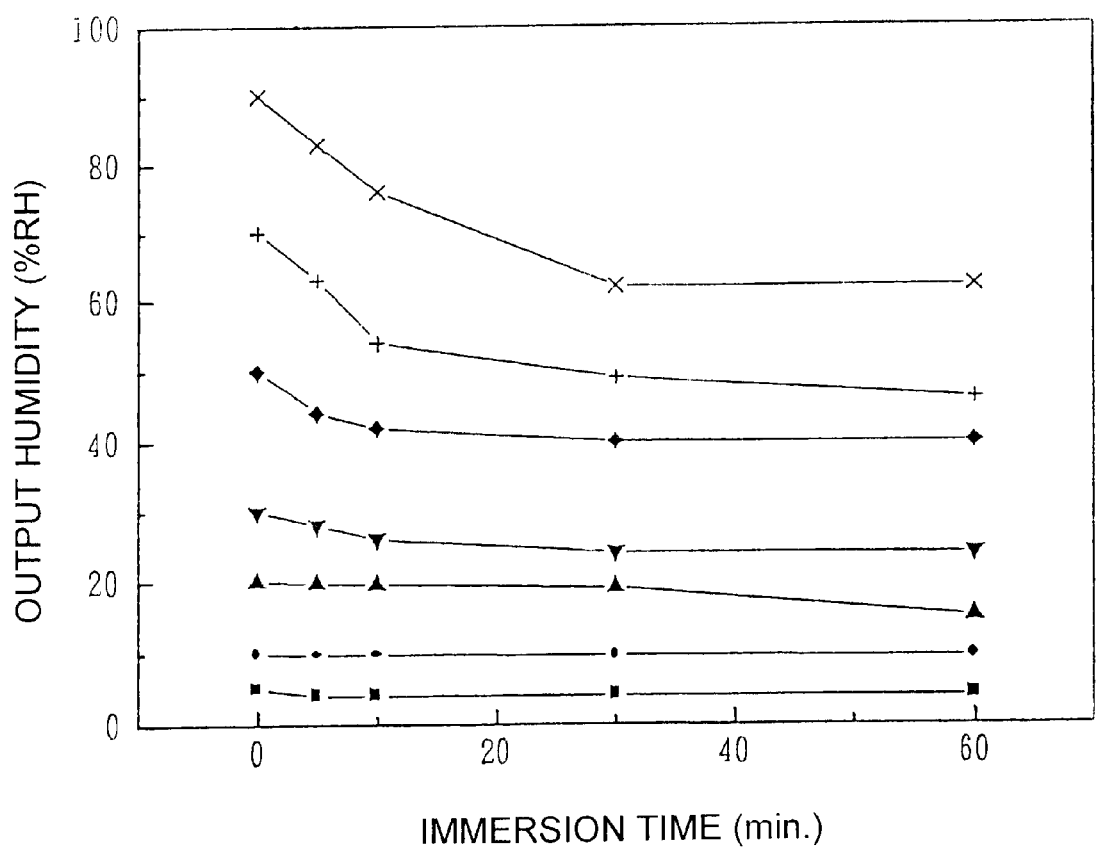
FIG. 71 is a graph showing the water resistance of the sensor without the undercoat layer in Comparative Example 5.

A humidity sensor was fabricated as in Example 1 except that the coating solution of the polymer in Example 1 was applied directly to the substrate without the intervening layer of KBM1003. A water resistance test was conducted on this sensor as in Example 1. FIG. 71 shows the results of the water resistance test. It is seen from FIG. 71 that absent the silane compound layer, the humidity sensitive film swelled and stripped during the water resistance test, indicating poor water resistance.

Comparative Example 6

Humidity sensors were fabricated as in Example 1 except that in the step of applying the coating solution of the polymer by dispensing, the amount of the solution dispensed was changed to 0.5 μl, 0.75 μl, 1.0 μl, 1.25 μl and 1.50 μl, thereby changing the thickness of the humidity sensitive film to 1.2 μm, 1.8 μm, 2.3 μm, 2.9 μm and 3.2 μm, respectively. As in Comparative Examples 2 to 4, these sensors were tested for output before and after exposure to chlorine, nitrogen dioxide and sulfur dioxide gases, from which output changes by gas exposure were computed. The results are shown in Table 1.

TABLE 1

| Amount dispensed | Average film | Output change (%) | | |
|---|---|---|---|---|
| (μl) | thickness (μm) | $NO_2$ | $Cl_2$ | $SO_2$ |
| 0.5 | 1.2 | −2.9 | −5.9 | −4.3 |
| 0.75 | 1.8 | −2.8 | −3.8 | −2.8 |
| 1.0 | 2.3 | −1.6 | −2.5 | −1.3 |
| 1.25 | 2.9 | −1.2 | −1.2 | −0.9 |
| 1.5 | 3.2 | −1.0 | −0.4 | −0.5 |

It is evident from Table 1 that the thicker the moisture sensitive film, the less becomes the gas influence.

There has been described a humidity sensor which is fully resistant to water so that it ensures stable operation over a long time even in a dew condensing atmosphere. The sensor is free of hysteresis and able to measure humidity over a very wide range.

Japanese Patent Application No. 2000-098643 is incorporated herein by reference.

While the invention has been described in connection with what is presently considered to be the most practical and preferred embodiment, it will be understood that the invention is not to be limited to the disclosed embodiment, but on the contrary, is intended to cover various modifications and equivalent arrangements included within the spirit and scope of the appended claims.

What is claimed is:

1. A humidity sensor comprising an insulating substrate, a pair of opposed electrodes disposed on the substrate and defining a gap therebetween, a silicon-containing undercoat layer lying on at least the gap, and a humidity sensitive thin film lying thereon, said humidity sensitive thin film comprising a crosslinked product of a conductive polymer having ethylenically unsaturated groups and being physically bound to said undercoat layer through an interpenetrating polymer network.

2. The humidity sensor of claim 1 wherein said humidity sensitive thin film has a thickness of 0.1 to 20 μm.

3. A humidity sensor comprising an insulating substrate, a pair of opposed electrodes disposed on the substrate and defining a gap therebetween, a silicon-containing undercoat layer lying on at least the gap, and a humidity sensitive thin film lying thereon, said humidity sensitive thin film comprising a crosslinked product of a polymer of the following formula (I) and being bound to said undercoat layer through covalent bonds having not undergone dehalogenation reaction,

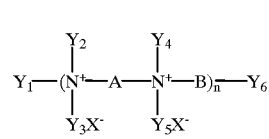

(I)

wherein A and B each are a divalent group, $Y_1$, $Y_2$, $Y_3$, $Y_4$, $Y_5$ and $Y_6$ each are a monovalent group, at least one of $Y_1$ to $Y_6$ is a group terminated with an ethylenically unsaturated reactive group, at least two of $Y_1$, $Y_2$, $Y_3$, $Y_4$, $Y_5$, A and portions thereof adjoining the nitrogen (N) atom or at least two of $Y_4$, $Y_5$, $Y_6$, B and portions thereof adjoining the nitrogen (N) atom, taken together, may form a ring with the nitrogen atom, $X^-$ is a halide ion, and letter n is a number of 2 to 5,000.

4. The humidity sensor of claim 3 wherein said humidity sensitive thin film is physically bound to said undercoat layer through an interpenetrating polymer network.

5. The humidity sensor of claim 3 wherein said polymer has the following formula (II) or (III):

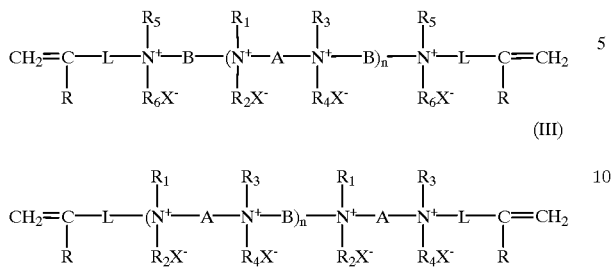

(II)

(III)

wherein A and B each are a divalent group, each of $R_1$, $R_2$, $R_3$, and $R_4$ is an alkyl or alkenyl group, $R_1$ and $R_2$, $R_1$ and A or a portion of A, $R_2$ and A or a portion of A, $R_3$ and $R_4$, $R_3$ and A or a portion of A, $R_4$ and A or a portion of A, $R_1$ and $R_3$, $R_1$ and $R_4$, $R_2$ and $R_3$, or $R_2$ and $R_4$, taken together, may form a ring with the nitrogen (N) atom, L is a divalent group, R is hydrogen or an alkyl group, $X^-$ is a halide ion, n is a number of 2 to 5,000, and $R_5$ and $R_6$ each are an alkyl or alkenyl group.

6. The humidity sensor of claim 3 wherein the divalent group represented by A is an alkylene, alkenylene or arylene group or a mixture thereof.

7. The humidity sensor of claim 3 wherein the divalent group represented by B is an alkylene, alkenylene or arylene group in which at least one of an oxy group (—O—) and a carbonyl group (—CO—) may intervene or a mixture thereof.

8. The humidity sensor of claim 3 wherein said polymer is obtained by reacting a diamine compound with a dihalogen compound to form an intermediate polymer and introducing an ethylenically unsaturated reactive group into the intermediate polymer at each end.

9. A method for preparing a humidity sensor comprising the steps of:

applying a silane compound containing at least a hydrolyzable group and an organic group having an unsaturated bond onto a substrate to form an undercoat layer, applying a solution containing a conductive polymer having ethylenically unsaturated groups onto the undercoat layer, and exposing the conductive polymer to radiation for crosslinking the polymer and bonding the polymer with the silane compound to thereby form a humidity sensitive thin film.

10. The method of claim 9 wherein the bond between the conductive polymer and the silane compound is due to covalent bonds by crosslinking between the ethylenically unsaturated groups and the unsaturated bonds.

11. The method of claim 9 wherein the radiation is ultraviolet radiation.

12. The method of claim 9 wherein said conductive polymer has the following formula (I):

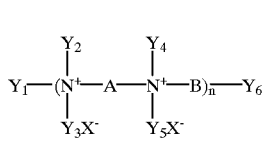

(I)

wherein A and B each are a divalent group, $Y_1$, $Y_2$, $Y_3$, $Y_4$, $Y_5$, and $Y_6$ each are a monovalent group, at least one of $Y_1$ to $Y_6$ is a group terminated with an ethylenically unsaturated reactive group, at least two of $Y_1$, $Y_2$, $Y_3$, $Y_4$, $Y_5$, A and portions thereof adjoining the nitrogen (N) atom or at least two of $Y_4$, $Y_5$, $Y_6$, B and portions thereof adjoining the nitrogen (N) atom, taken together, may form a ring with the nitrogen atom, $X^-$ is a halide ion, and letter n is a number of 2 to 5,000.

13. The method of claim 9 wherein said silane compound has the following formula (IV):

(IV)

wherein $X^0$ is a hydrolyzable group, $R^0$ is an organic group, and n is an integer of 1, 2 or 3.

* * * * *

UNITED STATES PATENT AND TRADEMARK OFFICE
CERTIFICATE OF CORRECTION

PATENT NO. : 6,568,265 B2
DATED : May 27, 2003
INVENTOR(S) : Akira Shibue et al.

It is certified that error appears in the above-identified patent and that said Letters Patent is hereby corrected as shown below:

<u>Title page,</u>
Item [75], Inventors, should read
-- [75] Inventors: Akira Shibue, Tokyo (JP); Kenryo Nambo, Tokyo (JP) --.

Signed and Sealed this

Seventh Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,568,265 B2 Page 1 of 1
APPLICATION NO. : 09/820644
DATED : May 27, 2003
INVENTOR(S) : Akira Shibue et al.

It is certified that error appears in the above-identified patent and that said Letters Patent is hereby corrected as shown below:

<u>Title page,</u>
Item [75], Inventors, should read
-- [75]  Inventors: Akira Shibue, Tokyo (JP); Kenryo Namba, Tokyo (JP) --.

This certificate supersedes Certificate of Correction issued October 7, 2003.

Signed and Sealed this

Tenth Day of October, 2006

JON W. DUDAS
*Director of the United States Patent and Trademark Office*